US011756183B2

(12) United States Patent
Jaffrey et al.

(10) Patent No.: US 11,756,183 B2
(45) Date of Patent: Sep. 12, 2023

(54) RNA MOLECULES, METHODS OF PRODUCING CIRCULAR RNA, AND TREATMENT METHODS

(71) Applicant: CORNELL UNIVERSITY, Ithaca, NY (US)

(72) Inventors: Samie R. Jaffrey, New York, NY (US); Jacob L. Litke, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 713 days.

(21) Appl. No.: 16/625,562

(22) PCT Filed: Jun. 23, 2018

(86) PCT No.: PCT/US2018/039182
§ 371 (c)(1),
(2) Date: Dec. 20, 2019

(87) PCT Pub. No.: WO2018/237372
PCT Pub. Date: Dec. 27, 2018

(65) Prior Publication Data
US 2021/0340542 A1 Nov. 4, 2021

Related U.S. Application Data

(60) Provisional application No. 62/524,189, filed on Jun. 23, 2017.

(51) Int. Cl.
*A61K 31/7115* (2006.01)
*G06T 7/00* (2017.01)
(Continued)

(52) U.S. Cl.
CPC .......... *G06T 7/001* (2013.01); *A61K 31/7115* (2013.01); *C12N 15/115* (2013.01);
(Continued)

(58) Field of Classification Search
CPC ............ C12N 15/115; C12N 2310/128; C12N 2310/3519; C12N 2310/532
See application file for complete search history.

(56) References Cited

U.S. PATENT DOCUMENTS 5,773,244 A 6/1998 Ares, Jr. et al.
6,210,931 B1 5/2001 Feldstein et al.
(Continued)

FOREIGN PATENT DOCUMENTS

WO 2005/001039 A2 1/2005
WO 2010/096584 A1 8/2010
WO 2013/119690 A1 8/2013

OTHER PUBLICATIONS

Filonov et al, Broccoli: Rapid Selection of an RNA Mimic of Green Fluorescent Protein by Fluorescence-Based Selection and Directed Evolution, JACS, 2014, 136: 16299-16308 (Year: 2014).*

(Continued)

*Primary Examiner* — Ekaterina Poliakova-Georgantas
(74) *Attorney, Agent, or Firm* — Troutman Pepper Hamilton Sanders LLP (Rochester)

(57) ABSTRACT

The present invention relates to a RNA molecule comprising a first ribozyme, a first ligation sequence, an effector molecule, a second ligation sequence, and a second ribozyme. Methods of producing circular RNA molecules and treatment methods are also disclosed.

22 Claims, 19 Drawing Sheets

Specification includes a Sequence Listing.

(51) Int. Cl.
G06T 7/11 (2017.01)
C12N 15/115 (2010.01)
C12N 15/63 (2006.01)
G01N 21/88 (2006.01)
G01N 21/95 (2006.01)
G01N 21/956 (2006.01)

(52) U.S. Cl.
CPC ......... *C12N 15/63* (2013.01); *G01N 21/8851* (2013.01); *G01N 21/9501* (2013.01); *G01N 21/95607* (2013.01); *G06T 7/11* (2017.01); *C12N 2310/128* (2013.01); *C12N 2310/16* (2013.01); *C12N 2310/3519* (2013.01); *C12N 2310/51* (2013.01); *C12N 2310/532* (2013.01); *G01N 2021/95615* (2013.01); *G06T 2207/20104* (2013.01); *G06T 2207/30148* (2013.01)

(56) References Cited

U.S. PATENT DOCUMENTS

2010/0137407 A1   6/2010   Abe et al.
2019/0040405 A1   2/2019   Cigan et al.

OTHER PUBLICATIONS

Eiler et al., Structural basis for the fast self-cleavage reaction catalyzed by the twister ribozyme, PNAS, 2014, 111: 13028-13033 (Year: 2014).*

Weingarten-Gabbay et al., Systematic discovery of cap-independent translation sequences in human and viral genomes, Science, 2016, 351, 6270: 1-13 (Year: 2016).*

Supplementary European Search Report and Opinion in EP 18819805.5 (dated Feb. 16, 2021).

Nelissen et al., "Fast Production of Homogenous Recombinant RNA—Towards Large-Scale Production of RNA," Nucleic Acids Res. 40(13):e102 (2012).

Roth et al., "A Widespread Self-Cleaving Ribozyme Class is Revealed by Bioinformatics," Nat. Chem. Bio. 10(1):56-60 (2014).

Petkovic et al., "RNA Circulization Strategies In Vivo and In Vitro," Nucleic Acids Res. 43(4):2454-5465 (2015).

Litke & Jaffrey, "Highly Efficient Expression of Circular RNA Aptamers in Cells Using Autocatalytic Transcripts," Nat. Biotechnol. 37(6):677-675 (2019).

International Search Report and Written Opinion for corresponding Application No. PCT/US2018/039182 (dated Oct. 3, 2018).

Ferré-D'Amaré & Scott, "Small Self-Cleaving Ribozymes," Cold Spring Harb. Persepct. Biol. 2(a003574):1-10 (2010).

Ohkawa et al., "Importance of Independence in Ribozyme Reactions: Kinetic Behavior of Trimmed and of Simply Connected Multiple Ribozymes with Potential Activity Against Human Immunodeficiency Virus," Proc. Natl. Acad. Sci. U.S.A. 90:11302-11306 (1993).

Grosshans & Cech, "A Hammerhead Ribozyme Allows Synthesis of a New Form of the Tetrahymena Ribozyme Homogeneous in Length with a 3' End Blocked for Transesterification," Nuc. Acid. Res. 19(14):3875-3880 (1991).

Yin et al., "Long Noncoding RNAs with snoRNA Ends," Mol. Cell 48:219-230 (2012).

Ronald R. Breaker, "Mechanistic Debris Generated by Twister Ribozymes," ACS Chem. Biol. 12:886-891 (2017).

Lu et al., "Metazoan tRNA Introns Generate Stable Circular RNAs In vivo," RNA 21(9):1-12 (2015).

Umekage et al., "In vivo Circular RNA Expression by the Permuted Intron-Exon Method," Innovation Biotechnol., Dr. Eddy C. Agbo (Ed.), ISBN: 978-953-51-0096-6, InTech, Available from: http://www.intechopen.com/books/innovations-in-biotechnology/invivo-circular-rna-expression-by-the-permuted-intron-exon-method (Feb. 17, 2012).

Schmidt et al., "A Method for Expressing and Imaging Abundant, Stable, Circular RNAs In vivo Using tRNA Splicing," Method Enzymol. 572:215-236 (2016).

Lu et al., "A Synthetic Biology Approach Identifies the Mammalian UPR RNA Ligase RtcB," Mol. Cell. 55:758-770 (2014).

Tanaka et al., "RtcB, a Novel RNA Ligase, Can Catalyze tRNA Splicing and HAC1 mRNA Splicing In vivo," J. Biol. Chem. 286(35):30253-30257 (2011).

RNA Society: The 21st Annual Meeting of the RNA Society, The RNA Society of Japan 18th Annual Meeting, Kyoto, Japan (Jun. 28-Jul. 2, 2016).

Wegner et al. "Circular Synthesized CRISPR/Cas gRNAs for Functional Interrogations in the Coding and Noncoding Genome," Elife 8:e42549, pp. 1-31 (2019).

Hasegawa et al., "Detection of mRNA in Mammalian Cells with a Split Ribozyme Reporter," Chem. Bio. Chem. 7:925-928 (2006).

European Search Report and Opinion in EP 18819805.5 (dated Oct. 17, 2022).

* cited by examiner

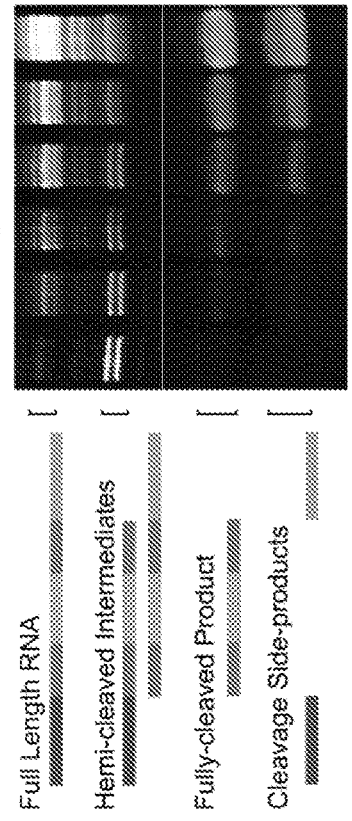
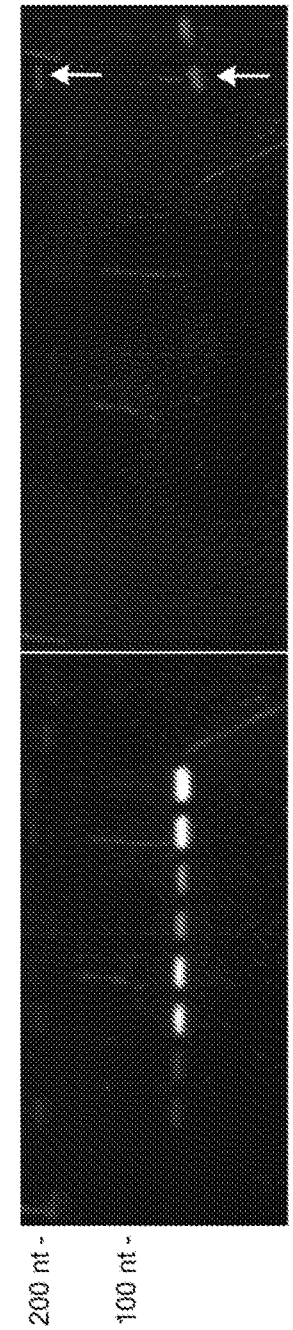
FIGS. 4B-4D

A

B

A

B

SEQUENCE LISTING

<160> NUMBER OF SEQ ID NOS: 1

<210> SEQ ID NO 1
<211> LENGTH: 6358
<212> TYPE: DNA
<213> ORGANISM: Artificial Sequence
<220> FEATURE:
<223> OTHER INFORMATION: pAV-U6+27-Tornado-Broccoli

<400> SEQUENCE: 1

```
gccggatcca aggtcgggca ggaagagggc ctatttccca tgattccttc atatttgcat      60
atacgataca aggctgttag agagataatt agaattaatt tgactgtaaa cacaaagata     120
ttagtacaaa atacgtgacg tagaaagtaa taatttcttg ggtagtttgc agttttaaaa     180
ttatgtttta aaatggacta tcatatgctt accgtaactt gaaagtattt cgatttcttg     240
gctttatata tcttgtggaa aggacgaaac accgtgctcg cttcggcagc acatatacta     300
gtcgacggcc atcagtcgcc ggtcccaagc ccggataaaa tgggagggg cgggaaaccg     360 cctaaccatg ccgactgatg gcaggagacg gtcgggtcca gatattcgta tctgtcgagt     420
agagtgtggg ctcctgccat cagtcggcgt ggactgtaga acactgccaa tgccggtccc     480
aagcccggat aaaagtggag ggtacagtcc acgctctaga gcggacttcg gtccgctttt     540
tactaggacc tgcaggcatg caagcttgac gtcggttacc gatatccata tggcggccgc     600
atcgatctcg agccgcggac tagtaacttg tttattgcag cttataatgg ttacaaataa     660
agcaatagca tcacaaattt cacaaataaa gcattttttt cactgcattc tagttgtggt     720
ttgtccaaac tcatcaatgt atcttatcat gtcttacgta gataagtagc atggcgggtt     780
```

```
aatcattaac tacaaggaac ccctagtgat ggagttggcc actccctctc tgcgcgctcg    840
ctcgctcact gaggccgggc gaccaaaggt cgcccgacgc ccgggctttg cccgggcggc    900
ctcagtgagc gagcgagcgc gcagagaggg agtggccaaa gatctctggc gtaatagcga    960
agaggcccgc accgatcgcc cttcccaaca gttgcgcagc ctgaatggct aatgggaaat   1020
tgtaaacgtt aatattttgt taatattttg ttaaaattcg cgttaaattt ttgttaaatc   1080
agctcatttt ttaaccaata ggccgaaatc ggcaaaatcc cttataaatc aaagaatag    1140 accgagatag ggttgagtgt tgttccagtt tggaacaaga gtccactatt aaagaacgtg   1200
gactccaacg tcaaagggcg aaaaaccgtc tatcagggcg atgcccact  acgtgaacca   1260 tcaccctaat caagtttttt ggggtcgagg tgccgtaaag cactaaatcg aaccctaaa    1320 gggatgcccc gatttagagc ttgacgggga agccggcga  acgtggcgag aaaggaaggg   1380
aagaaagcga aaggagcggg cgctagggcg ctggcaagtg tagcggtcac gctgcgcgta   1440
accaccacac ccgccgcgct taatgcgccg ctacagggcg cgtcaggtgg cacttttcgg   1500
ggaaatgtgc gcggaacccc tatttgttta ttttttctaaa tacattcaaa tatgtatccg   1560
ctcatgagac aataaccctg ataaatgctt caataatatt gaaaaaggaa gagtatgagt   1620
attcaacatt tccgtgtcgc ccttattccc ttttttgcgg cattttgcct tcctgttttt   1680
gctcacccag aaacgctggt gaaagtaaaa gatgctgaag atcagttggg tgcacgagtg   1740
ggttacatcg aactggatct caacagcggt aagatccttg agagttttcg ccccgaagaa   1800
cgttttccaa tgatgagcac ttttaaagtt ctgctatgtg gcgcggtatt atcccgtatt   1860
gacgccgggc aagagcaact cggtcgccgc atacactatt ctcagaatga cttggttgag   1920
tactcaccag tcacagaaaa gcatcttacg gatggcatga cagtaagaga attatgcagt   1980
gctgccataa ccatgagtga taacactgcg gccaacttac ttctgacaac gatcggagga   2040
ccgaaggagc taaccgcttt tttgcacaac atgggggatc atgtaactcg ccttgatcgt   2100
tgggaaccgg agctgaatga agccatacca aacgacgagc gtgacaccac gatgcctgta   2160
gcaatggcaa caacgttgcg caaactatta actggcgaac tacttactct agcttcccgg   2220
caacaattaa tagactggat ggaggcggat aaagttgcag gaccacttct gcgctcggcc   2280
cttccggctg gctggtttat tgctgataaa tctggagccg gtgagcgtgg gtctcgcggt   2340
atcattgcag cactggggcc agatggtaag ccctcccgta tcgtagttat ctacacgacg   2400
gggagtcagg caactatgga tgaacgaaat agacagatcg ctgagatagg tgcctcactg   2460
attaagcatt ggtaactgtc agaccaagtt tactcatata tactttagat tgatttaaaa   2520
cttcattttt aatttaaaag gatctaggtg aagatccttt ttgataatct catgaccaaa   2580
atcccttaac gtgagttttc gttccactga gcgtcagacc ccgtagaaaa gatcaaagga   2640
tcttcttgag atccttttt  tctgcgcgta atctgctgct tgcaaacaaa aaaaccaccg   2700
ctaccagcgg tggtttgttt gccggatcaa gagctaccaa ctcttttcc  gaaggtaact   2760 ggcttcagca gagcgcagat accaaatact gtccttctag tgtagccgta gttaggccac   2820
cacttcaaga actctgtagc accgcctaca tacctcgctc tgctaatcct gttaccagtg   2880
gctgctgcca gtggcgataa gtcgtgtctt accgggttgg actcaagacg atagttaccg   2940
gataaggcgc agcggtcggg ctgaacgggg ggttcgtgca acacagccag cttggagcga   3000
acgacctaca ccgaactgag atacctacag cgtgagcatt gagaaagcgc cacgcttccc   3060
gaagggagaa aggcggacag gtatccggta agcggcaggg tcggaacagg agagcgcacg   3120
agggagcttc caggggaaa  cgcctggtat ctttatagtc ctgtcgggtt tcgccacctc   3180
```

```
tgacttgagc gtcgattttt gtgatgctcg tcaggggggc ggagcctatg gaaaaacgcc   3240
agcaacgcgg cctttttacg gttcctggcc ttttgctggc cttttgctca catgttcttt   3300
cctgcgttat cccctgattc tgtggataac cgtattaccg cctttgagtg agctgatacc   3360
gctcgccgca gccgaacgac cgagcgcagc gagtcagtga gcgaggaagc ggaagagcgc   3420
ccaatacgca aaccgcctct ccccgcgcgt tggccgattc attaatgcag agatctttgg   3480
ccactccctc tctgcgcgct cgctcgctca ctgaggccgg gcgaccaaag gtcgcccgac   3540
gcccgggctt tgcccgggcg gcctcagtga gcgagcgagc gcgcagagag ggagtggcca   3600
actccatcac taggggttcc tggaggggtg gagtcgtgac gtgaattacg tcatagggtt   3660
agggaggtcc tggatcgatc cagacatgat aagatacatt gatgagtttg gacaaaccac   3720
aactagaatg cagtgaaaaa aatgctttat ttgtgaaatt tgtgatgcta ttgctttatt   3780
tgtaaccatt ataagctgca ataaacaagt taacaacaac aattgcattc attttatgtt   3840
tcaggttcag ggggaggtgt gggaggtttt ttaaagcaag taaaacctct acaaatgtgg   3900 tatgctgat tatgatctct agtcaaggca ctatacatca aatattcctt attacccct   3960 ttacaaatta aaaagctaaa ggtacacaat ttttgagcat agttattaat agcagacact   4020
ctatgcctgt gtggagtaag aaaaaacagt atgttatgat tataactgtt atgcctactt   4080
ataaaggtta cagaatattt ttccataatt ttcttgtata gcagtgcagc ttttccttt   4140 gtggtgtaaa tagcaaagca agcaagagtt ctattactaa acacagcatg actcaaaaaa   4200
cttagcaatt ctgaaggaaa gtccttgggg tcttctacct ttctcttctt ttttggagga   4260
gtagaatgtt gagagtcagc agtagcctca tcatcactag atggcatttc ttctgagcaa   4320
aacaggtttt cctcattaaa ggcattccac cactgctccc attcatcagt tccataggtt   4380
ggaatctaaa atacacaaac aattagaatc agtagtttaa cacattatac acttaaaaat   4440
tttatattta ccttagagct ttaaatctct gtaggtagtt tgtccaatta tgtcacacca   4500
cagaagtaag gttccttcac aaagatccgg gaccaaagcg gccatcgtgc ctccccactc   4560
ctgcagttcg ggggcatgga tgcgcggata gccgctgctg gtttcctgga tgccgacgga   4620
tttgcactgc cggtagaact ccgcgaggtc gtccagcctc aggcagcagc tgaaccaact   4680
cgcgagggga tcgagcccgg ggtgggcgaa gaactccagc atgagatccc cgcgctggag   4740
gatcatccag ccggcgtccc ggaaaacgat tccgaagccc aaccttcat agaaggcggc   4800 ggtggaatcg aaatctcgtg atggcaggtt gggcgtcgct tggtcggtca tttcgaaccc   4860
cagagtcccg ctcagaagaa ctcgtcaaga aggcgataga aggcgatgcg ctgcgaatcg   4920
ggagcggcga taccgtaaag cacgaggaag cggtcagccc attcgccgcc aagctcttca   4980
gcaatatcac gggtagccaa cgctatgtcc tgatagcggt ccgccacacc cagccggcca   5040
cagtcgatga atccagaaaa gcggccattt tccaccatga tattcggcaa gcaggcatcg   5100
ccatgggtca cgacgagatc ctcgccgtcg gcatgcgcg ccttgagcct ggcgaacagt   5160
tcggctggcg cgagcccctg atgctcttgt ccagatcatc ctgatcgaca agaccggctt   5220
ccatccgagt acgtgctcgc tcgatgcgat gttcgcttgg tggtcgaatg ggcaggtagc   5280
cggatcaagc gtatgcagcc gccgcattgc atcagccatg atggatactt tctcggcagg   5340
agcaaggtga gatgacagga gatcctgccc cggcacttcg cccaatagca gccagtccct   5400
tcccgcttca gtgacaacgt cgagcacagc tgcgcaagga acgcccgtcg tggccagcca   5460
cgatagccgc gctgcctcgt cctgcagttc attcagggca ccggacaggt cggtcttgac   5520
```

-continued

```
aaaaagaacc gggcgcccct gcgctgacag ccggaacacg gcggcatcag agcagccgat    5580
tgtctgttgt gcccagtcat agccgaatag cctctccacc caagcggccg gagaacctgc    5640
gtgcaatcca tcttgttcaa tcatgcgaaa cgatcctcat cctgtctctt gatcagatct    5700
tgatcccctg cgccatcaga tccttggcgg caagaaagcc atccagttta ctttgcaggg    5760
cttcccaacc ttaccagagg gcgcccagc tggcaattcc ggttcgcttg ctgtccataa    5820
aaccgcccag tctagctatc ggcatgtaag cccactgcaa gctacctgct ttctctttgc    5880
gcttgcgttt tcccttgtcc agatagccca gtagctgaca ttcatccggg gtcagcaccg    5940
tttctgcgga ctggctttct acgtgttccg cttcctttag cagcccttgc gccctgagtg    6000
cttgcggcag cgtgaagctt tttgcaaaag cctaggcctc caaaaaagcc tcctcactac    6060
ttctggaata gctcagaggc cgaggcggcc tcggcctctg cataaataaa aaaaattagt    6120
cagccatggg gcggagaatg ggcggaactg ggcggagtta ggggcgggat gggcggagtt    6180
aggggcggga ctatggttgc tgactaattg agatgcatgc tttgcatact tctgcctgct    6240
ggggagcctg gggactttcc acacctggtt gctgactaat tgagatgcat gctttgcata    6300
cttctgcctg ctggggagcc tggggacttt ccacacccta actgacacac attccaca    6358
```

RNA MOLECULES, METHODS OF PRODUCING CIRCULAR RNA, AND TREATMENT METHODS

This application is a national stage application under 35 U.S.C. § 371 of PCT Application No. PCT/US2018/039182, filed Jun. 23, 2018, which claims the priority benefit of U.S. Provisional Patent Application Ser. No. 62/524,189, filed Jun. 23, 2017, which are hereby incorporated by reference in their entirety.

This invention was made with government support under R01 NS064516 and F31AI134100 awarded by the National Institutes of Health. The government has certain rights in the invention.

FIELD OF THE INVENTION

The present invention relates to RNA molecules, vectors, cells, methods of producing circular RNA, and treatment methods.

BACKGROUND OF THE INVENTION

Small interfering RNAs ("siRNAs"), guide RNAs ("gRNAs"), and RNA aptamers are three major types of small RNAs that can be genetically encoded and expressed within cells to modulate intracellular processes. siRNA and gRNAs are primarily used to knockdown or knockout gene expression, respectively. In contrast, RNA aptamers, which are typically 50-150 nucleotides long and can bind diverse intracellular molecules (Connell et al., "Three Small Riboo-ligonucleotides with Specific Arginine Sites," *Biochemistry* 32:5497-5502 (1993); Sassanfar et al., "An RNA Motif that Binds ATP," *Nature* 364:550-553 (1993); Lauhon et al., "RNA Aptamers that Bind Flavin and Nicotinamide Redox Cofactors," *J. Am. Chem. Soc.* 117:1246-1257 (1995); and Mannironi et al., "In Vitro Selection of Dopamine RNA Ligands," *Biochemistry* 36:9726-9734 (1997)), can exhibit more targeted and precise effects (Ellington et al., "In Vitro Selection of RNA Molecules that Bind Specific Ligands," *Nature* 346:818-22 (1990) and Jenison et al., "High-Resolution Molecular Discrimination by RNA," *Science* 263:1425-1429 (1994)). For example, aptamers can bind specific domains in proteins and thereby modulate only one aspect of protein function, rather than deplete the expression of the entire protein (Rentmeister et al., "RNA Aptamers Selectively Modulate Protein Recruitment to the Cytoplasmic Domain of β-secretase BACE1 In Vitro," *RNA* 12:1650-1660 (2006)). Despite the powerful ability of aptamers to selectively modulate cellular functions, RNA aptamers have not achieved the same level of widespread use as siRNAs or gRNAs.

One major problem with expressing aptamers is that they do not achieve high enough concentrations to modulate proteins, which are typically expressed at much higher concentrations. Recent studies have characterized the half-life and intracellular concentrations of RNA aptamers expressed in HEK293T cells (Filonov et al., "In-Gel Imaging of RNA Processing Using Broccoli Reveals Optimal Aptamer Expression Strategies," *Chem. Biol.* 22:649-660 (2015). These studies show half-lives ranging from 30 minutes to 1.25 hours for RNA aptamers, and intracellular concentrations typically lower than 40 nM (Filonov et al., "In-Gel Imaging of RNA Processing Using Broccoli Reveals Optimal Aptamer Expression Strategies," *Chem. Biol.* 22:649-660 (2015) and Paige et al., "RNA Mimics of Green Fluorescent Protein," *Science* 333:642-646 (2011)). RNA aptamer instability contrasts with siRNA and miRNAs, which are relatively stable and accumulate to high concentrations. miRNAs are below the size threshold of RNA exonucleases (Rüegger et al., "MicroRNA Turnover: When, How, and Why," *Trends Biochem. Sci.* 37:436-446 (2012), allowing them to accumulate to high levels in cells.

The low cellular concentration of RNA aptamers limits their usefulness for modulating protein function. In order to effectively modulate proteins, the aptamer needs to bind all copies of a protein in the cell. However, proteins are often present at concentrations greater than 100 nM, and in many cases above 1 µM in cells (Dittmer et al., "Genetically Encoded Sensors to Elucidate Spatial Distribution of Cellular Zinc," *J. Biol. Chem.* 284:16289-16297 (2009)). Therefore, nanomolar aptamer concentrations are too low to stoichiometrically bind target proteins.

RNA degradation also prevents the use of RNA devices such as genetically encoded RNA-based sensors in mammalian cells. RNA-based biosensors that can detect diverse metabolites in bacteria have been previously reported (Paige et al., "Fluorescence Imaging of Cellular Metabolites With RNA," *Science* 335:1194 (2012)). These sensors are a single RNA sequence that comprises a fluorogenic RNA aptamer such as Spinach, and an aptamer that binds a metabolite (Paige et al., "Fluorescence Imaging of Cellular Metabolites With RNA," *Science* 335:1194 (2012)). The metabolite-binding aptamers are incorporated in such a way that Spinach is unfolded until the RNA device encounters the metabolite. The metabolite binds, triggering folding of its cognate aptamer, which then promotes the folding of the Spinach aptamer. Spinach then binds and activates the fluorescence of its GFP-like fluorophore, 3,5-difluoro-hydroxybenzylidene imidazolinone ("DFHBI"). These biosensors have enabled fluorescence imaging of diverse metabolites and signaling molecules in living bacterial cells (Paige et al., "Fluorescence Imaging of Cellular Metabolites With RNA," *Science* 335:1194 (2012); Kellenberger et al., "RNA-Based Fluorescent Biosensors for Live Cell Imaging of Second Messengers Cyclic di-GMP and Cyclic AMP-GMP," *J. Am. Chem. Soc.* 135:4906-4909 (2013); and You et al., "Imaging Metabolite Dynamics in Living Cells Using a Spinach-Based Riboswitch," *Proc. Natl. Acad. Sci. U.S.A* 112:E2756-2765 (2015)).

Although these biosensors have been expressed and used in bacterial cells, they have not been suitable for use in mammalian cells. Unlike bacterial cells where these RNAs accumulate to micromolar concentrations (Paige et al., "Fluorescence Imaging of Cellular Metabolites With RNA," *Science* 335:1194 (2012)), in part because RNA polymers may be highly expressed in these cells, and in part because they may be more stable in bacteria, in mammalian cells they are expressed at nanomolar concentrations resulting in insufficient fluorescent signals for detection (Filonov et al., "In-Gel Imaging of RNA Processing Using Broccoli Reveals Optimal Aptamer Expression Strategies," *Chem. Biol.* 22:649-660 (2015)). In contrast, conventional protein-based FRET biosensors for metabolite imaging in mammalian cells are typically expressed at µM concentrations (Dittmer et al., "Genetically Encoded Sensors to Elucidate Spatial Distribution of Cellular Zinc," *J. Biol. Chem.* 284:16289-16297 (2009)). Although heterologously expressed RNAs are generally short-lived and do not accumulate to high levels in mammalian cells, the general lack of accumulation of RNAs is a problem in some cell types, including plant cells, yeast, bacteria, archaea, insect cells, and others. Thus, in order to use or express aptamers, small RNA sequences, and RNA-based biosensors for metabolite detection, RNA sequences that encode peptides, or any other RNA sequence that might influence cellular function, new methods to achieve markedly higher expression levels are needed for mammalian and other cells.

Various groups have described improved eukaryotic expression by making circular RNA lacking 5' or 3' ends. Such RNA molecules are resistant to eukaryotic exoribonucleases and are therefore degraded more slowly by cellular machinery. For example, Lu et al., "Metazoan tRNA Introns Generate Stable Circular RNAs In Vivo," *RNA* 21:1554-1565 (2015) ("Lu") describes the discovery of tRNA intronic circular (tric)RNAs in metazoans as a byproduct of tRNA splicing pathways and demonstrates that the sequence of such intronic circular RNAs can be modified to contain exogenous sequences, including RNA aptamers. U.S. Pat. No. 6,210,931 to Feldstein et al. describes a method for synthesizing circular RNAs in vitro using a hairpin ribozyme along with sequences from the satellite ringspot virus(-) RNA. U.S. Patent Application Publication No. 2010/0137407 to Abe et al. describes that single-chain circular RNA molecules may be produced using a sense and antisense RNA synthesized and ligated together to form a circular RNA. They also describe that this circular RNA can cause an RNA interference effect. U.S. Pat. No. 5,773,244 to Ares, Jr. et al. describes methods of synthesizing circular RNA in vitro, as the expression of circular RNA in bacteria and yeast using RNA cyclase ribozymes derived from a group I intron of phage T4. However, new systems for generating circular RNAs are needed that can be expressed in virtually any metazoan or bacterial cell.

The present invention is directed to overcoming these and other deficiencies in the art.

SUMMARY OF THE INVENTION

One aspect of the present invention relates to an RNA molecule comprising a first ribozyme, a first ligation sequence, an effector molecule, a second ligation sequence, and a second ribozyme. Vectors and cells comprising the RNA molecule of the present application are also disclosed.

Another aspect of the present invention relates to a method of producing a circular RNA molecule. This method involves providing one or more vectors comprising a nucleic acid sequence encoding a 5' polymerase promoter sequence, a nucleic acid sequence encoding a first ribozyme, a nucleic acid sequence encoding a first ligation sequence, a nucleic acid sequence encoding an effector molecule, a nucleic acid sequence encoding a second ligation sequence, a nucleic acid sequence encoding a second ribozyme, and a nucleic acid sequence encoding a 3' polymerase terminator sequence. The method further involves transcribing the one or more vectors to produce one or more linear RNA molecules and contacting the one or more linear RNA molecules with an RNA ligase to form a circular RNA molecule.

A further aspect of the present invention relates to a treatment method. This treatment method involves contacting a cell with an RNA molecule of the present invention under conditions effective to express the effector molecule to treat the cell.

In another aspect, the present invention relates to a treatment method that involves contacting a cell with a vector according to the present invention under conditions effective to express the effector molecule to treat the cell.

In a further aspect, the present invention relates to an RNA molecule comprising a 5'-OH end and a 2',3'-cyclic phosphate end, where the RNA molecule further comprises an effector molecule between the 5'-OH and the 2',3'-cyclic phosphate ends.

Described infra is a novel system for generating circular RNAs in virtually any metazoan or bacterial cell. In one embodiment, this may be done without the co-expression of any additional proteins or enzyme. This expression system takes advantage of the nearly ubiquitous endogenous RNA ligase, RtcB, and enzymes with related functions, which ligate unique RNA ends that are not normally present in RNA. More specifically, expressed RNAs are designed to contain specific and highly efficient ribozyme sequences at the 5' and 3' end of the RNA. These ribozymes autocatalytically process the transcript, resulting in ends that are substrates for RNA-ligation by RtcB. This expression strategy can achieve circular RNA expression that matches or exceeds the most highly expressed RNAs in cells such as tRNAs and snRNAs. Using this approach, protein-binding RNA aptamers that otherwise have minimal effects in cells become markedly potent effector molecules. Additionally, RNA-based metabolite sensors that have previously only been used in bacteria can be expressed at high levels and used in mammalian cells when circularized. Thus, the Examples of the present application demonstrate a strategy for high-level expression using autocatalytic RNAs that markedly enhances the ability of RNA aptamers and devices to be used in mammalian cells.

BRIEF DESCRIPTION OF THE DRAWINGS

FIG. 1A shows the endogenous processing of the tRNA intronic circular RNA system (tricY). tRNA splicing endonuclease ("TSEN") cleaves both strands of a stem in the transcribed pri-tricRNA, containing the tRNA exon (black) and tRNA intron (grey). Each cleaved 5' end has a 5'-hydroxyl modification and each 3' end has a 2',3'-cyclic phosphate modification. The stems containing both modifications in proximity are substrates for the endogenous RNA ligase, RtcB, the activity of which creates new stem loops on both RNAs. The exon forms a mature tRNA, while the intron forms a circular RNA. FIG. 1B shows that expressing Broccoli within the unprocessed tRNA generates circular Broccoli. When Broccoli is encoded in the intron of the tRNA, the linear and circular species can be identified by its instability or stability to 6 hours of Actinomycin D ("ActD") treatment, respectively. Linear RNAs are degraded while circular RNAs are stable. Encoding Broccoli on the exon of a tRNA that has been circularly permuted so that the 5' and 3' ends are inside the intron rather than at the ends of the exon ("cp-tRNA") generates circular RNA more abundantly than tricY. This construct also generates an abundant linear Broccoli species. Minimizing the tRNA sequence to contain only the processed stem ("tRNA-end") does not generate circular RNA.

FIGS. 4A-4G relate to a self-processed circRNA mammalian expression vector. FIG. 4A is an illustration showing a construct design for autocatalytically processed circRNA expression. Self-cleaving ribozymes flank the ends of the circularized insert that contains an RNA aptamer sequence. The ligation sequences, which remain on either side after cleavage, contain a phosphorylation state and RNA termini modification state that is recognized by an endogenous RNA ligase and circularized. Circular RNAs resist endogenous exoribonucleases, allowing the RNA aptamer to reach exceptionally high concentrations. FIG. 4B shows that ribozymes efficiently self-cleave during transcription reactions. To determine if a construct design as shown in FIG. 4A interferes with ribozyme cleavage, DNA templates of the construct were transcribed to observe efficient cleavage. The construct containing Twister P1 and Twister P3 U7A ribozymes was transcribed in vitro and quenched with urea before running on denaturing PAGE and visualizing RNA. Fully cleaved products and the side products of cleavage accumulate efficiently and rapidly after transcription. FIG. 4C shows fully-cleaved products of transcription in vitro contain appropriate ends for circularization by the endogenous ligase, RtcB. Whether ribozyme-cleaved constructs contain the expected phosphorylation pattern and whether the fully-cleaved product in FIG. 4B is able to be ligated by RtcB was examined. The fully-cleaved RNA from FIG. 4B was excised and RtcB ligation reactions were performed or the RNA was first changed to have an incompatible phosphorylation pattern first using T4 polynucleotide kinase ("T4 PNK"). The fully-cleaved RNA demonstrates a shift in gel mobility that is not observed without ligation or with T4 PNK treatment. This shift in gel mobility suggests that the fully-cleaved RNA contains the appropriate ends for ligation. FIG. 4D shows a construct containing Twister P1 and Twister P3 U7A expresses significantly more highly stable RNA than a previous circRNA expressing system. Versions of this construct containing a variety of 5' and 3' ribozymes were compared to the tricY system and the stability of the expressed bands was tested. Constructs contain a fluorogenic RNA aptamer (Broccoli) circularized insert for in-gel visualization, and cells were treated with actinomycin D for 6 hours to observe stability of the RNA to degradation. The Twister-twister containing construct, Tornado, expressed significantly more stable Broccoli than the tricY system and other versions of this construct that use other ribozymes. The high stability of this Tornado-expressed band is characteristic of circRNA. FIG. 4E shows the highly stable Tornado-expressed RNA is resistant to exoribonucleases. While circular RNA cannot be degraded by RNase R, since they lack 5' and 3' ends, most linear RNA are susceptible to this exoribonuclease. Tornado-expressed RNA was excised from FIG. 4D and subjected to RNase R treatment. RNase R does not degrade this highly stable RNA compared untreated sample, suggesting that this RNA contains no 5' or 3' ends. FIG. 4F shows Tornado-expressed RNA is circular RNA. Whether highly stable Tornado-expressed RNA is definitively circular or linear was tested by site-specific cleavage, which produces one or two RNA species respectively. DNA-probes directed RNAse H cleavage of the unstructured region of an RNA (A162) that was either expressed by Tornado or transcribed in vitro. Site-specific cleavage of the linear transcript produces two bands, each of expected size given the transcript length and probe site, while the Tornado-expressed RNA produces a single band similar in size to the uncleaved transcribed sample. FIG. 4G is a schematic diagram showing that the internal cleavage of linear RNAs leads to two RNA species while that of circular RNAs merely converts the RNA back to a linear species, indicating that Tornado-expressed RNA in FIG. 4F is indeed circular RNA.

FIG. 6A shows that Tornado-expressed circular Broccoli is highly abundant. Levels of circular RNA expressed by Tornado were compared with that of other circular RNA expression systems and with abundant endogenous RNAs. HEK239T cells were transfected with plasmids encoding Broccoli in Tornado, in other circular RNA expressing systems, and in a linear context. Broccoli-containing RNAs and total RNA were observed in each sample using DFHBI-1T and SYBR Gold stains, respectively. Circular Broccoli bands were significantly stronger from Tornado than from all other circular RNA expression systems and produce a band that is detected by SYBR Gold to be as abundant as 5.8S, 5S, and tRNA bands. This suggests that circular RNAs expressed by Tornado reach an average concentration in cells in the µM range. FIG. 6B shows that Broccoli detection by microscopy is significantly improved by expression in Tornado. Whether Tornado improved the detection of Broccoli by microscopy was determined, and Broccoli fluorescence was observed in individual cells. Indicated HEK293T cells (arrows) were quantified for total cell fluorescence. Tornado-expressed circular Broccoli signal is roughly 50-fold higher than the tricRNA system and 100 fold than by expression of linear Broccoli. This suggests that the Tornado expression system markedly improves the signal of fluorogenic RNA aptamers in vivo. FIG. 6C shows that Tornado efficiently circularizes an RNA aptamer in a variety of cell lines. The level to which Tornado-expressed circular Broccoli reaches in cell lines other than HEK293T by plasmid transfection was evaluated. Three days after transfection with plasmids encoding linear Broccoli or circular Broccoli with the tricY system or Tornado system (tricY-Broccoli, or Tornado-Broccoli plasmids, respectively), cells (HepG2, HeLa, and COS-7) were imaged by fluorescence microscopy with DFHBI-1T. In all cell types observed, none or minimal green fluorescence is detected when Broccoli is expressed in the linear form or by the tricY system, and readily detected when expressed by Tornado. FIG. 6D shows the quantification of Tornado-expressed circular RNA concentration in transfected cells. The average intracellular concentration of circular Broccoli in several cell types was measured by loading total RNA along known quantities of circular Broccoli. Three days after transfection with a Broccoli-encoded Tornado (Tornado-Broccoli), HepG2, HeLa, and HEK293T cells were counted and their total RNAs were harvested and then loaded on gel with standards. Normalizing for transfection efficiency, intracellular circular Broccoli concentrations were estimated based on fluorescence band intensity. All cell lines contained μM levels of circular Broccoli; 3, 21, and 13 μM for HepG2, HeLa, and HEK293T cells, respectively. Additionally, total RNA that had been harvested from HEK293T cells two days after infection was loaded with a lentivirus containing the Tornado-Broccoli construct and an intracellular concentration of 300 nM was observed. FIG. 6E shows that Tornado efficiently circularizes a variety of fluorogenic RNA aptamers. Whether Tornado could efficiently circularize fluorogenic aptamers other than Broccoli was next examined. Plasmids containing Red Broccoli or tRNA-Corn using a linear promoter or using Tornado were transfected into HEK293T cells and imaged after three days using DFHO. Cellular fluorescence from Red Broccoli and tRNA-Corn was more easily detected when expressed as circular RNA by Tornado than when in a linear context.

FIG. 8A shows the design of bifunctional circular RNAs containing pathway-inhibiting aptamers. Circular RNAs are designed to contain a 3-way junction F30 (black) with Broccoli on arm 1, and an NF-κB aptamer on arm 2, while the circularizing stem forms at the base of the F30. This design allows for functional investigation of pathway-inhibiting aptamers while also probing for abundance of this circular RNA using Broccoli fluorescence. FIG. 8B shows that bifunctional circular RNAs are expressed in NF-κB luciferase reporter 293 cells. Whether Tornado can generate bifunctional circular RNAs with a more complex structure that contains Broccoli and one of a variety of NF-κB pathway inhibiting aptamers. Two days after transfection with each of these constructs, cells were treated with Actinomycin D, then total RNA was harvested, and in-gel Broccoli-fluorescent bands were observed. Each construct generated a single Broccoli-fluorescent band that was resistant to Actinomycin treatment, generating circRNAs to an estimated concentration of 5 μM in this cell type. Thus NF-κB luciferase reporter 293 cells can support Tornado expression of F30-containing bifunctional circular RNAs. FIG. 8C shows that Tornado improves inhibition of pathway activation by NF-κB aptamers. NF-κB activation levels were detected to demonstrate that activation inhibition by these aptamers is improved when they are expressed by Tornado, as compared to in a linear context. After transfection of luciferase reporter cells with bifunctional circular RNAs or treatment with a known pathway inhibitor, the pathway with IL-1β was activated and luciferase activity was detected. Activation-induced luminescence is 70% inhibited by all versions of the NF-κB aptamer, but only 15% inhibited by linear expression of one of these aptamers. Additionally, the transfected cells that showed green-fluorescence as a result of treatment of cells with DFHBI-1T, which binds and is fluorescently activated is the fluorogenic aptamer is present, were sorted prior to stimulation and luciferase activity assay to see if these cells would have a stronger inhibitory function. Indeed, inhibition of NF-κB pathway activation in green-fluorescent cells was as potent as chemical inhibition of the pathway in untransfected cells (FIG. 8D). Overall, these suggest that expressing a pathway-inhibiting aptamer using Tornado improves overall inhibition by several fold.

FIG. 9A shows the design of intracellular metabolite sensors from circular RNA. Sensors are designed with a transducer stem that is necessary for Broccoli fluorescence, but only folded when the SAM aptamer binds to its molecular target, S-adenosylmethionine. The circularizing stem is contained on the bottom end of Broccoli. This design is adapted from previously reported linear SAM sensors that function only in bacteria. FIG. 9B shows the in vitro optimization of SAM sensor's transducer stem for the SAM detection. To determine which transducer sequence would generate the highest signal/noise detection, the circular sensors Broccoli signals were assessed upon titration of SAM. After harvesting RNA from HEK293 Ts expressing sensor variants using Tornado, Broccoli-fluorescent bands were imaged with increasing concentrations of SAM in the staining solution. The minimal transducer stem (Transducer 1) produced the greatest signal/noise, indicating that it could function as a SAM sensor when expressed in mammalian cells. FIG. 9C shows the dynamic detection of intracellular SAM levels with the Tornado-expressed circRNA sensor. Whether the optimized circular RNA sensor for SAM could detect increases and decreases in intracellular SAM levels when expressed by Tornado was next investigated. After transfection of HEK293T cells with the circular-sensor- or circular-Broccoli-expressing construct, cells treated with cycloleucine to inhibit SAM biosynthesis and following withdrawal of cycloleucine were imaged. This circRNA sensor dynamically detects increases and decreases in intracellular SAM levels. FIG. 9D shows the quantification of SAM levels based on in vivo sensor fluorescence. Rates of changes in intracellular SAM levels can be observed in response to cycloleucine.

FIG. 10A is an illustration of RNAs that were cleaved by different Tornado expression systems (solid and dotted lines) becoming ligated intermolecularly to form trans-spliced circular RNAs. FIG. 10B is a detailed depiction of two RNA processed by two different Tornado systems leading to trans-spliced circular RNA. Constructs are cleaved by 5' and 3' ribozymes to generate 5'-OH and 2',3'-cyclic phosphate, respectively, on the cleaved RNA. Ligation sequences (orange for Stem 1 and pink for Stem 2) from different stems are not complementary, and thus will not act as RtcB substrates. Thus, by splitting each pair of ligation sequences across the two Tornado systems, trans-spliced circular RNAs were generated. The ligation sequences must be split such that after intermolecular base-pairing, the ligation sequences that are complementary are together at the end of each stem. FIG. 10C shows trans-splicing of split Broccoli RNAs into circular Broccoli. Cells were transfected or co-transfected with constructs as described with "+" or "−" and total RNA was loaded on a 10% PAGE denaturing gel and stained using DFHBI-1T. Tornado-based expression of full Broccoli generates similar levels of circular Broccoli, regardless of which of the two different complementary stems are use in the ligation sequences. When the 5' ligation sequence containing the sequence for one stem is combined with the 3' ligation sequence pertaining to the other stem and either strand A or strand B of Broccoli is an effector, there is predictably no Broccoli-containing circular RNA detected. However, when strand-A-containing constructs are co-transfected with a strand-B-containing construct, Broccoli fluorescence was observed only when the 5'- and 3'-tRNA exon stems are complementary after intermolecular base-pairing. Thus, Tornado-expressed RNAs can be designed to intermolecularly circularize rather than intramolecularly circularize.

DETAILED DESCRIPTION OF THE INVENTION

Figure 1A:
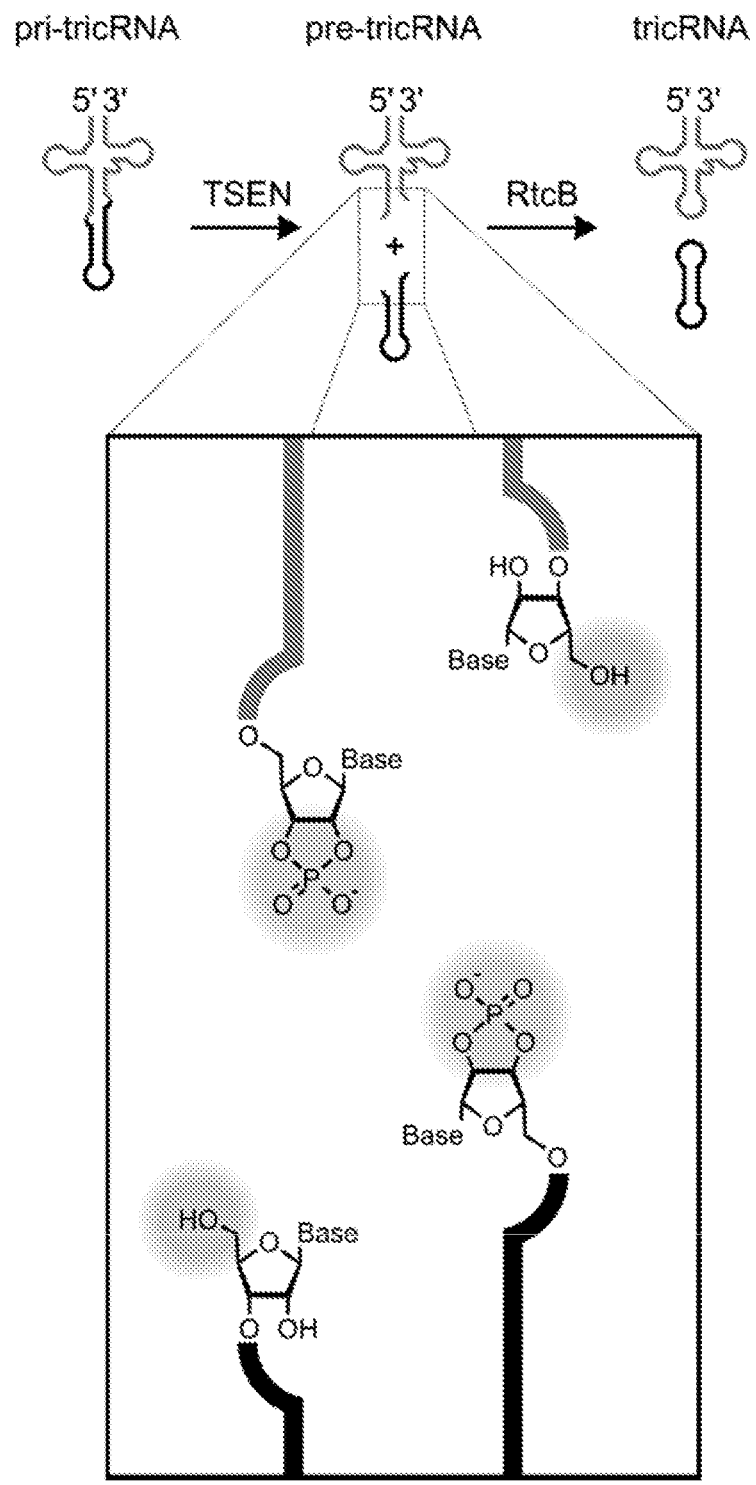
FIGS. 1A-1B are illustrations showing the processing of tRNA to generate tRNA intronic circular RNA and its use for expression of circular Broccoli.

One aspect of the present invention relates to an RNA molecule comprising a first ribozyme, a first ligation sequence, an effector molecule, a second ligation sequence, and a second ribozyme.

A person of ordinary skill in the art will readily recognize that there are many types of "RNA molecules." These include coding RNA (i.e., RNA that is translated into a protein, e.g., mRNA) and non-coding RNA. Other types of RNA include, without limitation, 7SK RNA, signal recognition particle RNA, antisense RNA, CRISPR RNA, guide RNA, long noncoding RNA, microRNA, messenger RNA, piwi-interacting RNA, repeat associated si RNA, retrotransposon RNA, ribonuclease P ribosomal RNA small cajal body-specific RNA, small interfering RNA, sm Y RNA, small nucleolar RNA, small nuclear RNA, trans-acting siRNA, telomerase RNA, transfer-messenger RNA, transfer RNA, viral response RNA, vault RNA, and Y RNA. The RNA molecule may have a modified base. As used herein, a "modified base" is, according to one embodiment, a ribonucleotide base of uracil, cytosine, adenine, or guanine that possesses a chemical modification from its normal structure. For example, one type of modified base is a methylated base, such as $N^6$-methyladenosine ($m^6A$). A modified base may also be a substituted base, meaning the base possesses a structural modification that renders it a chemical entity other than uracil, cytosine, adenine, or guanine. For example, pseudouridine is one type of substituted RNA base. Table 1 below provides a list of modified bases that may be present in the RNA molecule of the present invention.

TABLE 1

List of Base Modifications

| Abbreviation | Chemical name |
|---|---|
| $m^1acp^3Y$ | 1-methyl-3-(3-amino-3-carboxypropyl) pseudouridine |
| $m^1A$ | 1-methyladenosine |
| $m^1G$ | 1-methylguanosine |

TABLE 1-continued

List of Base Modifications

| Abbreviation | Chemical name |
|---|---|
| $m^1I$ | 1-methylinosine |
| $m^1Y$ | 1-methylpseudouridine |
| $m^1Am$ | 1,2'-O-dimethyladenosine |
| $m^1Gm$ | 1,2'-O-dimethylguanosine |
| $m^1Im$ | 1,2'-O-dimethylinosine |
| $m^2A$ | 2-methyladenosine |
| $ms^2io^6A$ | 2-methylthio-$N^6$-(cis-hydroxyisopentenyl) adenosine |
| $ms^2hn^6A$ | 2-methylthio-$N^6$-hydroxynorvalyl carbamoyladenosine |
| $ms^2i^6A$ | 2-methylthio-$N^6$-isopentenyladenosine |
| $ms^2m^6A$ | 2-methylthio-$N^6$-methyladenosine |
| $ms^2t^6A$ | 2-methylthio-$N^6$-threonyl carbamoyladenosine |
| $s^2Um$ | 2-thio-2'-O-methyluridine |
| $s^2C$ | 2-thiocytidine |
| $s^2U$ | 2-thiouridine |
| Am | 2'-O-methyladenosine |
| Cm | 2'-O-methylcytidine |
| Gm | 2'-O-methylguanosine |
| Im | 2'-O-methylinosine |
| Ym | 2'-O-methylpseudouridine |
| Um | 2'-O-methyluridine |
| Ar(P) | 2'-O-ribosyladenosine (phosphate) |
| Gr(p) | 2'-O-ribosylguanosine (phosphate) |
| $acp^3U$ | 3-(3-amino-3-carboxypropyl)uridine |
| $m^3C$ | 3-methylcytidine |
| $m^3Y$ | 3-methylpseudouridine |
| $m^3U$ | 3-methyluridine |
| $m^3Um$ | 3,2'-O-dimethyluridine |
| imG-14 | 4-demethylwyosine |
| $s^4U$ | 4-thiouridine |
| $chm^5U$ | 5-(carboxyhydroxymethyl)uridine |
| $mchm^5U$ | 5-(carboxyhydroxymethyl)uridine methyl ester |
| $inm^5s^2U$ | 5-(isopentenylaminomethyl)-2-thiouridine |
| $inm^5Um$ | 5-(isopentenylaminomethyl)-2'-O-methyluridine |
| $inm^5U$ | 5-(isopentenylaminomethyl)uridine |
| $nm^5s^2U$ | 5-aminomethyl-2-thiouridine |
| $ncm^5Um$ | 5-carbamoylmethyl-2'-O-methyluridine |
| $ncm^5U$ | 5-carbamoylmethyluridine |
| $cmnm^5Um$ | 5-carboxymethylaminomethyl-2'-O-methyluridine |
| $cmnm^5s^2U$ | 5-carboxymethylaminomethyl-2-thiouridine |
| $cmnm^5U$ | 5-carboxymethylaminomethyluridine |
| $cm^5U$ | 5-carboxymethyluridine |
| $f^5Cm$ | 5-formyl-2'-O-methylcytidine |
| $f^5C$ | 5-formylcytidine |
| $hm^5C$ | 5-hydroxymethylcytidine |
| $ho^5U$ | 5-hydroxyuridine |
| $mcm^5s^2U$ | 5-methoxycarbonylmethyl-2-thiouridine |
| $mcm^5Um$ | 5-methoxycarbonylmethyl-2'-O-methyluridine |
| $mcm^5U$ | 5-methoxycarbonylmethyluridine |
| $mo^5U$ | 5-methoxyuridine |
| $m^5s^2U$ | 5-methyl-2-thiouridine |
| $mnm^5se^2U$ | 5-methylaminomethyl-2-selenouridine |
| $mnm^5s^2U$ | 5-methylaminomethyl-2-thiouridine |
| $mnm^5U$ | 5-methylaminomethyluridine |
| $m^5C$ | 5-methylcytidine |
| $m^5D$ | 5-methyldihydrouridine |
| $m^5U$ | 5-methyluridine |
| $tm^5s^2U$ | 5-taurinomethyl-2-thiouridine |
| $tm^5U$ | 5-taurinomethyluridine |
| $m^5Cm$ | 5,2'-O-dimethylcytidine |
| $m^5Um$ | 5,2'-O-dimethyluridine |
| $preQ_1$ | 7-aminomethyl-7-deazaguanosine |
| $preQ_0$ | 7-cyano-7-deazaguanosine |
| $m^7G$ | 7-methylguanosine |
| $G^+$ | archaeosine |
| D | dihydrouridine |
| oQ | epoxyqueuosine |
| galQ | galactosyl-queuosine |
| OHyW | hydroxywybutosine |
| I | inosine |
| imG2 | isowyosine |
| $k^2C$ | lysidine |
| manQ | mannosyl-queuosine |
| mimG | methylwyosine |
| $m^2G$ | $N^2$-methylguanosine |
| $m^2Gm$ | $N^2$,2'-O-dimethylguanosine |
| $m^{2,7}G$ | $N^2$,7-dimethylguanosine |

TABLE 1-continued

List of Base Modifications

| Abbreviation | Chemical name |
| --- | --- |
| $m^{2,7}Gm$ | $N^2,7,2'$-O-trimethylguanosine |
| $m^2_2G$ | $N^2,N^2$-dimethylguanosine |
| $m^2_2Gm$ | $N^2,N^2,2'$-O-trimethylguanosine |
| $m^{2,2,7}G$ | $N^2,N^2,7$-trimethylguanosine |
| $ac^4Cm$ | $N^4$-acetyl-2'-O-methylcytidine |
| $ac^4C$ | $N^4$-acetylcytidine |
| $m^4C$ | $N^4$-methylcytidine |
| $m^4Cm$ | $N^4,2'$-O-dimethylcytidine |
| $m^4_2Cm$ | $N^4,N^4,2'$-O-trimethylcytidine |
| $io^6A$ | $N^6$-(cis-hydroxyisopentenyl)adenosine |
| $ac^6A$ | $N^6$-acetyladenosine |
| $g^6A$ | $N^6$-glycinylcarbamoyladenosine |
| $hn^6A$ | $N^6$-hydroxynorvalylcarbamoyladenosine |
| $i^6A$ | $N^6$-isopentenyladenosine |
| $m^6t^6A$ | $N^6$-methyl-$N^6$-threonylcarbamoyladenosine |
| $m^6A$ | $N^6$-methyladenosine |
| $t^6A$ | $N^6$-threonylcarbamoyladenosine |
| $m^6Am$ | $N^6,2'$-O-dimethyladenosine |
| $m^6_2A$ | $N^6,N^6$-dimethyladenosine |
| $m^6_2Am$ | $N^6,N^6,2'$-O-trimethyladenosine |
| $o_2yW$ | peroxywybutosine |
| Y | pseudouridine |
| Q | queuosine |
| OHyW | undermodified hydroxywybutosine |
| $cmo^5U$ | uridine 5-oxyacetic acid |
| $mcmo^5U$ | uridine 5-oxyacetic acid methyl ester |
| yW | wybutosine |
| imG | wyosine |

RNA molecules of the present invention also include PNAs and phosphorthioate or nucleic acids with other backbones.

As used herein, the term "ribozyme" refers to an RNA sequence that hybridizes to a complementary sequence in a substrate RNA and cleaves the substrate RNA in a sequence specific manner at a substrate cleavage site. Typically, a ribozyme contains a catalytic region flanked by two binding regions. The ribozyme binding regions hybridize to the substrate RNA, while the catalytic region cleaves the substrate RNA at a substrate cleavage site to yield a cleaved RNA product. The nucleotide sequence of the ribozyme binding regions may be completely complementary or partially complementary to the substrate RNA sequence with which the ribozyme hybridizes.

In one embodiment, each of the first ribozyme and the second ribozyme comprise a sequence that may be cleaved to produce a 5'-OH end and a 2',3'-cyclic phosphate end. In accordance with this embodiment, each of the first ribozyme and the second ribozyme is a self-cleaving ribozyme. Self-cleaving ribozymes are known in the art and are characterized by distinct active site architectures and divergent, but similar, biochemical properties. The cleavage activities of self-cleaving ribozymes are highly dependent upon divalent cations, pH, and base-specific mutations, which can cause changes in the nucleotide arrangement and/or electrostatic potential around the cleavage site (see, e.g., Weinberg et al., "New Classes of Self-Cleaving Ribozymes Revealed by Comparative Genomics Analysis," *Nat. Chem. Biol.* 11(8): 606-610 (2015) and Lee et al., "Structural and Biochemical Properties of Novel Self-Cleaving Ribozymes," *Molecules* 22(4):E678 (2017), which are hereby incorporated by reference in their entirety).

Suitable self-cleaving ribozymes include, but are not limited to, Hammerhead, Hairpin, Hepatitis Delta Virus ("HDV"), *Neurospora* Varkud Satellite ("VS"), Vg1, glucosamine-6-phosphate synthase(glmS), Twister, Twister Sister, Hatchet, Pistol, and engineered synthetic ribozymes, and derivatives thereof (see, e.g., Harris et al., "Biochemical Analysis of Pistol Self-Cleaving Ribozymes," *RNA* 21(11): 1852-8 (2015), which is hereby incorporated by reference in its entirety).

Twister ribozymes comprise three essential stems (P1, P2, and P4), with up to three additional ones (P0, P3, and P5) of optional occurrence. Three different types of Twister ribozymes have been identified depending on whether the termini are located within stem P1 (type P1), stem P3 (type P3), or stem P5 (type P5) (see, e.g., Roth et al., "A Widespread Self-Cleaving Ribozyme Class is Revealed by Bioinformatics," *Nature Chem. Biol.* 10(1):56-60 (2014)). The fold of the Twister ribozyme is predicted to comprise two pseudoknots (T1 and T2, respectively), formed by two long-range tertiary interactions (see Gebetsberger et al., "Unwinding the Twister Ribozyme: from Structure to Mechanism," *WIREs RNA* 8(3):e1402 (2017), which is hereby incorporated by reference in its entirety).

Twister Sister ribozymes are similar in sequence and secondary structure to Twister ribozymes. In particular, some Twister RNAs have P1 through P5 stems in an arrangement similar to Twister Sister and similarities in the nucleotides in the P4 terminal loop exist. However, these two ribozyme classes cleave at different sites, Twister Sister ribozymes do not appear to form pseudoknots via Watson-Crick base pairing (which occurs in all known twister ribozymes), and there is poor correspondence among many of the most highly conserved nucleotides in each of these two motifs (see Weinberg et al., "New Classes of Self-Cleaving Ribozymes Revealed by Comparative Genomics Analysis," *Nat. Chem. Biol.* 11(8):606-610 (2015), which is hereby incorporated by reference in its entirety).

Pistol ribozymes are characterized by three stems: P1, P2, and P3, as well as a hairpin and internal loops. A six-base-pair pseudoknot helix is formed by two complementary regions located on the P1 loop and the junction connecting P2 and P3; the pseudoknot duplex is spatially situated between stems P1 and P3 (Lee et al., "Structural and Biochemical Properties of Novel Self-Cleaving Ribozymes," *Molecules* 22(4):E678 (2017), which is hereby incorporated by reference in its entirety).

Hammerhead ribozymes are composed of structural elements including three helices, referred to as stem I, stem II, and stem III, and joined at a central core of 11-12 single strand nucleotides. Hammerhead ribozymes may also contain loop structures extending from some or all of the helices. These loops are numbered according to the stem from which they extend (e.g., loop I, loop II, and loop III).

In one embodiment, the first ribozyme is a Twister ribozyme or a Twister Sister ribozyme. For example, the first ribozyme may be a P3 Twister ribozyme.

In another embodiment, the second ribozyme is a Twister, Twister Sister, or Pistol Ribozyme. For example, the second ribozyme may be a P1 Twister ribozyme.

In one embodiment, the first ribozyme is a P3 Twister ribozyme and the second ribozyme is a P1 Twister ribozyme.

The ribozymes of the present invention include naturally-occurring (wildtype) ribozymes and modified ribozymes, e.g., ribozymes containing one or more modifications, which can be addition, deletion, substitution, and/or alteration of at least one (or more) nucleotide. Such modifications may result in the addition of structural elements (e.g., a loop or stem), lengthening or shortening of an existing stem or loop, changes in the composition or structure of a loop(s) or a stem(s), or any combination of these. As described herein, modification of the nucleotide sequence of naturally occurring self-cleaving ribozymes (e.g., a P3 Twister ribozyme)

can increase or decrease the ability of a ribozyme to autocatalytically cleave its RNA. In one embodiment, each of the first and the second ribozyme is, independently, modified to comprise a non-natural or modified nucleotide. In some embodiments, each of the first and the second ribozyme is modified to comprise pseudouridine in place of uridine.

In another embodiment, each of the first and the second ribozyme is, independently, a split ribozyme or ligand-activated ribozyme derivative.

As used herein, the phrase "ligation sequence" refers to a sequence complementary to another sequence, which enables the formation of Watson-Crick base pairing to form suitable substrates for ligation by a ligase, e.g., an RNA ligase. In one embodiment, each of the first ligation sequence and the second ligation sequence comprise a portion of a tRNA exon sequence or derivative thereof. The first ligation sequence and the second ligation sequence may each, independently, comprise at least 1, 2, 3, 4, 5, 6, 7, 8, 9, 10, 11, or 12 additional nucleotides to promote base-pairing with each other.

In one embodiment, the first ligation sequence and the second ligation sequence are substrates for an RNA ligase. According to one embodiment, the RNA ligase is RtcB. RtcB is not present in all lower organisms, but molecules with similar activities are present. In other words, there are molecules that ligate ends similar to the ligation activity of RtcB. RtcB (or other functionally similar molecules) may be overexpressed to maximize circular RNA expression according to the present invention.

The purpose of the ligation sequence is to assist in circularization of the RNA molecule, to protect the RNA molecule from degradation and, therefore, ultimately enhance expression of the effector molecule. While it is thought that the RNA molecule of the present invention could circularize without the ligation sequences, and such an invention is hereby contemplated, the ligation sequences are also believed to cause the RNA ends to more efficiently come together for the RNA ligase (e.g., RtcB). In other words, the ligation sequences are believed to help draw proper 5' and 3' ends of the RNA molecule closer to each other to assist in the circularization of the RNA molecule.

As used herein, the term "effector molecule" refers to one or more of the following: an RNA sequence that binds a protein; an RNA sequence that is complementary to a microRNA or siRNA; an RNA sequence that has partial complementarity to a microRNA or siRNA or piRNA; an RNA sequence that hybridizes completely or partially to a cellularly expressed microRNA, siRNA, piRNA, mRNA, lncRNA, ncRNA, or other cellular RNA; a hairpin structure that is a substrate for DICER or endogenous nucleases; a sequence that binds to viral proteins; an antisense RNA, an antagomir, a microRNA, an siRNA, an anti-miRNA, a ribozyme, a decoy oligonucleotide, an RNA activator, an immunostimulatory oligonucleotide, an aptamer, an RNA device; and an RNA molecule encoding a peptide sequence.

In some embodiments, a hairpin structure that serves as a substrate for an endogenous nuclease (e.g., DICER) is cleaved to produce an siRNA or microRNA.

MicroRNAs ("miRNAs" or "mirs") are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide RNA molecules that become incorporated into the RNA-induced silencing complex ("RISC") and have been identified as key regulators of development, cell proliferation, apoptosis, and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at the 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al., "Silencing of microRNAs In Vivo with 'Antagomirs'," Nature 438(7068):685-689 (2005), which is hereby incorporated by reference in its entirety).

Methods of producing a ribozyme targeted to a target sequence are known in the art. Ribozymes may be designed as described in PCT Publication No. WO 93/23569 and PCT Publication No. WO 94/02595, each of which is hereby incorporated by reference in its entirety, and synthesized to be tested in vitro and in vivo, as described therein.

As used herein, an "effector" molecule is an RNA sequence that has been selected based on a desired function.

In one embodiment, the effector molecule is an RNA aptamer. As used herein, the term "aptamer" refers to a nucleic acid molecule that binds with high affinity and specificity to a target. Nucleic acid aptamers may be single-stranded, partially single-stranded, partially double-stranded, or double-stranded nucleotide sequences. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

The RNA aptamer may comprise a fluorogenic aptamer. Fluorogenic aptamers are well known in the art and include, without limitation, Spinach, Spinach 2, Broccoli, Red-Broccoli, Orange Broccoli, Corn, Mango, Malachite Green, cobalamine-binding aptamer, and derivatives thereof. See, e.g., Autour et al., "Fluorogenic RNA Mango Aptamers for Imaging Small Non-Coding RNAs in Mammalian Cells," Nature Comm. 9: Article 656 (2018); Jaffrey, S., "RNA-Based Fluorescent Biosensors for Detecting Metabolites In Vitro and in Living Cells," Adv Pharmacol. 82:187-203 (2018); and Litke et al., "Developing Fluorogenic Riboswitches for Imaging Metabolite Concentration Dynamics in Bacterial Cells," Methods Enzymol. 572:315-33 (2016), each of which are hereby incorporated by reference in their entirety). In accordance with this embodiment, the fluorogenic aptamer binds to a fluorophore whose fluorescence, absorbance, spectral properties, or quenching properties are increased, decreased, or altered by interaction with the fluorogenic aptamer. Any aptamer-dye complex, some of which are fluorogenic aptamers, may be used. In addition, some aptamers can bind quenchers and some do other things to change the photophysical properties of dyes.

In another embodiment, the aptamer binds a target molecule of interest. The target molecule of interest may be any biomaterial or small molecule including, without limitation, proteins, nucleic acids (RNA or DNA), lipids, oligosaccharides, carbohydrates, small molecules, hormones, cytokines, chemokines, cell signaling molecules, metabolites, organic molecules, and metal ions. The target molecule of interest may be one that is associated with a disease state or pathogen infection. As demonstrated in the accompanying Examples, circular aptamers directed against a target molecule of interest can be developed to inhibit a cellular signaling pathway, e.g., the NF-κB signaling.

In some embodiments, the effector molecule comprises a fluorogenic aptamer coupled to an aptamer that binds a target molecule of interest. In accordance with this embodiment, the effector molecule may be a sensor. In accordance with this embodiment of the invention, the fluorogenic aptamer is coupled to an aptamer that binds a target molecule using a transducer stem. Suitable target molecules of interest include, but are not limited to, ADP, adenosine, guanine, GTP, SAM, and streptavidin. As demonstrated in the accompanying Examples, circular aptamer "sensors" can be developed, e.g., against SAM.

The RNA molecules of the present invention may be processed to comprise a 5'-OH end, a 2',3'-cyclic phosphate end, or a combination thereof. Such processing may be carried out by the RNA molecule itself, e.g., via the ribozymes. In accordance with these embodiments, the RNA molecules of the present invention are linear (i.e., have a 5' end and a 3' end). In another embodiment, the RNA molecules of the present invention are further processed to form circular RNA (i.e., RNA having no 5' end or 3' end), as described in more detail infra.

In another embodiment, the RNA molecules of the present invention are substrates for an RNA ligase. In one embodiment, the RNA molecule has the ability to auto-process to be a substrate for an RNA ligase, particularly the RNA ligase RtcB. Thus, in one embodiment, the RNA ligase is RtcB. In accordance with this embodiment, a linear RNA molecule having a 5'-OH end and a 2',3'-cyclic phosphate end can be processed to form a circular RNA molecule. In one embodiment, processing the RNA molecule to form a circular RNA molecule is an auto-process by the RNA molecule itself.

The RNA molecule of the present invention may circularize. For example, after it is acted upon by the RNA ligase, there are no termini, because all nucleotides are contiguously connected by covalent bonds. In one embodiment, 5' and 3' ends are no longer present due to the activity of the RNA ligase. In another embodiment, circular RNA means that the RNA has no observable end. Some RNA circles have unusual 5' to 2' linkages and not 5' to 3' linkages.

In other embodiments, a first linear RNA molecule having a 5'-OH end and a 2',3'-cyclic phosphate end is joined to a second linear RNA molecule having a 5'-OH end and a 2',3'-cyclic phosphate end.

As used herein, an "internal ribosome entry site" or "IRES" refers to an internal site of an mRNA sequence which recruits the ribosome or other translation initiation machinery to enable translation initiation. Various viral IRES elements are known in the art and include, for example, Picornavirus IRES, Aphthovirus IRES, Hepatitis A IRES, Hepatitis C IRES, and Pestivirus IRES. Exemplary IRES elements present in eukaryotic mRNA include, but are not limited to, fibroblast growth factor (FGF-1 IRES and FGF-2 IRES), platelet-derived growth factor B (PDGF/c-sis IRES), vascular endothelial growth factor (VEGF IRES), insulin-like growth factor 2 (IGF-II IRES), c-myc (c-myc IRES), L-myc (L-myc IRES), immunoglobulin heavy chain binding protein (BiP IRES), and heat shock protein 70 (HSP70 IRES). Modified nucleotides have been shown to be capable of recruiting ribosomes, most notably N6-methyladenosine (Meyer et al., "5' UTR m$^6$A Promotes Cap-Independent Translation," Cell 963:999-1010 (2015), which is hereby incorporated by reference in its entirety), and m$^6$A itself can also be considered an IRES-like molecule and is therefore included here under the term IRES as another mechanism to promote translation. m$^6$A has been shown to promote translation in naturally occurring circular RNAs.

When the effector molecule is an RNA molecule encoding a peptide sequence, the RNA molecule may further comprise an internal ribosomal entry site (IRES). In accordance with this embodiment, the IRES is operatively coupled to the RNA molecule encoding the peptide sequence.

Another aspect of the present invention relates to a vector comprising an RNA molecule according to the present application.

As used herein, the term "vector" refers to any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The vector contains the necessary elements for the transcription and/or translation of the nucleic acid sequence encoding the effector molecule(s) of the present invention.

In one embodiment, the vector is a plasmid. Numerous vectors suitable for use in the compositions of the present invention are known to those of skill in the art, and many are commercially available. The following vectors are provided by way of example; for eukaryotic cells: pXT1, pSG5 (Stratagene), pSVK3, pBPV, pMSG, and pSVLSV40 (Pharmacia). However, any other vector may be used so long as it is compatible with the cell.

In another embodiment, the vector is a viral vector. Suitable viral expression vectors include, but are not limited to, viral vectors based on vaccinia virus; poliovirus; adenovirus (see, e.g., PCT Publication Nos. WO 94/12649 to Gregory et al., WO 93/03769 to Crystal et al., WO 93/19191 to Haddada et al., WO 94/28938 to Wilson et al., WO 95/11984 to Gregory, and WO 95/00655 to Graham, which are hereby incorporated by reference in their entirety); adeno-associated virus (see, e.g., Ali et al., *Hum. Gene Ther.* 9:8186 (1998), Flannery et al., *PNAS* 94:6916-6921 (1997); Bennett et al., *Invest. Opthalmol. Vis. Sci.* 38:2857-2863 (1997); Jomary et al., *Gene Ther.* 4:683-690 (1997), Rolling et al., *Hum. Gene Ther.* 10:641-648 (1999); Ali et al., *Hum. Mol. Genet.* 5:591-594 (1996); Samulski et al., *J. Vir.* 63:3822-3828 (1989); Mendelson et al., *Virol.* 166:154-165 (1988); and Flotte et al., *PNAS* 90:10613-10617 (1993), which are hereby incorporated by reference in their entirety); SV40; herpes simplex virus; human immunodeficiency virus (see, e.g., Miyoshi et al., *PNAS* 94:10319-23 (1997); Takahashi et al., *J. Virol.* 73:781-7816 (1999), which are hereby incorporated by reference in their entirety); a retroviral vector, e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus and the like.

In one embodiment, the vector is a plasmid that expresses the Broccoli aptamer (pAV-U6+27-Tornado-Broccoli) and comprises the following sequence (SEQ ID NO:1):

GCCGGATCCA AGGTCGGGCA GGAAGAGGGC CTATTTCCCA

TGATTCCTTC ATATTTGCAT ATACGATACA

AGGCTGTTAG AGAGATAATT AGAATTAATT TGACTGTAAA

CACAAAGATA TTAGTACAAA ATACGTGACG

TAGAAAGTAA TAATTTCTTG GGTAGTTTGC AGTTTTAAAA

TTATGTTTTA AAATGGACTA TCATATGCTT

ACCGTAACTT GAAAGTATTT CGATTTCTTG GCTTTATATA

TCTTGTGGAA AGGACGAAAC ACCGTGCTCG

CTTCGGCAGC ACATATACTA GTCGACgGCC ATCAGTCGCC

GGTCCCAAGC CCGGATAAAA TGGGAGGGGG

CGGGAAACCG CCTaaccatG CCGACTGATG GCAGgagacg gtcgggtcca gatattcgta tctgtcgagt agagtgtggg ctcCTGCCAT CAGTCGGCGT GGACTGTAGA

ACACTGCCAA TGCCGGTCCC AAGCCCGGAT

AAAAGTGGAG GGTACAGTCC ACGCTCTAGA GCGGACTTCG

GTCCGCTTTT TACTAGGACC TGCAGGCATG

CAAGCTTGAC GTCGGTTACC GATATCCATA TGGCGGCCGC

ATCGATCTCG AGCCGCGGAC TAGTAACTTG

TTTATTGCAG CTTATAATGG TTACAAATAA AGCAATAGCA

TCACAAATTT CACAAATAAA GCATTTTTT

CACTGCATTC TAGTTGTGGT TTGTCCAAAC TCATCAATGT

ATCTTATCAT GTCTTACGTA GATAAGTAGC

ATGGCGGGTT AATCATTAAC TACAAGGAAC CCCTAGTGAT

GGAGTTGGCC ACTCCCTCTC TGCGCGCTCG

CTCGCTCACT GAGGCCGGGC GACCAAAGGT CGCCCGACGC

CCGGGCTTTG CCCGGGCGGC CTCAGTGAGC

GAGCGAGCGC GCAGAGAGGG AGTGGCCAAA GATCTCTGGC

GTAATAGCGA AGAGGCCCGC ACCGATCGCC

CTTCCCAACA GTTGCGCAGC CTGAATGGCT AATGGGAAAT

TGTAAACGTT AATATTTTGT TAATATTTTG

TTAAAATTCG CGTTAAATTT TTGTTAAATC AGCTCATTTT

TTAACCAATA GGCCGAAATC GGCAAAATCC

CTTATAAATC AAAAGAATAG ACCGAGATAG GGTTGAGTGT

TGTTCCAGTT TGGAACAAGA GTCCACTATT

AAAGAACGTG GACTCCAACG TCAAGGGCG AAAAACCGTC

TATCAGGGCG ATGGCCCACT ACGTGAACCA

TCACCCTAAT CAAGTTTTTT GGGGTCGAGG TGCCGTAAAG

CACTAAATCG GAACCCTAAA GGGATGCCCC

-continued

GATTTAGAGC TTGACGGGGA AAGCCGGCGA ACGTGGCGAG

AAAGGAAGGG AAGAAAGCGA AAGGAGCGGG

CGCTAGGGCG CTGGCAAGTG TAGCGGTCAC GCTGCGCGTA

ACCACCACAC CCGCCGCGCT TAATGCGCCG

CTACAGGGCG CGTCAGGTGG CACTTTTCGG GGAAATGTGC

GCGGAACCCC TATTTGTTTA TTTTTCTAAA

TACATTCAAA TATGTATCCG CTCATGAGAC AATAACCCTG

ATAAATGCTT CAATAATATT GAAAAAGGAA

GAGTATGAGT ATTCAACATT TCCGTGTCGC CCTTATTCCC

TTTTTTGCGG CATTTTGCCT TCCTGTTTTT

GCTCACCCAG AAACGCTGGT GAAAGTAAAA GATGCTGAAG

ATCAGTTGGG TGCACGAGTG GGTTACATCG

AACTGGATCT CAACAGCGGT AAGATCCTTG AGAGTTTTCG

CCCCGAAGAA CGTTTTCCAA TGATGAGCAC

TTTTAAAGTT CTGCTATGTG GCGCGGTATT ATCCCGTATT

GACGCCGGGC AAGAGCAACT CGGTCGCCGC

ATACACTATT CTCAGAATGA CTTGGTTGAG TACTCACCAG

TCACAGAAAA GCATCTTACG GATGGCATGA

CAGTAAGAGA ATTATGCAGT GCTGCCATAA CCATGAGTGA

TAACACTGCG GCCAACTTAC TTCTGACAAC

GATCGGAGGA CCGAAGGAGC TAACCGCTTT TTTGCACAAC

ATGGGGGATC ATGTAACTCG CCTTGATCGT

TGGGAACCGG AGCTGAATGA AGCCATACCA AACGACGAGC

GTGACACCAC GATGCCTGTA GCAATGGCAA

CAACGTTGCG CAAACTATTA ACTGGCGAAC TACTTACTCT

AGCTTCCCGG CAACAATTAA TAGACTGGAT

GGAGGCGGAT AAAGTTGCAG GACCACTTCT GCGCTCGGCC

CTTCCGGCTG CTGGTTTAT TGCTGATAAA

TCTGGAGCCG GTGAGCGTGG GTCTCGCGGT ATCATTGCAG

CACTGGGGCC AGATGGTAAG CCCTCCCGTA

TCGTAGTTAT CTACACGACG GGGAGTCAGG CAACTATGGA

TGAACGAAAT AGACAGATCG CTGAGATAGG

TGCCTCACTG ATTAAGCATT GGTAACTGTC AGACCAAGTT

TACTCATATA TACTTTAGAT TGATTTAAAA

CTTCATTTTT AATTTAAAAG GATCTAGGTG AAGATCCTTT

TTGATAATCT CATGACCAAA ATCCCTTAAC

GTGAGTTTTC GTTCCACTGA GCGTCAGACC CCGTAGAAAA

GATCAAAGGA TCTTCTTGAG ATCCTTTTTT

TCTGCGCGTA ATCTGCTGCT TGCAAACAAA AAAACCACCG

CTACCAGCGG TGGTTTGTTT GCCGGATCAA

GAGCTACCAA CTCTTTTTCC GAAGGTAACT GGCTTCAGCA

-continued

```
GAGCGCAGAT ACCAAATACT GTCCTTCTAG

TGTAGCCGTA GTTAGGCCAC CACTTCAAGA ACTCTGTAGC

ACCGCCTACA TACCTCGCTC TGCTAATCCT

GTTACCAGTG GCTGCTGCCA GTGGCGATAA GTCGTGTCTT

ACCGGGTTGG ACTCAAGACG ATAGTTACCG

GATAAGGCGC AGCGGTCGGG CTGAACGGGG GGTTCGTGCA

ACACAGCCAG CTTGGAGCGA ACGACCTACA

CCGAACTGAG ATACCTACAG CGTGAGCATT GAGAAAGCGC

CACGCTTCCC GAAGGGAGAA AGGCGGACAG

GTATCCGGTA AGCGGCAGGG TCGGAACAGG AGAGCGCACG

AGGGAGCTTC CAGGGGGAAA CGCCTGGTAT

CTTTATAGTC CTGTCGGGTT TCGCCACCTC TGACTTGAGC

GTCGATTTTT GTGATGCTCG TCAGGGGGC

GGAGCCTATG GAAAACGCC AGCAACGCGG CCTTTTTACG

GTTCCTGGCC TTTTGCTGGC CTTTTGCTCA

CATGTTCTTT CCTGCGTTAT CCCCTGATTC TGTGGATAAC

CGTATTACCG CCTTTGAGTG AGCTGATACC

GCTCGCCGCA GCCGAACGAC CGAGCGCAGC GAGTCAGTGA

GCGAGGAAGC GGAAGAGCGC CCAATACGCA

AACCGCCTCT CCCCGCGCGT TGGCCGATTC ATTAATGCAG

AGATCTTTGG CCACTCCCTC TCTGCGCGCT

CGCTCGCTCA CTGAGGCCGG GCGACCAAAG GTCGCCCGAC

GCCCGGGCTT TGCCCGGGCG GCCTCAGTGA

GCGAGCGAGC GCGCAGAGAG GGAGTGGCCA ACTCCATCAC

TAGGGGTTCC TGGAGGGGTG GAGTCGTGAC

GTGAATTACG TCATAGGGTT AGGGAGGTCC TGGATCGATC

CAGACATGAT AAGATACATT GATGAGTTTG

GACAAACCAC AACTAGAATG CAGTGAAAAA AATGCTTTAT

TTGTGAAATT TGTGATGCTA TTGCTTTATT

TGTAACCATT ATAAGCTGCA ATAAACAAGT TAACAACAAC

AATTGCATTC ATTTTATGTT TCAGGTTCAG

GGGGAGGTGT GGGAGGTTTT TTAAAGCAAG TAAAACCTCT

ACAAATGTGG TATGGCTGAT TATGATCTCT

AGTCAAGGCA CTATACATCA AATATTCCTT ATTAACCCCT

TTACAAATTA AAAAGCTAAA GGTACACAAT

TTTTGAGCAT AGTTATTAAT AGCAGACACT CTATGCCTGT

GTGGAGTAAG AAAAAACAGT ATGTTATGAT

TATAACTGTT ATGCCTACTT ATAAAGGTTA CAGAATATTT

TTCCATAATT TTCTTGTATA GCAGTGCAGC

TTTTTCCTTT GTGGTGTAAA TAGCAAAGCA AGCAAGAGTT
```

-continued

```
CTATTACTAA ACACAGCATG ACTCAAAAAA

CTTAGCAATT CTGAAGGAAA GTCCTTGGGG TCTTCTACCT

TTCTCTTCTT TTTTGGAGGA GTAGAATGTT

GAGAGTCAGC AGTAGCCTCA TCATCACTAG ATGGCATTTC

TTCTGAGCAA AACAGGTTTT CCTCATTAAA

GGCATTCCAC CACTGCTCCC ATTCATCAGT TCCATAGGTT

GGAATCTAAA ATACACAAAC AATTAGAATC

AGTAGTTTAA CACATTATAC ACTTAAAAAT TTTATATTTA

CCTTAGAGCT TTAAATCTCT GTAGGTAGTT

TGTCCAATTA TGTCACACCA CAGAAGTAAG GTTCCTTCAC

AAAGATCCGG GACCAAAGCG GCCATCGTGC

CTCCCCACTC CTGCAGTTCG GGGGCATGGA TGCGCGGATA

GCCGCTGCTG GTTTCCTGGA TGCCGACGGA

TTTGCACTGC CGGTAGAACT CCGCGAGGTC GTCCAGCCTC

AGGCAGCAGC TGAACCAACT CGCGAGGGGA

TCGAGCCCGG GGTGGGCGAA GAACTCCAGC ATGAGATCCC

CGCGCTGGAG GATCATCCAG CCGGCGTCCC

GGAAAACGAT TCCGAAGCCC AACCTTTCAT AGAAGGCGGC

GGTGGAATCG AAATCTCGTG ATGGCAGGTT

GGGCGTCGCT TGGTCGGTCA TTTCGAACCC CAGAGTCCCG

CTCAGAAGAA CTCGTCAAGA AGGCGATAGA

AGGCGATGCG CTGCGAATCG GGAGCGGCGA TACCGTAAAG

CACGAGGAAG CGGTCAGCCC ATTCGCCGCC

AAGCTCTTCA GCAATATCAC GGGTAGCCAA CGCTATGTCC

TGATAGCGGT CCGCCACACC CAGCCGGCCA

CAGTCGATGA ATCCAGAAAA GCGGCCATTT TCCACCATGA

TATTCGGCAA GCAGGCATCG CCATGGGTCA

CGACGAGATC CTCGCCGTCG GGCATGCGCG CCTTGAGCCT

GGCGAACAGT TCGGCTGGCG CGAGCCCCTG

ATGCTCTTGT CCAGATCATC CTGATCGACA AGACCGGCTT

CCATCCGAGT ACGTGCTCGC TCGATGCGAT

GTTCGCTTGG TGGTCGAATG GGCAGGTAGC CGGATCAAGC

GTATGCAGCC GCCGCATTGC ATCAGCCATG

ATGGATACTT TCTCGGCAGG AGCAAGGTGA GATGACAGGA

GATCCTGCCC CGGCACTTCG CCCAATAGCA

GCCAGTCCCT TCCCGCTTCA GTGACAACGT CGAGCACAGC

TGCGCAAGGA ACGCCCGTCG TGGCCAGCCA

CGATAGCCGC GCTGCCTCGT CCTGCAGTTC ATTCAGGGCA

CCGGACAGGT CGGTCTTGAC AAAAAGAACC

GGGCGCCCCT GCGCTGACAG CCGGAACACG GCGGCATCAG

AGCAGCCGAT TGTCTGTTGT GCCCAGTCAT
```

```
AGCCGAATAG CCTCTCCACC CAAGCGGCCG GAGAACCTGC

GTGCAATCCA TCTTGTTCAA TCATGCGAAA

CGATCCTCAT CCTGTCTCTT GATCAGATCT TGATCCCCTG

CGCCATCAGA TCCTTGGCGG CAAGAAAGCC

ATCCAGTTTA CTTTGCAGGG CTTCCCAACC TTACCAGAGG

GCGCCCCAGC TGGCAATTCC GGTTCGCTTG

CTGTCCATAA AACCGCCCAG TCTAGCTATC GGCATGTAAG

CCCACTGCAA GCTACCTGCT TTCTCTTTGC

GCTTGCGTTT TCCCTTGTCC AGATAGCCCA GTAGCTGACA

TTCATCCGGG GTCAGCACCG TTTCTGCGGA

CTGGCTTTCT ACGTGTTCCG CTTCCTTTAG CAGCCCTTGC

GCCCTGAGTG CTTGCGGCAG CGTGAAGCTT

TTTGCAAAAG CCTAGGCCTC CAAAAAGCC TCCTCACTAC

TTCTGGAATA GCTCAGAGGC CGAGGCGGCC

TCGGCCTCTG CATAAATAAA AAAAATTAGT CAGCCATGGG

GCGGAGAATG GGCGGAACTG GGCGGAGTTA

GGGGCGGGAT GGGCGGAGTT AGGGGCGGGA CTATGGTTGC

TGACTAATTG AGATGCATGC TTTGCATACT

TCTGCCTGCT GGGGAGCCTG GGGACTTTCC ACACCTGGTT

GCTGACTAAT TGAGATGCAT GCTTTGCATA

CTTCTGCCTG CTGGGGAGCCT GGGGACTTTC CACACCCTAA

CTGACACACAT TCCACA
```

As used herein, the term "promoter" refers to a DNA sequence which contains the binding site for RNA polymerase and initiates transcription of a downstream nucleic acid sequence. In one embodiment, the vector comprises a promoter.

The promoter of the present invention may be a constitutively active promoter (i.e., a promoter that is constitutively in an active or "on" state), an inducible promoter (i.e., a promoter whose state, active or inactive state, is controlled by an external stimulus, e.g., the presence of a particular temperature, compound, or protein), a spatially restricted promoter (i.e., transcriptional control element, enhancer, etc.) (e.g., tissue specific promoter, cell type specific promoter, etc.), or a temporally restricted promoter (i.e., the promoter is in the "on" state or "off" state during specific stages of a biological process).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., RNA Polymerase I, RNA Polymerase II, RNA Polymerase III). Exemplary promoters include, but are not limited to the SV40 early promoter, mouse mammary tumor virus long terminal repeat ("LTR") promoter; adenovirus major late promoter ("Ad MLP"); a herpes simplex virus ("HSV") promoter, a cytomegalovirus ("CMV") promoter such as the CMV immediate early promoter region ("CMVIE"), a rous sarcoma virus ("RSV") promoter, a human U6 small nuclear promoter ("U6") (Miyagishi et al., "U6 promoter-driven siRNAs with four uridine 3' overhangs efficiently suppress targeted gene expression in mammalian cells," *Nature Biotechnology* 20:497-500 (2002), which is hereby incorporated by reference in its entirety), an enhanced U6 promoter (e.g., Xia et al., "An enhanced U6 promoter for synthesis of short hairpin RNA," *Nucleic Acids Res.* 31(17):e100 (2003), which is hereby incorporated by reference in its entirety), a human H1 promoter ("H1"), and the like.

Examples of inducible promoters include, but are not limited to, T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter, steroid-regulated promoter, metal-regulated promoter, estrogen receptor-regulated promoter, etc. Inducible promoters can therefore be regulated by molecules including, but not limited to, doxycycline, RNA polymerase, e.g., T7 RNA polymerase, an estrogen receptor, an estrogen receptor fusion, etc.

In one embodiment, the promoter is a prokaryotic promoter selected from the group consisting of T7, T3, SP6 RNA polymerase, and derivatives thereof. Additional suitable prokaryotic promoters include, without limitation, T7lac, araBAD, trp, lac, Ptac, and pL promoters.

In another embodiment, the promoter is a eukaryotic RNA polymerase I promoter, RNA polymerase III promoter, or a derivative thereof. Exemplary RNA polymerase II promoters include, without limitation, cytomegalovirus ("CMV"), phosphoglycerate kinase-1 ("PGK-1"), and elongation factor 1α ("EF1α") promoters. In yet another embodiment, the promoter is a eukaryotic RNA polymerase III promoter selected from the group consisting of U6, H1, 56, 7SK, and derivatives thereof.

The RNA Polymerase promoter may be mammalian. Suitable mammalian promoters include, without limitation, human, murine, bovine, canine, feline, ovine, porcine, ursine, and simian promoters. In one embodiment, the RNA polymerase promoter sequence is a human promoter.

In another embodiment, one can simply engineer the genome to express the RNA molecule of the present invention without using a vector. According to this embodiment, a vector is not needed if the cell, animal, or tissue where expression of the RNA molecule is desired has its genome engineered to express the ribozyme—effector molecule—ribozyme sequence of the present invention.

A further aspect of the present invention is directed to a nucleic acid molecule that contains the RNA molecule of the present invention. In other words, the nucleic acid molecule does not have to be a vector. In one embodiment, the nucleic acid molecule is a piece of ss or dsDNA that contains the sequences of the RNA molecule of the present invention.

The present invention further relates to a cell comprising a vector or other nucleic acid molecule according to the present invention. In one embodiment, the cell comprises an endogenous RNA ligase. In one embodiment, the endogenous RNA ligase has the ability to catalyze the circularization of a ribonucleic acid molecule having a 5'-OH and a 2',3'-cyclic phosphate. In accordance with one embodiment, the endogenous RNA ligase is RtcB. It will be recognized that there are some enzymes that are related in function to RtcB, but not in sequence to RtcB. In one embodiment, the RNA ligase is any RNA ligase that detects 5'-OH and 2'-3'-cyclic phosphate ends.

Another aspect of the present invention relates to a method of producing an RNA molecule. This method involves providing one or more vectors comprising a nucleic acid sequence encoding a 5' polymerase promoter sequence, a nucleic acid sequence encoding a first ribozyme, a nucleic acid sequence encoding a first ligation sequence, a nucleic acid sequence encoding an effector sequence, a nucleic acid sequence encoding a second ligation sequence, a nucleic acid sequence encoding a second ribozyme, and a nucleic acid sequence encoding a 3' polymerase terminator sequence and transcribing the one or more vectors to produce one or more linear RNA molecules.

In this and other aspects of the present invention, the ligation sequences may or may not be present.

A further aspect of the present invention relates to a method of producing a circular RNA molecule. This method involves providing one or more vectors comprising a nucleic acid sequence encoding a 5' polymerase promoter sequence, a nucleic acid sequence encoding a first ribozyme, a nucleic acid sequence encoding a first ligation sequence, a nucleic acid sequence encoding an effector molecule, a nucleic acid sequence encoding a second ligation sequence, a nucleic acid sequence encoding a second ribozyme, and a nucleic acid sequence encoding a 3' polymerase terminator sequence. The method further involves transcribing the one or more vectors to produce one or more linear RNA molecules and contacting the one or more linear RNA molecules with an RNA ligase to form a circular RNA molecule.

Suitable promoter sequences, ligations sequences, and ribozymes are described in detail above.

As used herein, the term "terminator" refers to a DNA sequence that is involved in the termination of transcription.

In one embodiment, said transcribing the one or more vectors is carried out by introducing the vector into a cell. A vector according to the present invention may be introduced into the cell by transformation or transfection. Methods for transforming and/or transfecting cells with vectors are well-known in the art and depend on the selected cell, as described in SAMBROOK & RUSSELL, MOLECULAR CLONING: A LABORATORY MANUAL (Cold Springs Laboratory Press, 2001), which is hereby incorporated by reference in its entirety. For bacterial cells, suitable techniques include calcium chloride transformation, electroporation, and transfection using bacteriophage. For eukaryotic cells, suitable techniques include calcium phosphate transfection, DEAE-Dextran, electroporation, liposome-mediated transfection, and transduction using retrovirus or any other viral vector.

Suitable mammalian cells and bacterial cells for use in the present invention are well known in the art.

In one embodiment, the RNA ligase is contained in the cell. In one embodiment, the cell is engineered to express (or overexpress) RNA ligase.

In another embodiment, the one or more linear RNA molecules comprise a 5'-OH end, a 2',3'-cyclic phosphate end, and a combination thereof.

The RNA ligase may have the ability to catalyze the circularization of a ribonucleic acid molecule having a 5'-OH and a 2',3'-cyclic phosphate. In accordance with this embodiment, the RNA ligase is RtcB or any other RNA ligase capable of ligating an RNA having a 5'-OH and a 2',3'-cyclic phosphate.

In one embodiment, the one or more vectors further comprise a nucleic acid sequence encoding an effector molecule. The nucleic acid sequence encoding the effector molecule may be positioned downstream of the nucleic acid sequence encoding the first ligation sequence and upstream of the nucleic acid sequence encoding the second ligation sequence to produce a vector encoding the effector molecule.

Suitable effector molecules are described supra.

In one embodiment of the methods of making an RNA molecule of the present invention, the RNA is synthesized (e.g., by chemical synthesis) or in vitro transcribing the RNA, allowed to self-process via the ribozymes, and then incubated with purified RtcB. Circular RNA is then purified by standard methods. As discussed in more detail infra, the purified circular RNA may then be administered to a person or cell, e.g., for treatment purposes.

According to another embodiment of the methods of making an RNA molecule of the present invention, RNA is expressed from a genome or from a plasmid or a phage as described herein. In one embodiment, RtcB such RNA expression is accompanied by overexpression of RtcB (or another suitable RNA ligase). According to this embodiment, it would be possible to manufacture large quantities of circular RNA (e.g., in E. coli) for subsequent purification.

In carrying out these methods of the present invention, it may be desirable to sequence the RNA transcripts or RNA transcript fragments. In one embodiment, sequencing of RNA transcripts is carried out by next-generation sequencing.

In addition, conventional nucleic acid analysis techniques may be applied to the RNA transcripts to perform additional analyses. For example, the presence of sequences of interest in the RNA transcripts may be determined using techniques such as PCR, slot blots, microarrays, etc., all of which are well known to those of ordinary skill in the art. According to one embodiment, a microchip system comprising a microarray of oligonucleotide or longer nucleotide sequences on a glass support is employed. Sample nucleic acid (e.g., fluorescently labelled) may be hybridized to the oligonucleotide array and sequence specific hybridization may be detected by scanning confocal microscopy and analyzed automatically (see Marshall & Hodgson, "DNA Chips: An Array of Possibilities," *Nature Biotechnology* 16:27-31 (1998); see also Schulze et al., "Navigating Gene Expression Using Microarrays—A Technology Review," *Nature Cell Biology* 3:E190-E195 (2001), each of which is hereby incorporated by reference in its entirety). A list of currently used techniques in microarray assembly and DNA detection can be found in the book *DNA Microarrays: A Molecular Cloning Manual*, eds. Bowtell and Sambrook, CSHL 2002, which is hereby incorporated by reference in its entirety.

A further aspect of the present invention relates to a treatment method. This treatment method involves contacting a cell with an RNA molecule of the present invention under conditions effective to express the effector molecule to treat the cell.

According to one embodiment, this and other treatment methods described herein are effective to treat a cell, e.g., a cell under a stress or disease condition. Exemplary cell stress conditions may include, without limitation, exposure to a toxin; exposure to chemotherapeutic agents, irradiation, or environmental genotoxic agents such as polycyclic hydrocarbons or ultraviolet (UV) light; exposure of cells to conditions such as glucose starvation, inhibition of protein glycosylation, disturbance of $Ca^{2+}$ homeostasis and oxygen; exposure to elevated temperatures, oxidative stress, or heavy metals; and exposures to a pathological disease state (e.g., diabetes, Parkinson's disease, cardiovascular disease (e.g., myocardial infarction, end-stage heart failure, arrhythmogenic right ventricular dysplasia, and Adriamycin-induced cardiomyopathy), and various cancers (Fulda et al., "Cellular Stress Responses: Cell Survival and Cell Death," *Int. J. Cell Biol.* (2010), which is hereby incorporated by reference in its entirety).

Various embodiments of the RNA molecules of the present invention are described above and apply in carrying out this and other treatment methods described herein. For example, in one embodiment the RNA molecule comprises a first ribozyme, an effector molecule, and a second ribozyme. In another embodiment, the RNA molecule may further comprise a first ligation sequence and a second ligation sequence. For example, the first ligation sequence may be positioned upstream of the effector molecule and the second ligation sequence may be positioned downstream of the effector molecule.

In some embodiments, contacting a cell with an RNA molecule of the present invention involves introducing an RNA molecule into a cell. Suitable methods of introducing RNA molecules into cells are well known in the art and include, but are not limited to, the use of transfection reagents, electroporation, microinjection, or via viruses.

The cell may be a eukaryotic cell. Exemplary eukaryotic cells include a yeast cell, an insect cell, a fungal cell, a plant cell, and an animal cell (e.g., a mammalian cell). Suitable mammalian cells include, for example without limitation, human, non-human primate, cat, dog, sheep, goat, cow, horse, pig, rabbit, and rodent cells.

In certain embodiments of the treatment methods of the present invention, the RNA molecule encodes an effector molecule as described herein.

In other embodiments of the treatment methods of the present invention, the RNA molecule encodes a therapeutic protein or peptide sequence. The therapeutic protein or peptide sequence may be endogenous or heterologous to the cell. The therapeutic protein or peptide sequence may be down-regulated in a disease state, a stress state, or during a pathogen infection of a cell.

In another embodiment, the RNA molecule of the present invention may be isolated or present in in vitro conditions for extracellular expression and/or processing. According to this embodiment, the RNA molecule is contacted by an RNA ligase (e.g., RtcB) in vitro, purified, circularized, and then the circularized RNA molecule is administered to a cell or subject for treatment.

Treating cells also includes treating the organism in which the cells reside. Thus, by this and the other treatment methods of the present invention, it is contemplated that treatment of a cell includes treatment of a subject in which the cell resides.

Another aspect of the present invention relates to a treatment method. This method involves contacting a cell with a vector according to the present application under conditions effective to express of the effector molecule to treat the cell.

In one embodiment of carrying out this method of the present invention, the vector encodes an RNA molecule which encodes a therapeutic effector molecule. The therapeutic effector molecule may be endogenous or heterologous to the cell. The therapeutic effector molecule may serve to up-regulate or down-regulated expression of a protein in a disease state, a stress state, or during a pathogen infection in a cell. The therapeutic effector molecule may be a synthetic effector molecule or a naturally-occurring effector molecule.

In a further aspect, the present invention relates to an RNA molecule comprising a 5'-OH end and a 2',3'-cyclic phosphate end, where the RNA molecule further comprises an effector molecule between the 5'-OH and the 2',3'-cyclic phosphate ends.

EXAMPLES

The examples below are intended to exemplify the practice of embodiments of the disclosure but are by no means intended to limit the scope thereof.

Materials and Methods

Preparation of RNA and Observation of Ribozyme Cleavage: Double-stranded DNA for in vitro transcription were prepared from single stranded DNA templates (Integrated DNA Technologies) and designed to contain a 5' T7 promoter. Templates were amplified by PCR using Taq DNA polymerase (NEB M02373) or Phusion® High-Fidelity DNA Polymerase (NEB M0530) and checked for quality using 0.8% agarose gel electrophoresis. Impure reaction products were isolated by gel excision and purified with the Qiaquick Gel Extraction kit (Qiagen 28704). Pure PCR reactions were purified with the Qiaquick PCR purification kit (Qiagen 28104).

In vitro transcription reactions used the AmpliScribe™ T7-Flash™ transcription kit (Lucigen ASF3507) carried out at 37° C. For observing ribozyme cleavage, transcription reactions were quenched by adding PAGE sample buffer containing urea (ThermoFisher LC6876). Samples were separated using a precast 6% TBE-Urea Gel (Life Technologies EC68655), and ran at 270 V in TBE buffer until completion. After staining with SYBR Gold (ThermoFisher S11494) diluted in TBE buffer, RNA bands were imaged using a ChemiDoc MP (Bio-Rad) with a preset channel (302 nm excitation and 590/110 nm emission).

All other transcription reactions for preparing RNA were incubated overnight. Reactions were treated with RNase-Free DNase I at 37° C. for at least 30 minutes to remove DNA templates and then 13.3 mM EDTA free of RNases (Sigma 03690) and incubated at 75° C. for 10 minutes. RNA was then purified from reactions using the RNA Clean & Concentrator kit (Zymo R1015).

Excision and Purification of RNA: After staining of PAGE gels, individual RNA bands were isolated from the gel. Bands were excised from gels and crushed by spinning through Gel Breaker Tubes (IST Engineering, Inc 3388-100). Samples were incubated in an extraction buffer (10 mM Tris HCl pH 6.8, 300 mM NaCl, 1 mM EDTA) for 1 hour at 25 or 37° C., and after placing samples on dry ice for 5 minutes, they were incubated for an additional hour. Remaining gel pieces were removed through Costar SpinX columns (Corning, 8161), which was followed by ethanol precipitation.

Reactions of RNA Templates with T4 PNK and RtcB: After gel purification of autocatalytically cleaved RNA, 300 pmol were treated with T4 polynucleotide kinase (New England Biolabs M0201) according to the manufacturer's protocol at 37° C. for 30 minutes and inactivated for 20 minutes at 65° C. The products were cleaned by phenol chloroform extraction using heavy phase-lock tubes (Quantabio 2302830). 10 pmol of this purified T4-PNK-treated RNA or of the gel purified RNA was ligated using RtcB Ligase (New England Biolabs M0458) for 1 hour at 37° C.

Cloning of Autocatalytic circRNA Constructs: DNA templates containing Broccoli and each of the ribozyme combinations were prepared as described above with flanking SalI and XbaI restriction sites. These constructs were cloned downstream of a U6+27 promoter and upstream of the U6 terminator in a pAV vector that contains the SV40 origin (Paul et al., "Effective Expression of Small Interfering RNA in Human Cells," Nat. Biotechnol. 20:505-508 (2002), which is hereby incorporated by reference in its entirety). This U6 promoter includes the first 27 nucleotides of U6 RNA.

Subsequent plasmids were made for cloning one or two aptamers directly into the Tornado expression cassette. These constructs were generated in the same way and used NotI and SacII, RsrII, or KflI restriction enzyme sites for inserting RNA aptamer sequence. They used the same pAV backbone or a version containing a gene for mCherry fluorescent protein expression.

Cell Culture and Transfection. HEK293T/17 (ATCC CRL-11268), COS-7 (ATCC CRL-1651), Hep G2 (ATCC HB-8065), and HeLa (ATCC CCL-2) cells were maintained in 1×DMEM (11995-065, Life Technologies) with 10% FBS, 100 U ml$^{-1}$ penicillin and 100 µg ml$^{-1}$ of streptomycin under standard tissue culture conditions. NF-κB reporter (luciferase) HEK293 (BPS Biosciences 60650) cells were maintained in these conditions with 50 µg/mL hygromycin B (Life Technologies 10687010). All cells were split using TrypLE Express (Life Technologies) according to manufacturer's instructions. Cell lines were plated for transfection using FuGENE HD (Promega 2311) according to the manufacturer's instructions using OptiMEM™ I Reduced Serum Media (Thermo Fisher 31985). For experiments testing the stability of circRNAs, 5 pg/mL Actinomycin D (Sigma, A9415) was added to cells for 6 hours prior to extraction of RNA.

RNA Extraction: RNA was harvested from cultured cells by removing media and detaching enzymatically or directly lifting cells with 1× Phosphate Buffered Saline ("PBS") (ThermoFisher 10010031). Cell suspensions were mixed with TRIzol™ LS Reagent (Invitrogen 10296010), then frozen and store at −20° C. or purified immediately according to the manufacturer's instructions. Total RNA concentrations were normalized using a NanoDrop 2000 (Thermo Scientific).

In-Gel Broccoli Imaging: Typically 1.0-2.5 µg of total RNA were separated using precast 6% or 10% TBE-Urea Gels (Life Technologies EC68655), and ran at 270 V in TBE buffer until completion. Gels were washed and probed for Broccoli as previously described (Filonov et al., "RNA Imaging with Dimeric Broccoli in Live Bacterial and Mammalian Cells," Curr. Protoc. Chem. Biol. 8:1-28 (2016), which is hereby incorporated by reference in its entirety), using minimal volumes (15 mL) of wash and stain to reduce escape of RNA from the gel. Gels were washed 3×5 minutes with water and then stained for 30 min in 10 µM DFHBI in buffer containing 40 mM HEPES pH 7.4, 125 mM KCl, 5 mM MgCl$_2$, Broccoli bands were then imaged using a ChemiDoc MP (Bio-Rad) with 470/30 nm excitation and 532/28 nm emission. Gels were washed additionally with water and stained with SYBR Gold (ThermoFisher S11494) diluted in TBE buffer. RNA bands were imaged using a ChemiDoc MP (Bio-Rad) with a preset channel (302 nm excitation and 590/110 nm emission). Gel band intensities were quantified in Image Lab 5.0 software (Bio-Rad).

Reactions of circRNA with Exoribonuclease: RNA was treated with T4 PNK or RtcB as described above. Products were purified using phenol chloroform extraction as described above. Purified reactions were treated with Rnase R (Lucigen, RNR07250) as recommended by the manufacturer.

Site-Specific circRNA Cleavage: A construct using Tornado that would express a 275-nt circRNA containing a series of scrambled RNA sequences as well as Broccoli was designed. This plasmid was transfected into HEK293T cells. Next, the RNA was extracted and the band where in-gel Broccoli fluorescence was observed was purified, as described above. A sample of linear RNA with the same sequence was prepared by in vitro transcription followed by column purification as described above. A 15-nt anti-sense DNA primer (Integrated DNA Technologies) with reverse complementarity for a region of the scrambled RNA sequence was also designed. Site-specific cleavage was performed in reactions containing 100 ng of the target RNA, 10 pmol of the antisense primer, Rnasin® Ribonuclease Inhibitor (Promega, N211A), and 0.5 µL Hybridase™ Thermostable RNase H (Lucigen, H39500) in a total volume of 10 µL. Reaction buffer contained 100 mM NaCl, 40 mM Tris-HCl pH 7.7, 4 mM MgCl$_2$, 1 mM DTT, and 0.03% BSA. Reactions were incubated at 50° C. for 10 minutes prior to adding the enzyme, after which they proceeded for 2 hours at 42° C.

Comparison of Tornado with other Circular RNA Expression Methods: Plasmids encoding Broccoli in other circular RNA generating expression system were derived from a number of sources. The permuted-intron-exon system based on group I intron splicing was derived from the td T4 bacteriophage gene as previously described (Ares, M., "Synthesis of Circular RNA in Bacteria and Yeast Using RNA," 91:3117-3121 (1994) and Umekage et al., "In Vitro and In Vivo Production and Purification of Circular RNA Aptamer," J. Biotechnol. 139:265-272 (2009), which are hereby incorporated by reference in their entirety) by cloning into the same pAV vector used above. Plasmids generating spliced sno-lncRNA containing Broccoli (Yin et al., "Long Noncoding RNAs with snoRNA Ends," Mol. Cell 48:219-230 (2012), which is hereby incorporated by reference in its entirety) and tRNA intron circular RNA containing Broccoli (Lu et al., "Metazoan tRNA Introns Generate Stable Circular RNAs In Vivo," RNA 21(9):1554-65 (2015), which is hereby incorporated by reference in its entirety) were prepared as described previously.

Microscopy and Image Processing: Pre-coated 3.5 cm glass-bottom dishes (MatTek Corporation P35GC-1.5-14-C) or glass-bottom 24-well plates 1.5 (MatTek Corporation P24G-1.5-13-F) that were coated with poly-D-lysine (Cultrex, 3429-100-01) for at least 3 hours and rinsed twice in 1×PBS were used for imaging cells. For imaging cells longer than a few hours, these plates and dishes were additionally coated with Cultrex Mouse Laminin I (ThermoFisher, 50948048) for at least 1 hour and rinsed twice in 1×PBS. Cells were subcultured onto glass bottom vessels one or two days after transfection, depending on the experiment. 30 minutes before the imaging, the media was changed into FluoroBrite media (Thermo Fisher, A1896701) containing 40 µM DFHBI-1T or DFHO (synthesized (Song et al., "Imaging RNA Polymerase III Transcription Using a Photostable RNA-Fluorophore Complex," Nat. Chem. Biol. 13:1187-1194 (2017), which is hereby incorporated by reference in its entirety) or Lucerna, 500-1 mg) and 0.1 µg/mL of Hoechst 33342 (ThermoFisher, H3570). Live-cell fluorescence images were taken with a CoolSnap HQ2 CCD camera through a 20× or 40× air objective mounted on a Nikon Eclipse TE2000-E microscope and analyzed with the NIS-Elements software. Conditions were maintained at 37° C. and 5% CO$_2$. The filter set used for Broccoli detection was a filter cube with excitation filter 470±20 nm, dichroic mirror 495 nm (long pass), and emission filter 525±25 nm. mCherry was detected using 560±20 nm excitation filter, 585 nm (long pass) dichroic mirror, and 630±37.5 nm emission filter. Corn detection used a filter cube with excitation filter 500±12 nm, dichroic mirror 520 nm (long pass), and emission filter 542±13.5 nm. Hoechst-stained nuclei were imaged with 350±25 nm excitation filter, 400 nm (long pass) dichroic mirror, and 460±25 nm emission filter (all filters are from Chroma Technology). Exposure times: 200-500 msec for Broccoli, 200 msec for mCherry and Hoechst. Total cell fluorescence was computed using ImageJ by measuring the total signal in a cell's area and subtracting background based on average signal of an untransfected cell.

Quantification of intracellular RNA concentrations: Two days after transfecting HepG2, HeLa, and HEK293T cells with a mammalian plasmid encoding Tornado expression of Broccoli from a U6 promoter, pAV-U6+27-Tornado, and a pSuperior encoding mCherry in a 1:1 ratio, cells were lifted using TrypLE. Each cell suspension was plated for imaging so that transfection efficiency could subsequently be quantified by microscopy the next day. With the remaining cell suspension, the number of cells in each cell line was quantified, and then total RNA was extracted from each using TRIzol LS as described above. The gross intracellular volume of each sample was calculated given the quantification of cell number and previous reports of cell volume to 2 pL (might be as much lower as $^1/_{10}$th when measuring spherical trypsinized cells volume by diameter*, repeat). Then, 1 μg of each cell line's total RNA was separated by denaturing PAGE using 10% Urea and imaged the Broccoli fluorescence in the gel using DFHBI-1T as described above. The amounts of circular Broccoli detected in the fraction of the sample loaded on the gel was quantified according to 100 ng through 0.01 ng standards of the same RNA loaded in adjacent lanes. Then, the gross amounts of circular Broccoli for each sample was calculated and then the intracellular concentration was calculated by converting to gross molar amounts dividing by gross intracellular volume. Lastly, concentration values were corrected for transfection efficiency observations made in each cell line.

Stimulation and detection of NF-κB Signaling: HEK293 recombinant cells containing a NF-κB-promoter-driven luciferase reporter (BPS Sciences, 60650) were used to detect activation of the NF-κB pathway. Two days after plasmid transfection cells were subcultured in triplicate into 96-well plates for luminescence detection. The next day, cells were stimulated and their activation was detected. Cells with chemically inhibited conditions were incubated with 50 μM of BAY 11-7082 (Santa Cruz Biotechnology, sc-200615) for 30 minutes. Cells were stimulated with 50 ng/mL Recombinant Human IL-1β (Peprotech, 200-01b) for 2.5 hours. Luminescence was generated with the One-Glo™ Luciferase Assay System (Promega, E6110) as recommended by the manufacturer and detected at 570 (Molecular Devices, SpectraMax® L Microplate Reader).

Flow Cytometry of Mammalian Cells: HEK293 recombinant cells containing a NF-κB-promoter-driven luciferase reporter (BPS Sciences, 60650) were transfected with plasmids encoding bifunctional circular RNA aptamers. 48 hours after transfection, cells were resuspended in a 4% FBS/1×PBS solution containing 40 μM DFHBI-1T and kept on ice until analysis on the FACSAriaII (BD Biosciences). The untransfected cells are a negative control. Transfected cells were analyzed and sorted based on green fluorescence (ex=488 nm, em=525±50 nm). Processing and analysis of the data was performed in the FlowJo program (Tree Star).

Circular SAM Sensor Design and in-Gel Activation: Transducer variants of Broccoli-SAM aptamer fusions were cloned into the pAV-U6+27-Tornado vector for circRNA expression. Two days after transfection of these plasmids and the plasmid for circular Broccoli into HEK293T cells, Actinomycin D was added to cells, which were then harvested and the RNA extracted, as described above. Isolated RNAs from cells treated or untreated with Actinomycin D were separated using 6% or 10% denaturing PAGE, and the gels were imaged using DFHBI-1T followed by SYBR Gold staining.

Activation of the sensors' fluorescence in the PAGE gel was detected by first staining first with the standard in-gel Broccoli imaging buffer. After imaging, 1 μM of S-adenosyl-methionine (Sigma, A7007) was added to the imaging buffer and stained the gels for an additional 30 minutes and imaging the signal again. This was repeated 3 more times after progressively adjusting S-adenosyl-methionine concentrations to 10, 100, and 1000 μM. Transducer variants signals were compared at each concentration after normalizing to the signal for circular Broccoli in each image.

Intracellular SAM Imaging and Quantification: HEK293T cells were transfected with Tornado plasmids encoding either the circular SAM sensor with transducer 1 or circular Broccoli. Two days later, these cells were subcultured onto coated glass bottom plates as described above and imaged the next day. Using live cell conditions described above, cells were imaged before and for 3 hours after adding cycloleucine (Sigma, A48105) to 100 mM at 5 minute intervals. Then, cycloleucine was withdrawn and cells were imaged every 5 minutes for 3 additional hours. ImageJ was used for processing images and for measure the total cell fluorescence at each time point.

Example 1—Concept of RNAs that Autocatalytically Become Substrates for RNA Ligation In order to develop a system for efficient RNA circularization, an endogenous RNA ligase that would ligate the 5' and 3' ends of an RNA sequence of interest was first identified. A system for generating circular RNA that takes advantage of an RNA ligation step that occurs during tRNA maturation was previously described (FIG. 1A) (Lu et al., "Metazoan tRNA Introns Generate Stable Circular RNAs In Vivo," *RNA* 21(9):1554-65 (2015), which is hereby incorporated by reference in its entirety). A subset of tRNAs contain an intron within the anti-codon-loop that is removed by a tRNA-specific endonuclease (Abelson et al., "tRNA Splicing," *J Biol. Chem.* 273:12685-12688 (1998), which is hereby incorporated by reference in its entirety). The exon ends that are created by endonucleolytic cleavage of the intron are then ligated by RtcB, resulting in the formation of the mature tRNA. In addition, the released intron also contains ends that can be ligated by RtcB, resulting in a circular intron.

This "tricY" system (Lu et al., "Metazoan tRNA Introns Generate Stable Circular RNAs In Vivo," *RNA* 21(9):1554-65 (2015), which is hereby incorporated by reference in its entirety) based on the splicing of a human tRNA$^{Tyr}$ was used to express circular aptamers in mammalian cells. To do so, the fluorogenic aptamer Broccoli was inserted into the intron sequence (Filonov et al., "Broccoli: Rapid Selection of an RNA Mimic of Green Fluorescent Protein by Fluorescence-Based Selection and Directed Evolution," *J. Am. Chem. Soc.* 136(46):16299-308 (2014), which is hereby incorporated by reference in its entirety). As a result, when the intron is released from the tRNA precursor it can be circularized by RtcB. However, the accumulation of circular Broccoli was relatively low. This could either be due inefficient ligation of the intron by RtcB or inefficient endonucleolytic cleavage of this modified tRNA substrate. As a result, the RNA is degraded before it can become a substrate for RtcB.

Figure 1B:
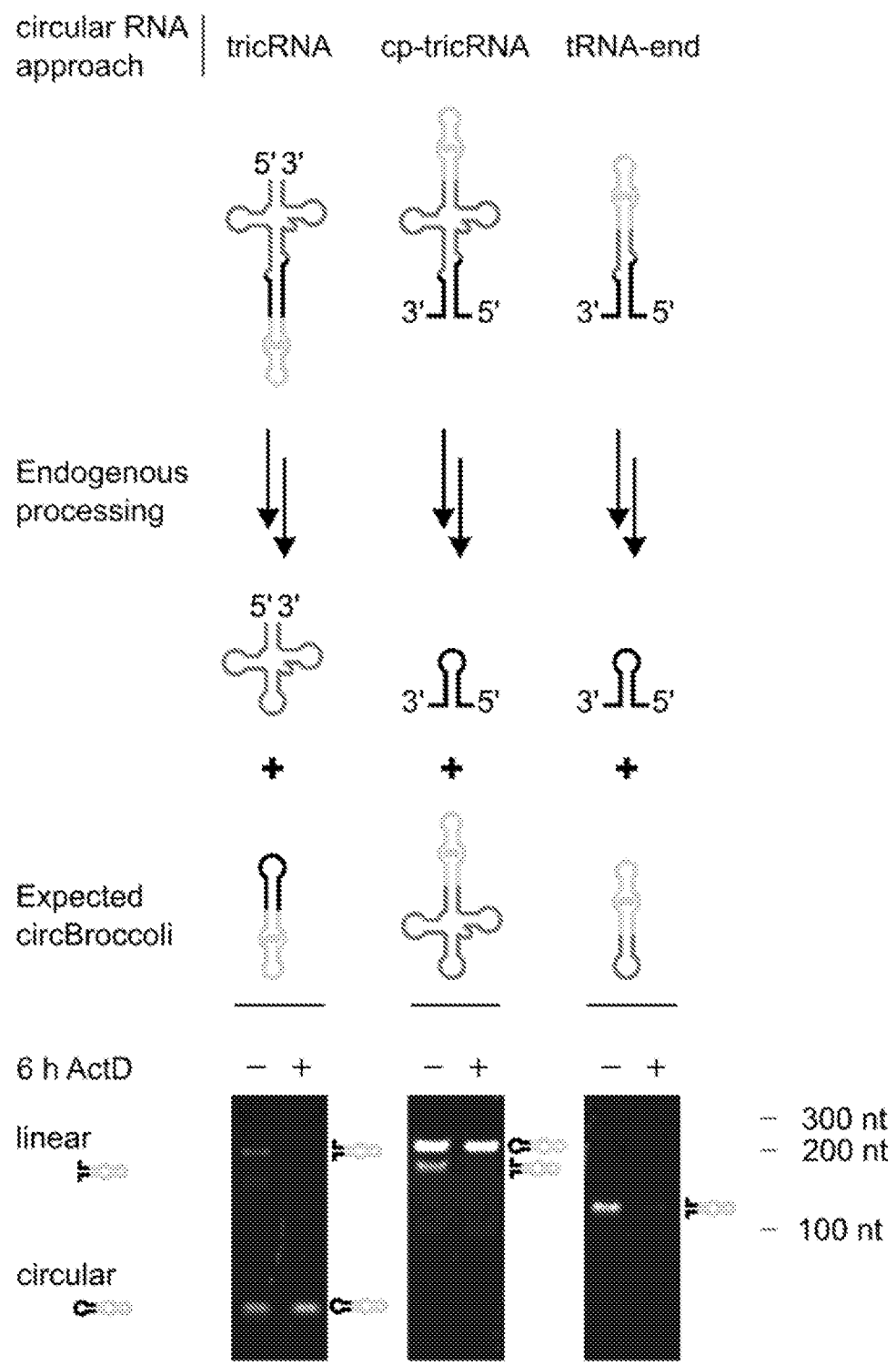

Initially, achieving higher circular aptamer expression from the exon of the pre-tRNA rather than from its intron sequence was attempted. Since production of mature tRNA depends on ligation of the exons rather than the introns, it was expected that the exons would be effective target sequences for ligation by RtcB to generate a circular RNA. This design required a "circular permutation" of the pre-tRNA, wherein the sequence of an RNA is rearranged without making changes to the overall structure. In this process, a new pair of 5' and 3' ends are created by splitting the sequence in two within the intron loop, and then joining the original 5' and 3' ends into a new loop. Expression of this RNA with Broccoli in this new loop produced circular Broccoli at 4-fold higher levels than when expressing Broccoli in the intron sequence. (FIG. 1B). Despite this improvement, similarly high levels of unprocessed tRNA were observed, suggesting that the endogenous endonucleolytic activity does not efficiently process Broccoli-containing pre-tRNAs.

Therefore a strategy to increase the efficiency of transcript processing into a substrate for RtcB was devised. The tRNA is processed by a tRNA endonuclease that creates unique ends on RNA: (1) at the 5' end, the endonuclease leaves a 5' hydroxyl, rather than the 5' phosphate seen with most other endonucleases; (2) at the three prime end, the tRNA endonuclease leaves a 2',3'-cyclic phosphate, rather than the more common 3' hydroxyl. The 5' hydroxyl and 2',3'-cyclic phosphate at the 3' end are the substrates for RtcB-mediated ligation. To make this process more efficient, it was desirable to bypass the tRNA endonuclease and generate these ends with high efficiency inside cells.

Notably, all known ribozymes undergo self-cleavage that leaves 5' hydroxyl and 2',3'-cyclic phosphate ends (Ferré-D'Amaré et al., "Small Self-Cleaving Ribozymes," *Cold Spring Harbor Perspectives in Biology* 2:1-11 (2010) and Roth et al., "A Widespread Self-Cleaving Ribozyme Class is Revealed by Bioinformatics," *Nat. Chem. Biol.* 10:56-60 (2014), which are hereby incorporated by reference in their entirety). Thus, expressing RNA transcripts containing ribozymes that would autocatalytically process themselves to produce 5' hydroxyl and 2',3'-cylic phosphate ends was considered. Most ribozymes show cleavage rates that require tens of minutes or even hours for the cleavage to go to completion. However, several recently discovered classes of ribozymes were described with exceptionally high cleavage rates and have reduced dependence on divalent cations (Roth et al., "A Widespread Self-Cleaving Ribozyme Class is Revealed by Bioinformatics," *Nat. Chem. Biol.* 10:56-60 (2014) and Weinberg et al., "New Classes of Self-Cleaving Ribozymes Revealed by Comparative Genomics Analysis," *Nat. Chem. Biol.* 11:606-610 (2015), which are hereby incorporated by reference in their entirety). In particular, the class of "Twister" ribozymes are estimated to perform cleavage 1000-fold faster than hammerhead ribozymes and can even self-cleave in the absence of divalent cations (Roth et al., "A Widespread Self-Cleaving Ribozyme Class is Revealed by Bioinformatics," *Nat. Chem. Biol.* 10:56-60 (2014), which is hereby incorporated by reference in its entirety). Their cleavage rate is so fast that initially, it could only be measured in suboptimal buffer conditions. It was therefore reasoned that RNAs containing these ribozymes on either end could efficiently and autocatalytically generate the substrate ends for RtcB-mediated ligation before the RNA is degraded. Formation of the ends would be rapid, bypassing the rate-limiting step of enzymatic endoribonucleolytic cleavage. Thus, ribozymes that leave RtcB-compatible ends on either end of an RNA would enable RtcB to generate circular RNAs in cells.

Example 2—Selection of Ribozymes for Autocatalytic Generation of RtcB-Compatible Ends Different pairs of ribozymes were tested to see which combinations efficiently process the RNA to contain a 5' hydroxyl and a 2',3'-cyclic phosphate. Ribozymes that would produce a 2',3'-cyclic phosphate on the transcript's 3' end after cleavage were first selected. Many ribozymes cleave at internal sites and would therefore leave a large ribozyme-derived remnant attached to the transcript (Weinberg et al., "New Classes of Self-Cleaving Ribozymes Revealed by Comparative Genomics Analysis," *Nat. Chem. Biol.* 11:606-610 (2015), which is hereby incorporated by reference in its entirety). It was desirable to leave a minimal residual sequence on the transcript following cleavage. Therefore, 3'-end ribozymes that produce cleavage sites near the ribozyme's 5' end were selected. This would result in a small ribozyme-derived remnant on the RNA. The recently discovered Hatchet ribozyme (derived from a metagenomic sequence) (Weinberg et al., "New Classes of Self-Cleaving Ribozymes Revealed by Comparative Genomics Analysis," *Nat. Chem. Biol.* 11:606-610 (2015), which is hereby incorporated by reference in its entirety) and a type P1 Twister ribozyme (*O. sativa* Osa-1-4) (Liu et al., "Crystal Structure and Mechanistic Investigation of the Twister Ribozyme," *Nat. Chem. Biol.* 7:1-7 (2014), which is hereby incorporated by reference in its entirety) were selected, both of which cleave near the ribozyme's 5' end.

Next, ribozymes that would produce a 5' hydroxyl on the transcript's 5' end after cleavage were selected. In this case, the ribozyme needs to cleave near its 3' end in order to leave a small ribozyme-derived remnant in the RNA. Several high efficiency ribozymes cleave near the 3' end, including a type P3 Twister from *N. vectensis* (Roth et al., "A Widespread Self-Cleaving Ribozyme Class is Revealed by Bioinformatics," *Nat. Chem. Biol.* 10:56-60 (2014), which is hereby incorporated by reference in its entirety), Twister Sister 3 and 4 (Weinberg et al., "New Classes of Self-Cleaving Ribozymes Revealed by Comparative Genomics Analysis," *Nat. Chem. Biol.* 11:606-610 (2015), which is hereby incorporated by reference in its entirety); additionally, the recently characterized Pistol ribozyme from (M4 construct from *L. sphaericus*) (Weinberg et al., "New Classes of Self-Cleaving Ribozymes Revealed by Comparative Genomics Analysis," *Nat. Chem. Biol.* 11:606-610 (2015) and Harris et al., "Biochemical Analysis of Pistol Self-Cleaving Ribozymes," *RNA* 21:1852-1858 (2015), which is hereby incorporated by reference in its entirety) and a type I Hammerhead ribozyme containing the consensus catalytic core (Uhlenbeck, O. C., "A Small Catalytic Oligoribonucleotide," *Nature* 328:596-600 (1987), which is hereby incorporated by reference in its entirety) were included.

Figure 2:
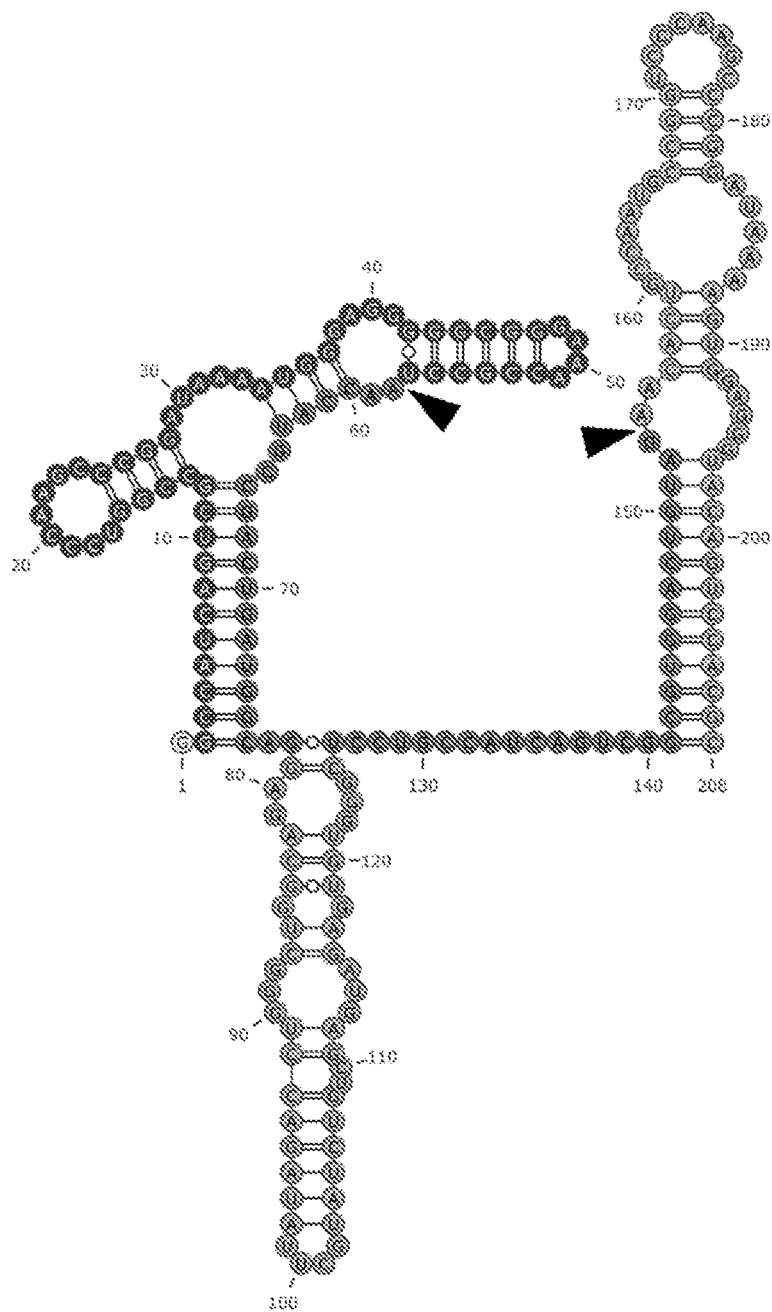
FIG. 2 is an illustration showing an example of the sequences of a transcribed RNA prior to cleavage by 5' and 3' ribozymes. This construct contains sequences of a 5' P3 Twister U7A ribozyme (bases 2-57) and a 3' P1 Twister ribozyme (bases 154-208) that flank two ligation sequences (bases 58-78 and 126-153) with an internal effector sequence (bases 79-125). Following cleavage by both ribozymes (at positions marked in black), the ligation sequences contain 5'-OH and 2',3'-cyclic phosphate modifications and form a stem that is a substrate for RtcB. Once the RNA has been ligated by RtcB, the RNA becomes circular and contains the effector sequence of RNA.

Two sequences were designed between each ribozyme's internal cleavage site and the RNA of interest. After cleavage, the 5' and 3' ends sequences left by each ribozyme on the transcript should become base paired to promote their ligation by RtcB. In the case of tRNA processing, the intermediate tRNA anticodon stem approximates the 5' hydroxyl and 2',3'-cyclic phosphate for ligation by RtcB (Popow et al., "HSPC117 is the Essential Subunit of a Human tRNA Splicing Ligase Complex," *Science* 331:760-4 (2011) and Chakravarty et al., "RNA Ligase RtcB Splices 3'-Phosphate and 5'-OH ends via Covalent RtcB-(Histidinyl)-GMP and Polynucleotide-(3')pp(5")G Intermediates." *Proc. Natl. Acad. Sci.* 109:6072-6077 (2012), which are hereby incorporated by reference in their entirety). Therefore, each strand of this intermediate anticodon stem was chosen to act as "ligation sequences" that resemble the native substrate of RtcB. An additional 12-bp near the RNA of interest were included to promote stem formation after ribozyme cleavage (FIG. 2).

Furthermore, mutations to each ribozyme were made so that setting the 5' or 3' ligation sequence within the ribozyme does not disrupt the efficiency of ribozyme cleavage. The smaller piece of each wild type ribozyme that would remain after cleavage with the corresponding 5' or 3' ligation sequence was replaced. Then, the appropriate mutations elsewhere in the ribozyme were made to preserve conserved Watson-Crick base-pairing. For the twister ribozyme, it has been shown that mutants which preserve Watson-Crick base-pairing do not significantly diminish cleavage activity (Kobori et al., "High-Throughput Mutational Analysis of a Twister Ribozyme," *Angew. Chemie—Int. Ed.* 55:10354-10357 (2016), which is hereby incorporated by reference in its entirety). Overall, there were no highly specifically conserved positions in any ribozyme that had to be mutated. However, there was one position in the P3 Twister that is 97% conserved as A, which was converted into a U when adding the 5' ligation sequence (Roth et al., "A Widespread Self-Cleaving Ribozyme Class is Revealed by Bioinformatics," *Nat. Chem. Biol.* 10:56-60 (2014)), which is hereby incorporated by reference in its entirety). This position does not base-pair and is near to the catalytic site of the ribozyme. Thus, a second version of the P3 Twister ribozyme in the group of 5' ribozymes wherein the 5' ligation sequence contains a U to A mutation (U7A) to help promote cleavage was made.

Figure 3:
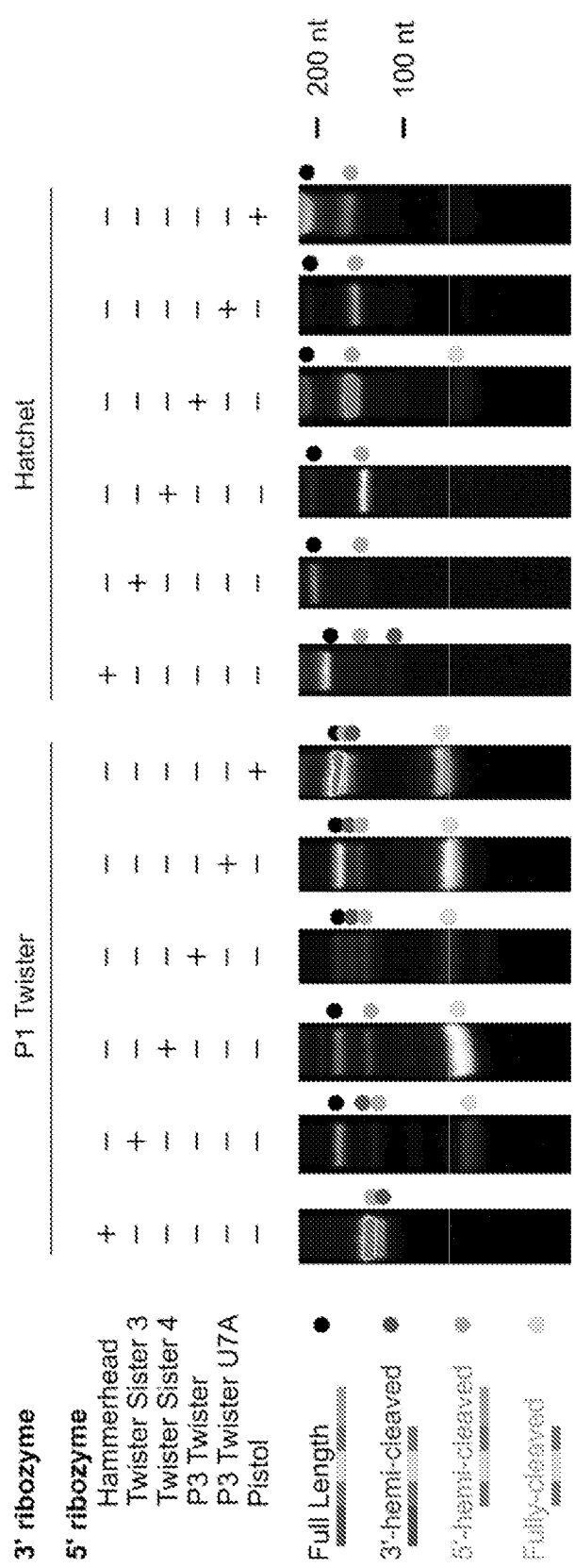
FIG. 3 is a chart showing constructs of all pairwise combinations of the two 3' ribozymes and the six 5' ribozymes are compared for how much fully-cleaved RNA is generated. RNAs are transcribed for 2 hours and then quenched before separating on a denaturing 10% polyacrylamide gel. The gel is stained with DFHBI-1T, which binds to Broccoli and creates fluorescence. All constructs contain Broccoli as an effector, and the Broccoli-containing bands pertaining to full-length, 3'- and 5'-hemi-cleaved, and fully-cleaved RNA are identified according to expected RNA size. Constructs generating fully-cleaved RNA require a P1 Twister on the 3' end and generate the most product when containing a Twister Sister 4, P3 Twister U7A, or Pistol on the 5' end. Other constructs generate much lower amounts of the fully-cleaved RNA.

Then, the ability of each pairwise combination of 5' and 3' ribozymes to cleave themselves after incorporation into an RNA transcript was measured. Constructs containing Broccoli, flanked by the ligation sequences, with one 5' ribozyme and one 3' ribozyme were transcribed and cleavage of both ribozymes was assessed by examining the size of the RNA. Since the RNA contains the Broccoli aptamer, it can be readily detected after denaturing gel electrophoresis by staining with DFHBI, a dye whose fluorescence is activated by binding Broccoli (FIG. 3). Accumulation of the "fully-cleaved" RNA product where both ribozymes are cleaved off is highest with the P1 Twister at the 3' end, especially when the 5' ribozyme was a P3 Twister, a Twister Sister, or Pistol ribozyme (FIG. 3). The P3 Twister construct generated substantially more fully-cleaved product when the U7A mutation was included. As the P1 Twister and P3 Twister U7A construct is transcribed over time (FIG. 4B), the fully-cleaved product and the side products of ribozyme cleavage rapidly accumulate. A constant level of RNA where only one ribozyme cleaved was observed, suggesting that both Twisters cleave efficiently throughout the reaction. Thus, 3' P1 Twister constructs containing any version of the Twister, Twister Sister, or Pistol ribozymes on the 5' end generated the fully-cleaved product in vitro.

Whether the fully cleaved product contains the 5' hydroxyl and 2',3'-cyclic phosphate ends are required by RtcB for ligation was next examined. In the absence of RtcB, the RNA migrated as a linear species. However, incubation with RtcB resulted in a faster migrating band (FIG. 4C), consistent with a known property of circular RNAs (Tabak et al., "Discrimination Between RNA Circles, Interlocked RNA Circles and Lariats Using Two-Dimensional Polyacrylamide Gel Electrophoresis," *Nucleic Acids Res.* 16:6597-6605 (1988), which is hereby incorporated by reference in its entirety), suggesting that it contained the 5'-hydroxyl and 2',3'-cyclic phosphate ends required by RtcB. Pre-treatment with T4 polynucleotide kinase, which changes the end modifications to a 5'-phosphate and 3'-hydroxyl, did not result in an observed shift in gel mobility after reaction with RtcB. Therefore, RNA that has been fully cleaved by ribozymes on both ends is capable of becoming circularized by RtcB.

Example 3—Ribozyme-Flanked Transcripts are Circularized in Cells

Having observed which pairs of 5' and 3' ribozymes cleave most effectively in vitro, which of these transcripts cleave and circularize efficiently in cells was next evaluated. Each construct was encoded in a vector designed for transcription of small RNAs by polymerase III off of a U6 promoter (Paul et al., "Localized Expression of Small RNA Inhibitors in Human Cells," *Mol. Ther.* 7:237-247 (2003), which is hereby incorporated by reference in its entirety). HEK293T cells were transfected with these plasmids. For each construct, the level of Broccoli RNA was measured by resolving whole cellular RNA on a denaturing gel and subsequently staining the gel in urea-free buffer containing DFHBI-1T. As a preliminary test to determine whether the RNA was circular, levels of the Broccoli-fluorescent RNA was measured before and after 6 hours of actinomycin D treatment. This cellular treatment was previously found to result in the complete loss of non-circularized aptamers due to their rapid degradation, while aptamers that were circularized showed no change in expression with this treatment (Lu et al., "Metazoan tRNA Introns Generate Stable Circular RNAs In Vivo," *RNA* 21(9):1554-65 (2015), which is hereby incorporated by reference in its entirety).

Figure 4A:
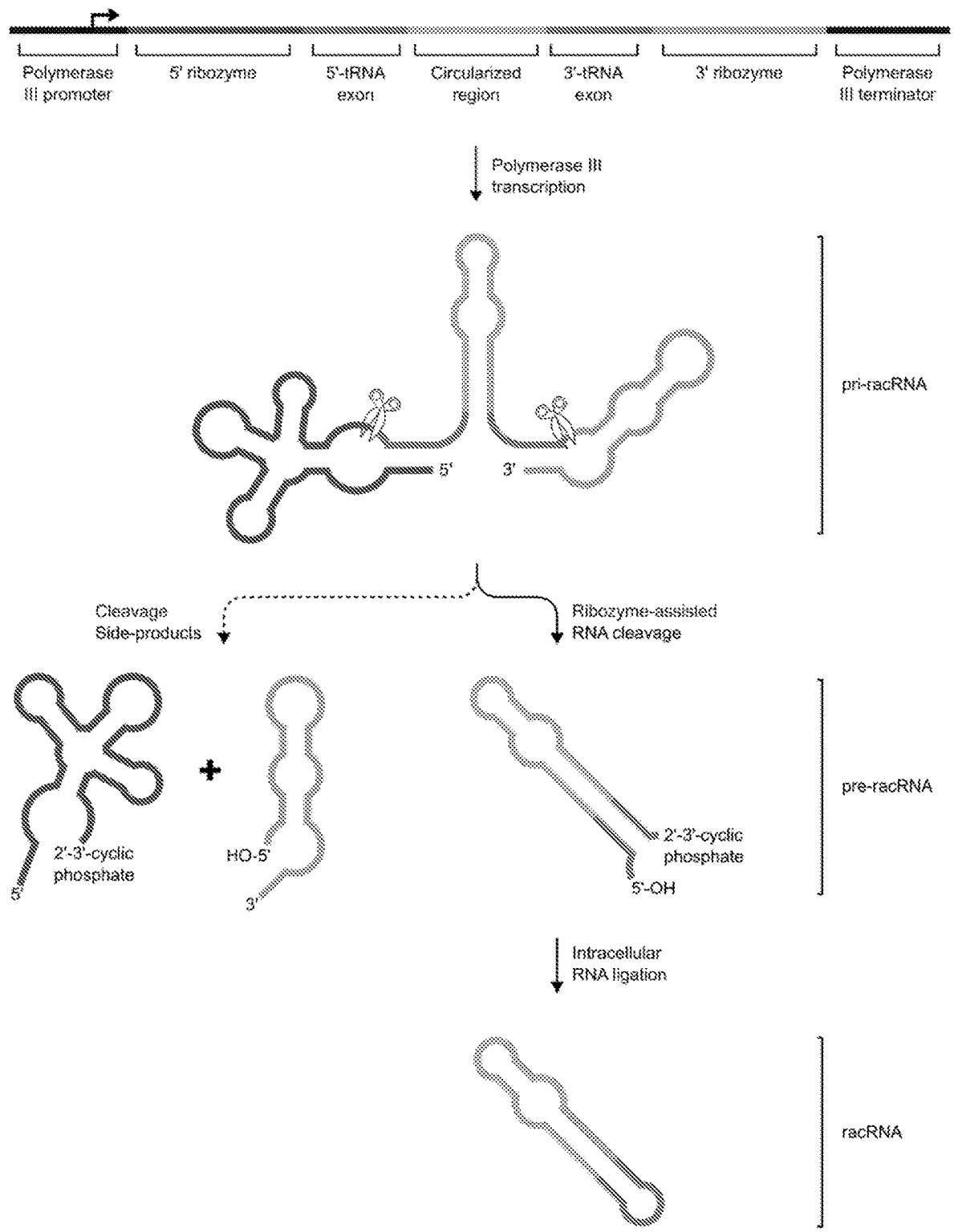

Notably, transcripts containing a 5' P3 Twister U7A and a 3' P1 Twister showed the highest level of Broccoli RNA expression with no detected side-products (FIG. 4D). Additionally, this expression was insensitive to actinomycin D treatment, consistent with the idea that these are circular Broccoli transcripts. This version of the circular RNA expression system was named "Tornado" because it contains two Twister ribozymes. The circular Broccoli expressed using the tRNA-intron-based system was markedly lower in expression compared to that generated by the Tornado expression system.

Figures 4E, 4F, 4G:
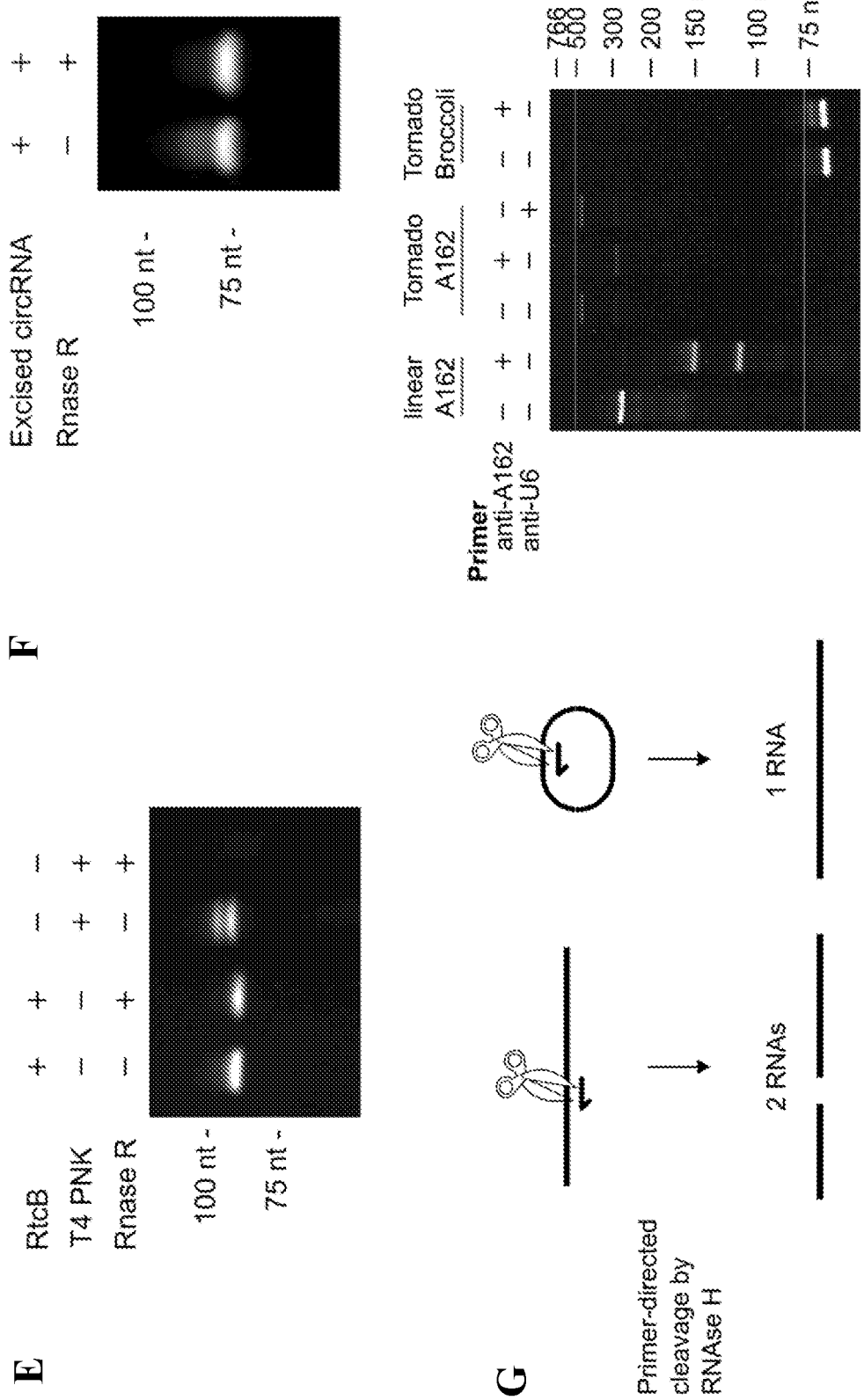
Figure 5:
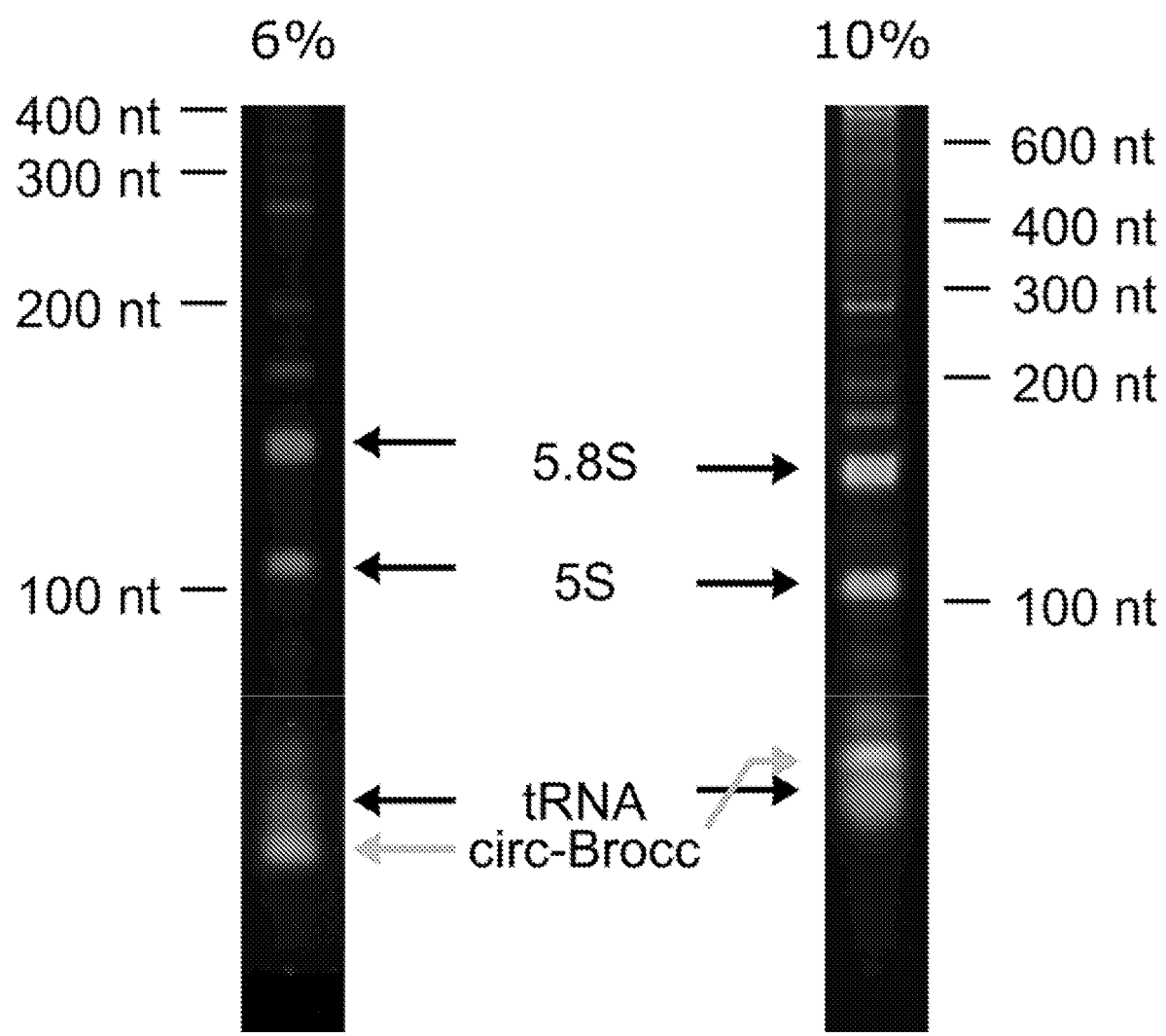
FIG. 5 shows that the stable Broccoli band migrates like a circular RNA by PAGE in different percentage acrylamide gels. The stable Broccoli-containing band expressed by Tornado migrates at an unusual rate that depends on the gel percentage. In a 6% polyacrylamide gel, it runs faster than tRNA, but in a 10% polyacrylamide gel, it runs more slowly than tRNA. This characteristic is also found for known circular RNAs, suggesting that the Broccoli-containing band is indeed a circular RNA that contains Broccoli (circ-Brocc). Gels have been imaged using SYBR-Gold and the circ-Brocc is identified using a DFHBI-1T stain for Broccoli. 10% polyacrylamide gel image has been elongated to better compare migration of bands.

Next, whether this abundant and stable Broccoli-containing RNA species behaved like a circular RNA was investigated. Several approaches were used to determine whether this RNA had the properties of a circular RNA. As a first test, whether the RNA was sensitive to RNase R, an exoribonuclease that requires a 5' end, was tested. Notably, after excising the stable Broccoli band from the gel, and purifying the RNA, it was found that this RNA was not susceptible to RNase R-mediated degradation (FIG. 4F). In contrast, a control Broccoli RNA transcribed in vitro was completely degraded by RNase R. As a second approach, whether this stable Broccoli RNA runs at different rates of mobility at different densities of polyacrylamide, which is characteristic of circular RNA, was examined. As has been seen for other circular RNAs (Tabak et al., "Discrimination Between RNA Circles, Interlocked RNA Circles and Lariats Using Two-Dimensional Polyacrylamide Gel Electrophoresis," *Nucleic Acids Res.* 16:6597-6605 (1988); Zaug et al., "The Intervening Sequence Excised from the Ribosomal RNA Precursor of Tetrahymena Contains a 5-terminal Guanosine Residue Not Encoded by the DNA," *Nucleic Acids Res.* 10(9):2823-2838 (1982); and Ruskin et al., "Excision of an Intact Intron as a Novel Lariat Structure During pre-mRNA Splicing In Vitro," *Cell* 38:317-331 (1984), which is hereby incorporated by reference in its entirety), this stable Broccoli species runs anomalously slowly in a 10% gel as compared to a 6% gel (FIG. 5). Together, these data suggest that the stable Broccoli band that was expressed via the Tornado expression system has several characteristics of a circular RNA.

Next, a definitive approach was used to test for circularity by site-specifically cleaving the stable Broccoli RNA. RNase H selectively cleaves RNA that is hybridized to DNA, allowing a complementary DNA oligonucleotide to direct RNase H cleavage to a specific sequence. If a RNA is linear, then the sequence-directed cleavage by RNase H would produce two products. However, as shown previously (Ruskin et al., "Excision of an Intact Intron as a Novel Lariat Structure During pre-mRNA Splicing In Vitro," *Cell* 38:317-331 (1984) and Capel et al., "Circular Transcripts of the Testis-Determining Gene Sry in Adult Mouse Testis," *Cell* 73:1019-1030 (1993), which is hereby incorporated by reference in its entirety), if an RNA is circular, then RNase H cleavage would produce a single product that runs with a normal migration pattern. The stable Broccoli RNA was incubated with RNase H and a 15-nucleotide-long DNA oligonucleotide designed to hybridize to a sequence within this RNA. This reaction generated a single major band that migrated at 275 nucleotides (FIG. 4G), consistent with the expected migration of the linear product.

As a control, the linear form of the circular Broccoli (that was expected to be expressed from the Tornado expression system) was in vitro transcribed. This RNA was synthesized without the twister ribozymes, and was not treated with RtcB, and is therefore a linear RNA. When this RNA was treated with RNase H and the DNA oligonucleotide, it generated two bands (FIG. 4G), at sizes consistent with the site-specific cleavage of the linear RNA. This conclusively shows that the stable Broccoli RNA generated by the Tornado expression system is indeed circular, and not merely an unusually stable linear RNA.

Example 4—the Tornado Expression System Generates Circularizes Aptamers in Diverse Cells at High Efficiency Levels of circular RNA generated in the Tornado expression system were compared with other RNA aptamer expression methods. Expression of linear Broccoli in HEK293T cells produces very dim green fluorescence (FIG. 6B) at the short exposure time used in this experiment (200 ms). With the same U6 promoter and exposure time, fluorescence was only slightly detected in cells expressing Broccoli using the tricY system. However, the cells were highly green fluorescent when expressing circular Broccoli generated from the Tornado expression system. The robust green fluorescence was consistent with the high level of circular Broccoli detected by gel staining (FIG. 4D). These data support the idea that the Tornado expression system produces high levels of circular RNA and further demonstrates that the aptamers adopt a functional conformation when expressed in this manner.

Figure 6A:
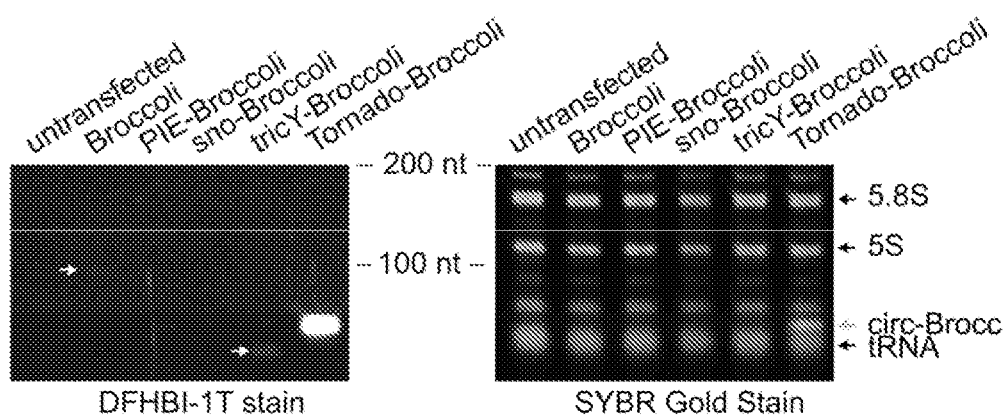
FIGS. 6A-6E show abundant circRNA expression in different cell lines with fluorogenic aptamers.
Figure 6B:
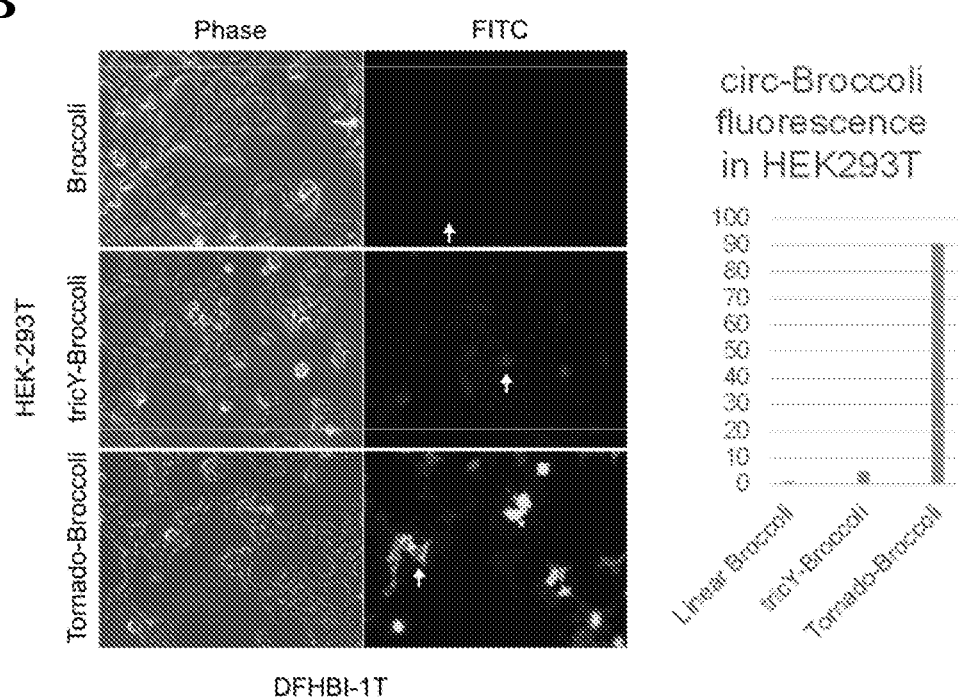
Figure 6C:
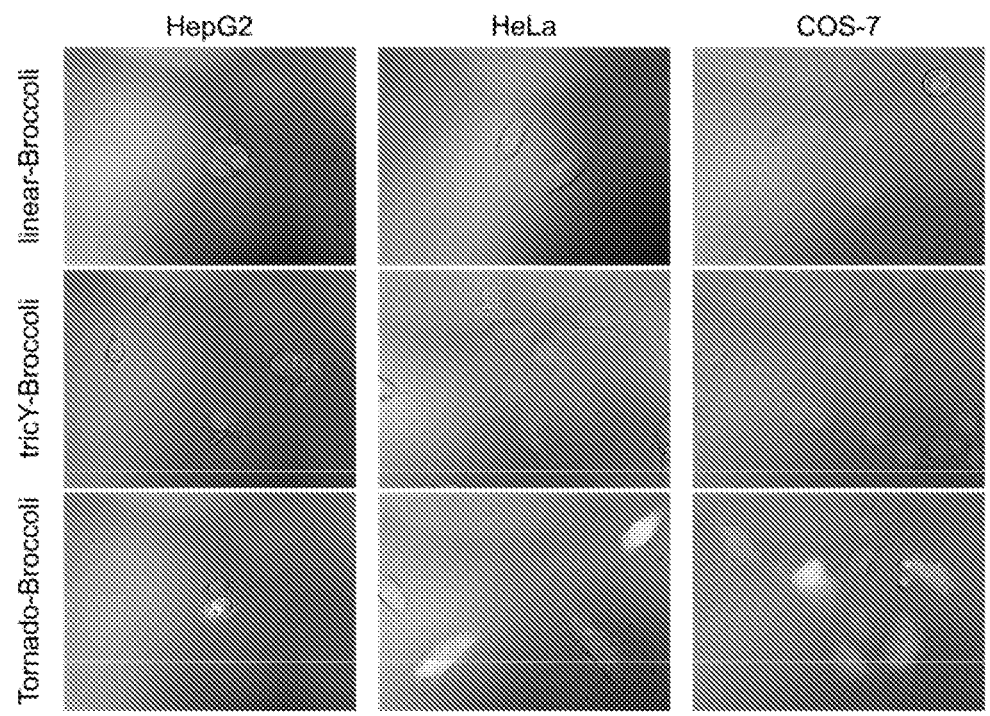
Figure 6D:
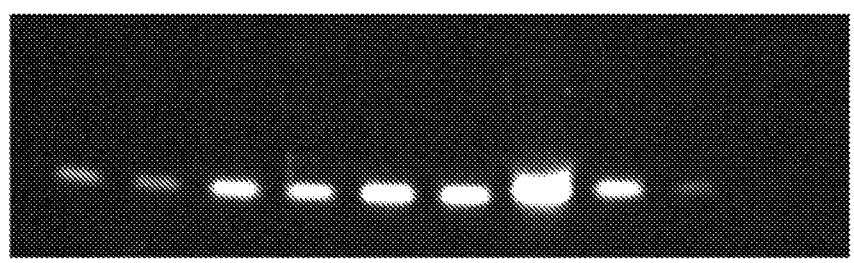

Whether RNA circularization by the Tornado expression system could be elicited in diverse types of mammalian cells was next examined. To test this, circular Broccoli was expressed using the Tornado expression system in three additional cell lines: COS-7, HeLa, and HepG2. In each case, bright green fluorescence was readily detected in transfected cells (FIG. 6C), while it was not observed for linear or tricY expression of Broccoli. Cellular RNA was resolved by denaturing gel electrophoresis and staining with DFHBI-1T. In each case, a circular RNA band was detected at the same migration seen in HEK293T cells (FIG. 6D). Thus, circular RNA can be expressed by Tornado in diverse cell types.

Figure 6E:
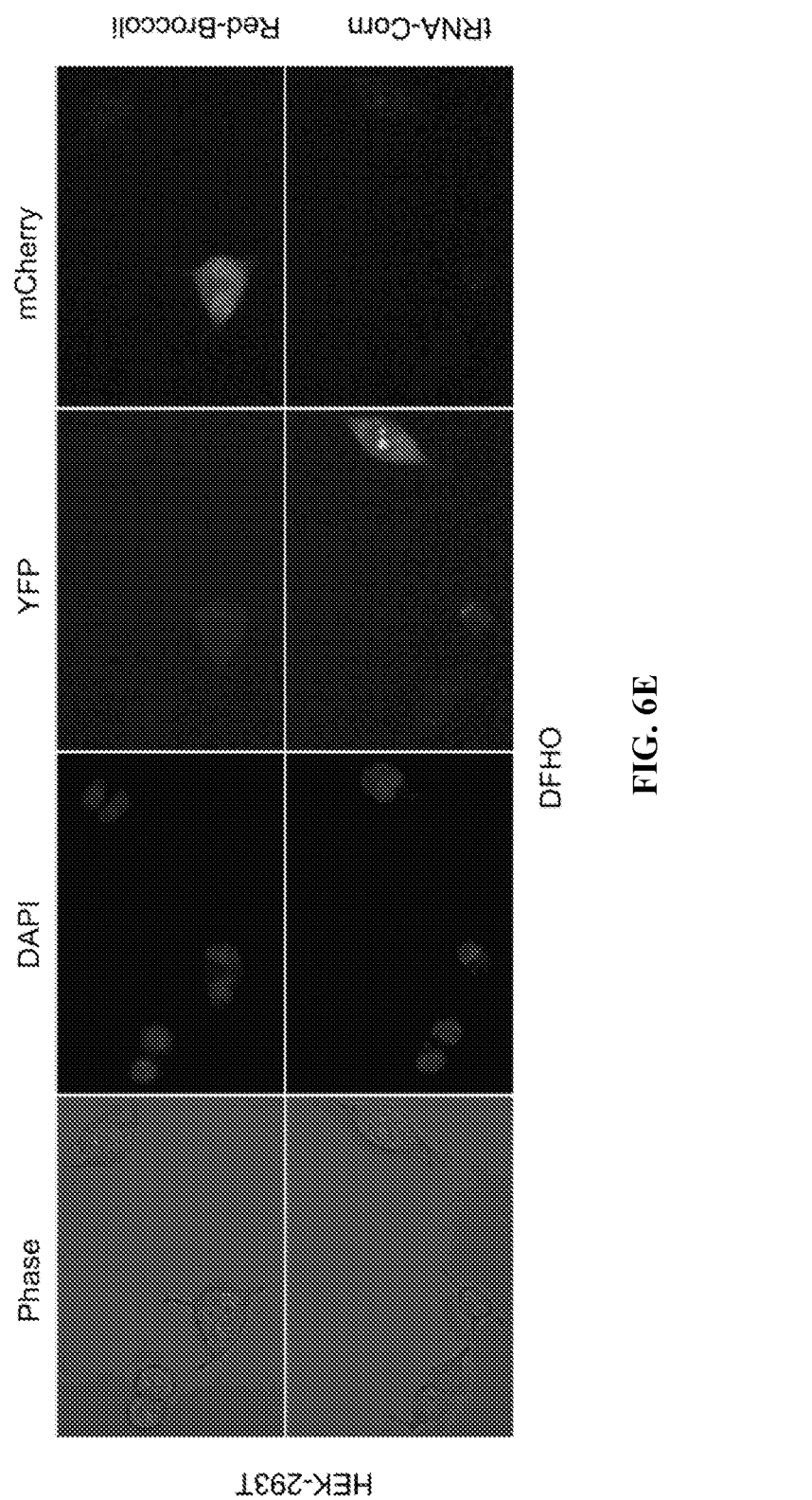

Lastly, whether other aptamers besides Broccoli can be processed into circular RNAs when expressed using the Tornado system was next examined. The Corn aptamer, a recently described fluorogenic RNAs that activates the yellow fluorescence of a chromophore (DFHO) that mimics the one found in red fluorescent proteins (Song et al., "Imaging RNA Polymerase III Transcription Using a Photostable RNA-Fluorophore Complex," *Nat. Chem. Biol.* 13:1187-1194 (2017), which is hereby incorporated by reference in its entirety) was expressed. The Red-Broccoli that binds to the same chromophore as Corn, but produces red fluorescence (Song et al., "Imaging RNA Polymerase III Transcription Using a Photostable RNA-Fluorophore Complex," *Nat. Chem. Biol.* 13:1187-1194 (2017), which is hereby incorporated by reference in its entirety) was also expressed. Expression of the Corn and Red-Broccoli aptamers using the Tornado system resulted in robust fluorescence that was visualized using short exposure times (FIG. 6E). This fluorescence was resistant to actinomycin D treatment for six hours, consistent with the idea that these are highly stable circular RNAs. In contrast, the linear Red-Broccoli and Corn transcript was not detected when imaged at these short exposure times. Thus, the Tornado expression system can potentially express diverse types of RNA aptamers in functional and folded conformations.

Example 5—Tornado-Expressed Circular Aptamers are Among the Highest Expressed RNAs in Cells The overall expression of the circular RNA in cells was next quantified. As a first test, whole cellular RNA was purified from cells expressing circular Broccoli from the Tornado expression system. The RNA was resolved on a denaturing gel, and stained with either DFHBI-1T or SYBR Gold to visualize all RNA. As before, the Broccoli-containing circular RNA generated from the Tornado was readily detected when the gel was stained with DFHBI-1T (FIG. 6A). Broccoli expressed using other circular RNA expression systems, as well as the linear Broccoli RNA expressed from the U6 promoter were considerably lower intensity. When the cellular RNA was stained with SYBR Gold, the abundant cellular RNAs such as tRNA, 5S and 5.8S RNA were readily detectable. However, in RNAs from cells expressing circular Broccoli using the Tornado expression system, an additional band of equal intensity to the 5.8S band, and greater intensity than the 5S band was detected. This band was clearly circular Broccoli, based on its mobility and its appearance only in cells transfected with Tornado expression system. Thus, Tornado produces circular RNA that matches the levels of stable and highly-expressed endogenous cellular RNAs.

To determine the intracellular concentration of circular Broccoli, in vitro transcribed RNA standards were utilized. These standards comprised the same sequence as the circular Broccoli, but were linear. These standards were loaded at defined amounts in the gel, and were used to quantify the amount of circular Broccoli transcript derived from lysates. Lysates were prepared from a known number of cells with a measured estimated average volume. Based on this analysis (FIG. 6D), circular Broccoli expression was calculated to be 13 µM in HEK293T cells, 21 µM in HeLa cells, and 3 µM in HepG2 cells. This further supported that Tornado-expressed RNAs are very highly expressed and achieve much higher expression than any other circular RNA expression system.

Example 6—Circular Broccoli Constructs do not Activate Apoptosis or an Innate Immunity Response Whether expressing circular Broccoli results in cellular cytotoxicity was next investigated. Circular RNAs are already known to be expressed in cells (Jeck et al., "Circular RNAs are Abundant, Conserved, and Associated With ALU Repeats," RNA 19:141-57 (2013), which is hereby incorporated by reference in its entirety), therefore, these circles may not be recognized as foreign. To test this idea, the cytotoxicity of linear and circular Broccoli was examined. In these experiments, linear Broccoli or circular Broccoli were expressed using the Tornado expression system, both from the same U6 promoter. Levels of apoptosis were measured at two, four, and eight days following transfection of HEK293T cells. No statistically significant difference in the apoptosis level as measured by the percent of cells showing annexin-V staining at any time point were observed.

As an additional test, whether the expression of the circular Broccoli affected growth rates was also examined. To test this, circular Broccoli was expressed using the Tornado expression system. Growth curves of the circular Broccoli-expressing cells were plotted. In these experiments, cells were transfected, and three days later, they were split at low dilution in order to monitor cell growth rates. No statistically significant decrease in the growth rate of the green fluorescent cells expressing the circular Broccoli aptamer compared to mock transfected cells which exhibited no fluorescence.

Lastly, whether expression of circular Broccoli activates an innate immunity response that is commonly seen with foreign RNA and recently with foreign circular RNA (Chen et al., "Sensing Self and Foreign Circular RNAs by Intron Identity," Mol. Cell 67(2):228-238 (2017), which is hereby incorporated by reference in its entirety) was evaluated. These responses typically involve the RIG-I or MDA5 nucleic acid sensors. The 5'-triphosphate "panhandle" produced by viral polymerases activates RIG-I, while sequences containing long double-stranded RNAs activate MDA5 (Hornung et al., "5'-Triphosphate RNA is the Ligand for RIG-I," Science 314:994-997 (2006) and Kato et al., "Length-Dependent Recognition of Double-Stranded Ribonucleic Acids by Retinoic Acid-Inducible Gene-I and Melanoma Differentiation-Associated Gene 5," J. Exp. Med. 205:1601-1610 (2008), which is hereby incorporated by reference in its entirety). The small circular RNAs that we expressed using Tornado contain neither of these structural features.

Figure 7:
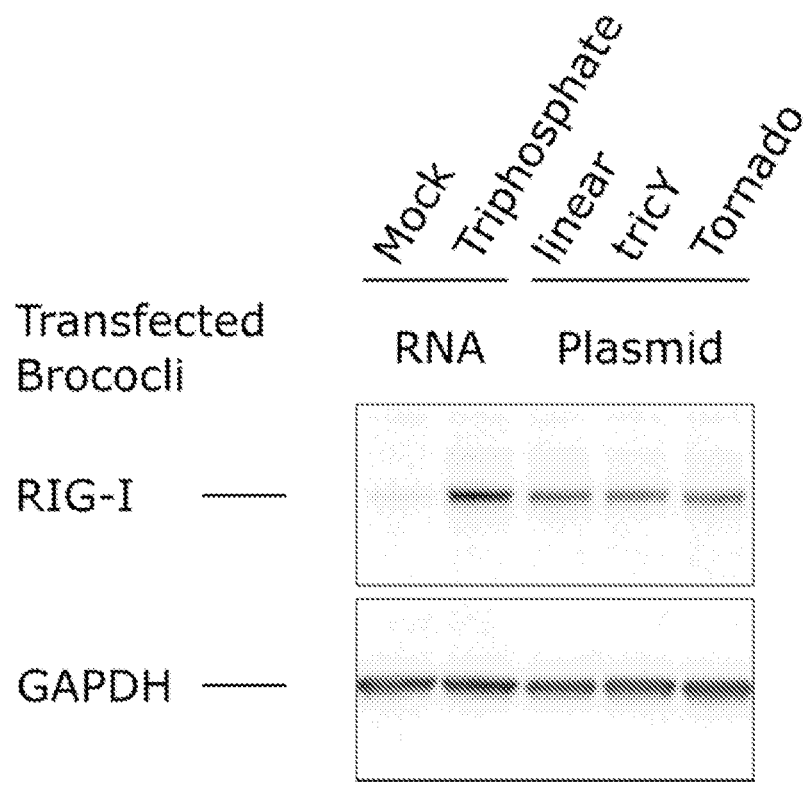
FIG. 7 shows that expression of circular RNA by Tornado does not activate the innate immune response. RIG-I levels reflect activation of the innate immune response. RIG-I normally triggers the innate immune response by recognizing RNAs that have a triphosphate on their 5' end, as observed. Comparatively, the innate immune response to expression of circular Broccoli from a plasmid containing Tornado is less that the response to triphosphate containing RNA. Additionally, the response to circular Broccoli made by Tornado or by tricY is no different than the innate immune response to a similar plasmid expressing linear Broccoli RNA. This suggests that RtcB-derived circular RNAs do not trigger the innate immune response.

Nevertheless, RIG-I levels, which reflects activation of the innate immune pathway, in cell expressing circular Broccoli, were measured. A significant increase in RIG-I levels was observed when HeLa cells were transfected with RNA containing a terminal triphosphate (FIG. 7). These experiments were performed in HeLa cells because HEK293T cells lack the RIG-I pathway (Chen et al., "Sensing Self and Foreign Circular RNAs by Intron Identity," Mol. Cell 67(2):228-238 (2017), which is hereby incorporated by reference in its entirety). HeLa cells expressing linear Broccoli, circular Broccoli using the tricY system, or circular Broccoli using the Tornado system were compared. Expression of circular Broccoli did not show elevated levels of RIG-I activation compared to expression of the linear RNA (FIG. 7). In all cases, the level of RIG-I activation was vastly less than the levels of RIG-I activation induced by exogenous triphosphate-containing RNA. Overall, these data suggest that innate immune activation by RtcB-produced circles is negligible compared to conventional RNA expression systems.

Example 7—Tornado-Expressed Circular NF-κB Aptamers Modulate NF-κB Signaling in Mammalian Cells Numerous RNA aptamers have been generated, primarily as affinity reagents for pulldown experiments or other in vitro applications. In one case, several aptamers have been generated that bind the NF-κB protein subunits (p50 and p65) (Lebruska et al., "Selection and Characterization of an RNA Decoy for Transcription Factor NF-kappaB," Biochemistry 38(10):3168-3174 (1999) and Wurster et al., "Selection and Characterization of Anti-NF-κB p65 RNA Aptamers," RNA 14:1037 (2008), which are hereby incorporated by reference in their entirety). Dimerization of these subunits, which is inhibited by IκB, causes translocation to the nucleus where the dimer acts as a transcription factor. The p50-binding aptamer has been co-crystallized with the p50 protein (Huang et al., "Crystal Structure of NF-kappaB (p50)2 Complexed to a High-Affinity RNA Aptamer," Proc. Natl. Acad. Sci. U.S.A 100:9268-9273 (2003), which is hereby incorporated by reference in its entirety), while the binding of both the p50- and p65-binding aptamers to their target subunits has been well-documented (Cassiday et al., "Yeast Genetic Selections to Optimize RNA Decoys for Transcription Factor NF-kappa B," Proc. Natl. Acad. Sci. U.S.A 100:3930-3935 (2003) and Wurster et al., "Characterization of Anti-NF-κB RNA Aptamer-Binding Specificity In Vitro and in the Yeast Three-Hybrid System," Nucleic Acids Res. 37:6214-6224 (2009), which are hereby incorporated by reference in their entirety) and evolved for efficient binding in cells (Wurster et al., "Selections That Optimize RNA Display in the Yeast Three-Hybrid System," RNA 16:253-258 (2010), which is hereby incorporated by reference in its entirety). Therefore, whether these NF-κB-binding aptamers could be used to inhibit activation of the NF-κB pathway in cells was evaluated.

Figure 8A:
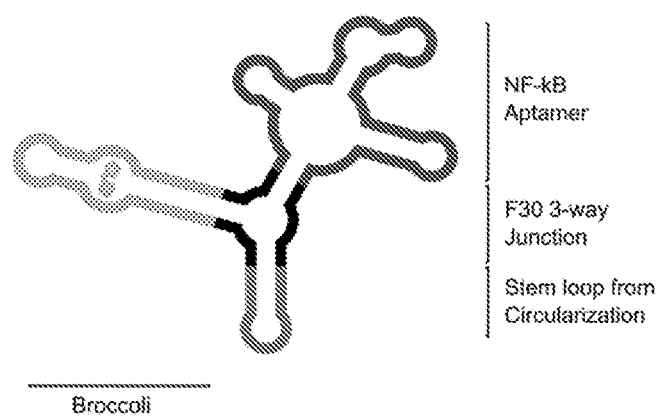
FIGS. 8A-8D show improved inhibition of NF-κB pathway by circRNA aptamers.
Figure 8B:
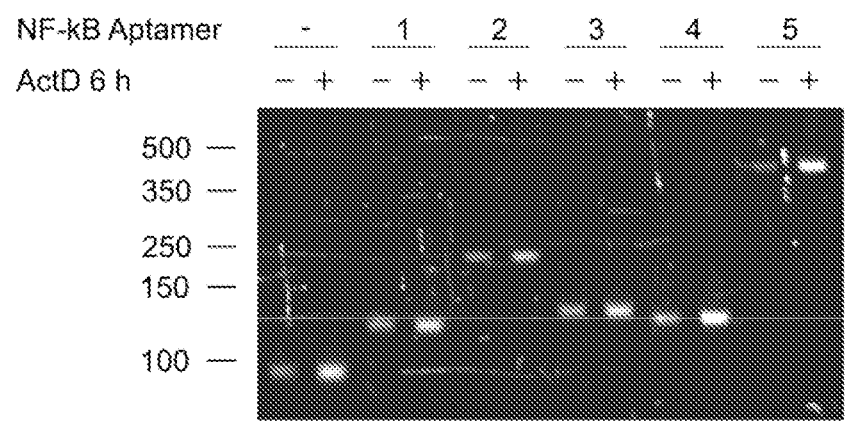

Before testing this idea, the p50- and p65-binding aptamers were expressed in HEK293 cells containing a luciferase reporter for NF-κB pathway activation to ensure that the aptamers are processed as circles. In these experiments, p50- and p65-binding aptamer were expressed as fusions with the Broccoli aptamers (FIG. 8A) so that cells expressing the aptamers could be visualized based on Broccoli fluorescence. The expression of these bifunctional circular RNAs, and a control linear form, which also contains both Broccoli and the p50- or p65-binding aptamer was confirmed by harvesting the cellular lysate, and resolving the RNA by denaturing gel electrophoresis (FIG. 8B). Staining the gel with DFHBI-1T demonstrated that the bifunctional circular RNAs were highly expressed compared to the linear form.

Figure 8C:
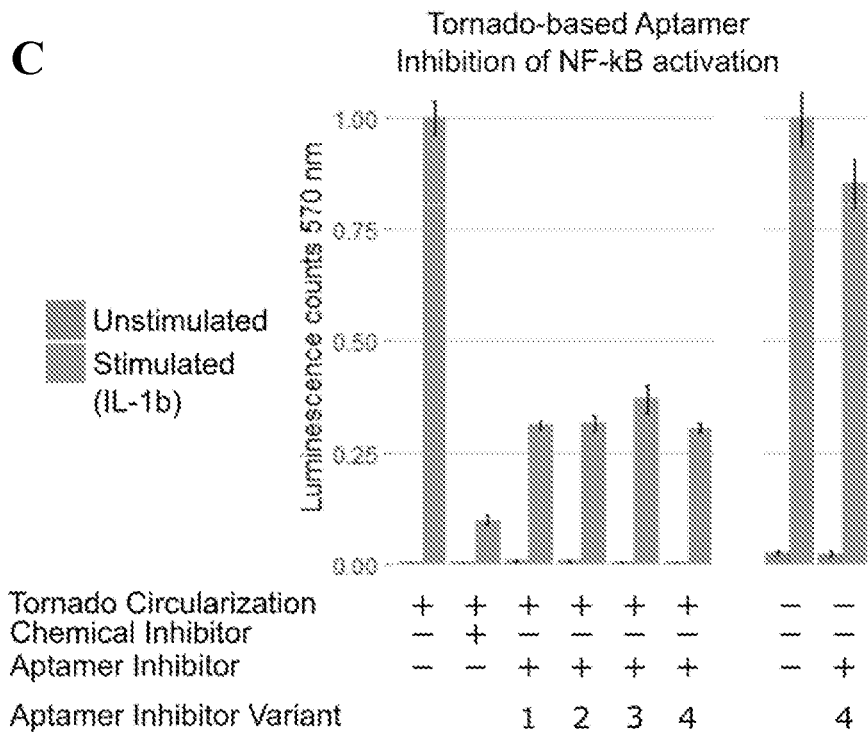

Initially, whether the bifunctional circular RNAs inhibit NF-κB signaling was evaluated. In these experiments, the NF-κB pathway was activated by application of IL-1β (50 ng/mL). In control cells that were mock-transfected, IL-1β treatment for 2.5 hours resulted in robust activation of the NF-κB pathway as measured by luciferase activity (FIG. 8C). This activity was dependent on the NF-κB pathway because BAY-11-7082, an inhibitor of the kinase that marks IκB for degradation, blocked IL-1β-mediated induction of the NF-κB pathway (FIG. 3C). These data confirmed that the reporter system accurately measures IL-1β-induced NF-κB pathway activation.

Figure 8D:
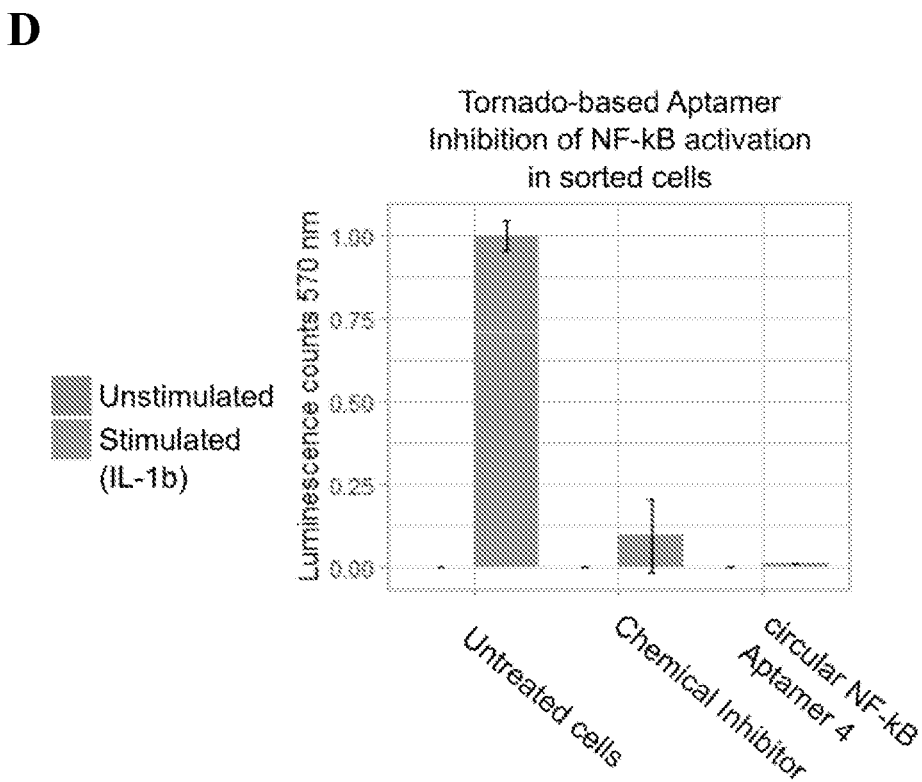

The effect of circular p50- and p65-binding aptamer expression on NF-κB pathway activation was next examined. In these cells, expressing the p65 aptamer fused with Broccoli showed marked inhibition of the NF-κB pathway in cells treated with IL-1β. Circular RNAs containing aptamers against p50 showed similar NF-κB pathway inhibition (FIG. 8C). By pre-sorting transfected cells with the strongest Broccoli fluorescence (and thus highest levels of bifunctional circRNA), inhibition of NF-κB activation at percentages similar to that of the chemical inhibitor were observed (FIG. 8D). Together, these experiments demonstrate that the p50- and p65-binding aptamers are effective inhibitors of the NF-κB pathway.

Notably, expression of the linear form of the p65-binding aptamer using the same U6 promoter resulted in a minimal but statistically significant reduction in pathway activation. The reduction of pathway activation was 5-fold stronger for the circular bifunctional RNA than that of the linear form. Thus, expression of the circular form of the p65 aptamer greatly enhanced this aptamer's function as a genetically encoded inhibitor of the NF-κB pathway.

Example 8—Tornado-Expressed SAM Sensor Enables Detection of SAM Dynamics in Mammalian Cells A major goal is to image the dynamic variation in fluxes of small molecules, metabolites, and signaling molecules inside living cells using fluorescence imaging. However, developing standard protein-based FRET sensors is very difficult in large part because they require a protein that binds to the molecule of interest. This protein additionally would have to undergo a conformational change that repositions fluorescent proteins to induce FRET upon binding the molecule. In contrast, sensors can more readily be developed using fluorogenic RNA aptamers, such as Spinach and Broccoli. Typically these sensors involve fusing an aptamer that binds the molecule of interest with the fluorogenic aptamer by a transducer stem that couples binding of the metabolite to the folding of the fluorogenic aptamer (Paige et al., "Fluorescence Imaging of Cellular Metabolites With RNA," *Science* 335:1194 (2012), which is hereby incorporated by reference in its entirety). This approach takes advantage of the relative speed and simplicity of generating an RNA that binds a molecule of interest, as opposed to generating a protein that binds to a molecule of interest. In principle, these sensors could have broad utility for imaging diverse types of molecules in cells.

Although this RNA-based approach to sensor design could be very powerful for imaging diverse metabolites, these RNA devices are highly unstable in mammalian cells. As a result, they have only been used in bacterial cells (Strack et al., "Using Spinach-Based Sensors for Fluorescence Imaging of Intracellular Metabolites and Proteins in Living Bacteria," *Nat. Protoc.* 9:146-155 (2013), which is hereby incorporated by reference in its entirety), many of which contain high levels of T7 RNA polymerase, thereby ensuring high expression in the bacterial cytosol.

Figures 9A, 9B, 9C:
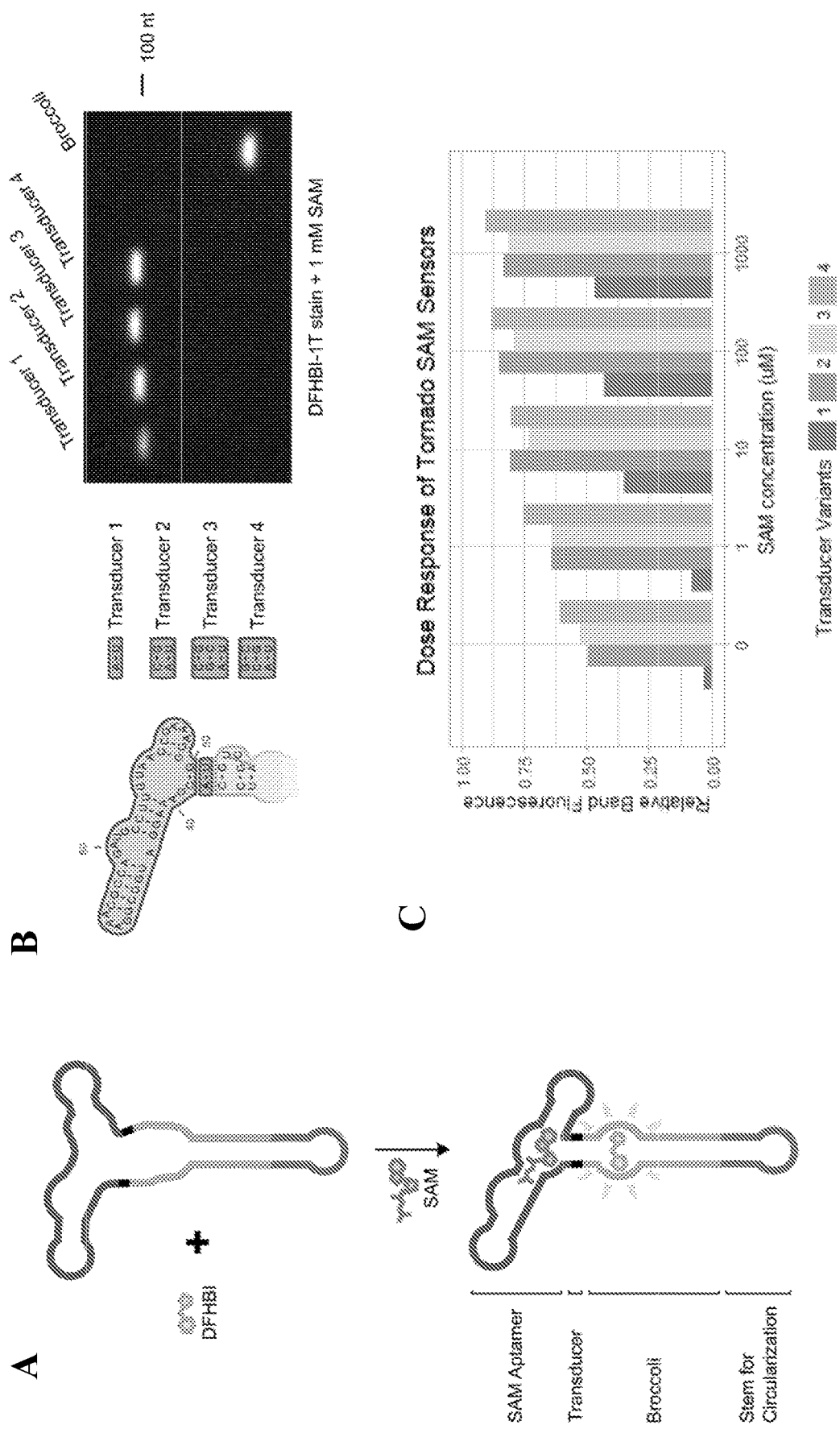
FIGS. 9A-9E show dynamic SAM detection in mammalian cells by circRNA-based sensors.

To determine if these RNA devices can be expressed at high levels in cells, the linear SAM sensor (Paige et al., "Fluorescence Imaging of Cellular Metabolites With RNA," *Science* 335:1194 (2012), which is hereby incorporated by reference in its entirety) was adapted for expression as a circle by the Tornado expression system. This device is composed of a SAM-binding aptamer derived from a SAM riboswitch, and Broccoli. As described previously, this biosensor is highly specific for SAM—it shows negligible binding to highly related molecules, including SAH (Paige et al., "Fluorescence Imaging of Cellular Metabolites With RNA," *Science* 335:1194 (2012), which is hereby incorporated by reference in its entirety). This sensor has been used to image SAM dynamics in bacterial cells. The Tornado expression construct was designed so that circularization occurs at the stem of Broccoli-SAM aptamer fusion (FIG. 9A).

Next, the circular SAM sensor was optimized to have the best signal relative to background. Four transducers of variable length and sequence were selected (FIG. 9B). These transducers were inserted between Broccoli and the SAM aptamer, expressed in cells, and the circular SAM sensor was isolated by gel extraction. The circular RNAs were resolved by gel electrophoresis and the background fluorescence and SAM-induced fluorescence was measured in the gel by iteratively adding increasing amounts of SAM to the DFHBI staining buffer (FIG. 9C). The sensor containing the shortest transducer (Transducer 1) exhibited the greatest signal relative to background and was used for detecting SAM in all experiments that followed.

Next, the optimized SAM biosensor was expressed as a linear and circular RNA in mammalian cells. In both cases the RNA was expressed using the U6 promoter. As expected, gel staining of whole cellular RNA from cells expressing the linear and circular form of the SAM sensor showed markedly higher expression of the circular SAM sensor.

Figure 9D:
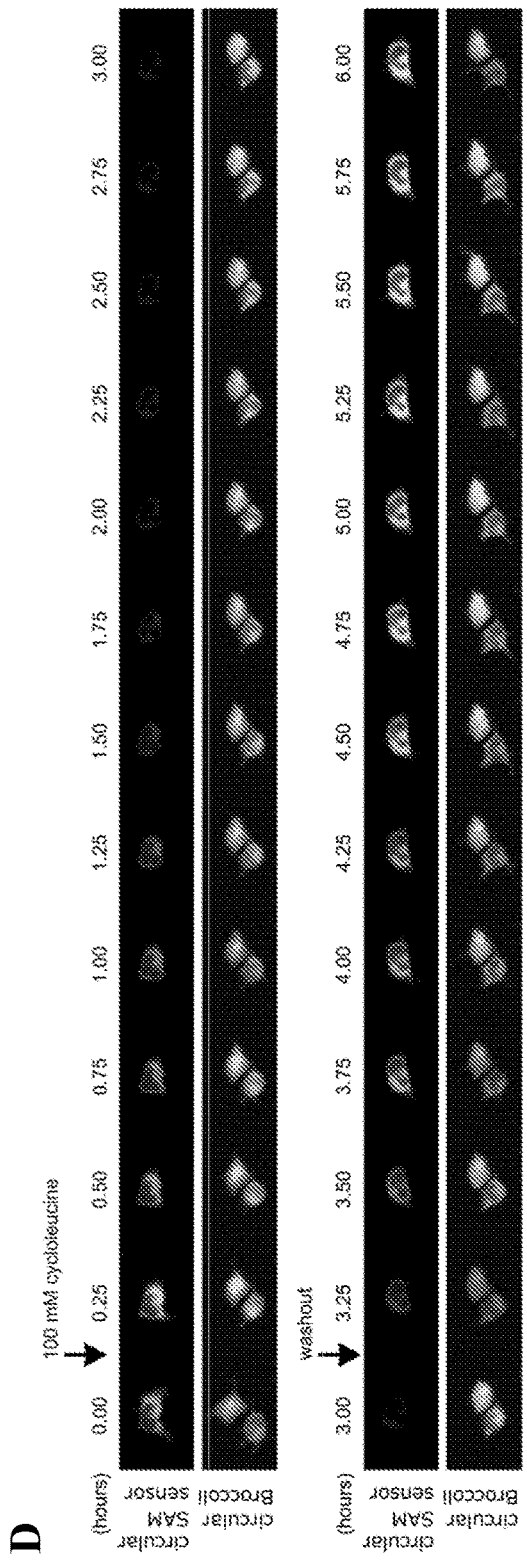
Figure 9E:
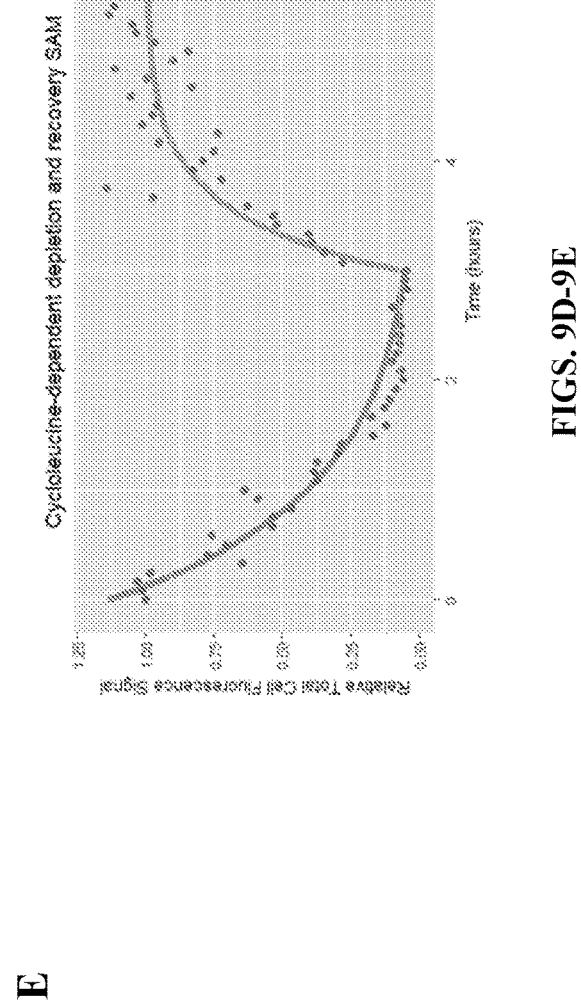

Whether the SAM sensor would enable detection of endogenous SAM levels in cells was next investigated. To test this, cycloleucine, which inhibits SAM biosynthesis (Lombardini et al., "Formation, Functions and Regulatory Importance of S-adenosyl-1-methionine," *Adv. Enzyme Regul.* 9:349-384 (1971), which is hereby incorporated by reference in its entirety) by binding to MAT2A (methionine adenosyltransferase IIα) was utilized. Within 30 minutes, a significant reduction in the fluorescence of cells expressing the SAM biosensor and complete disappearance within 2 hours was observed (FIG. 9D). As a control, cells expressing the circular Broccoli aptamer without the SAM aptamer were used. These cells showed no change in fluorescence following treatment with cycloleucine (FIG. 9D). Therefore, the reduction of the fluorescence in cells expressing the SAM biosensor reflects a selective effect of cycloleucine on intracellular SAM levels and not a nonspecific effect on Broccoli fluorescence.

Next, the cycloleucine was washed out to see if the drop in intracellular SAM levels could be reversed. Following replacement of the media with cycloleucine-free media, a rapid increase in SAM levels (FIG. 9D) to the fluorescence level observed at the beginning of the experiment was observed. No change in fluorescence was observed in the cells expressing the circular Broccoli (FIG. 9D). This demonstrates that the Tornado expression system allows the SAM biosensor to accumulate to a level that is sufficient to image metabolites in mammalian cells.

Example 9—Tornado-Expressed Trans-Spliced Circular RNA

Figure 10A:
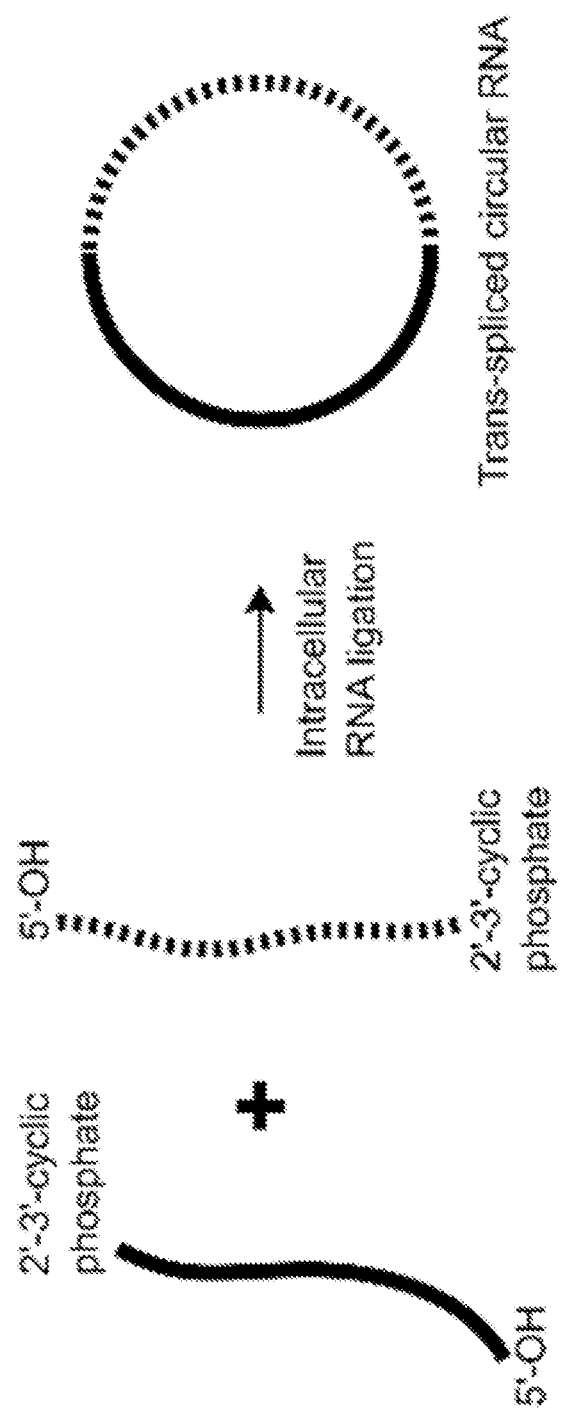
FIGS. 10A-10C show that splitting the orthogonal Tornado expression systems across two constructs can generate cleaved RNAs that hybridize and are trans-spliced into circular RNA.

Since RtcB can circularize a linear RNA that has been cleaved by ribozyme and contains an appropriate substrate sequence, whether two RNA molecules could become ligated to each other in two places to generate a single circular RNA comprising these the RNA molecules was next investigated (FIG. 10A). To do so, a second version Tornado having a pair of 5' and 3' tRNA exon sequences for ligation that has orthogonal complementarity to the original Tornado system was designed. This orthogonal pair of sequences contains forms "stem 2", whereas the original pair forms "stem 1"—both of which are substrates for RtcB.

Figure 10B:
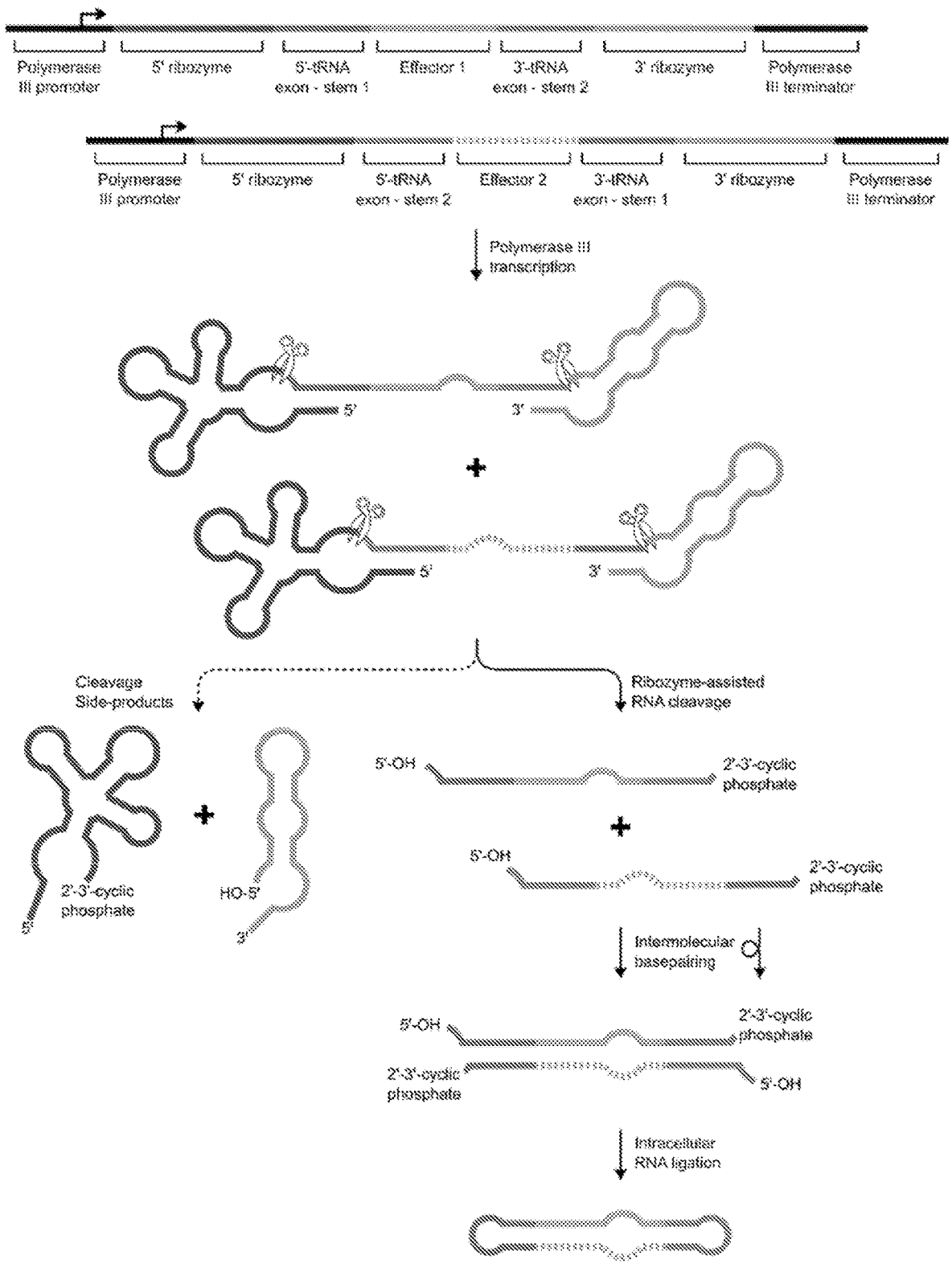

Next, a way to use the Stem 1 and Stem 2 versions of Tornado to generate cleaved RNAs that can become ligated twice so that they are spliced together in a circular RNA was designed. One Tornado construct was designed to contain the 5' Stem 1 sequence and a 3' Stem 2 sequence, while a second Tornado construct was designed to contain the 5' Stem 2 sequence and the 3' Stem 1 sequence (FIG. 10B). Thus, when cleavage occurs in both constructs, the cleaved RNAs can associate and present two different stems that are RtcB substrates. Ligation by RtcB of both substrates would lead to a circular RNA product.

Figure 10C:
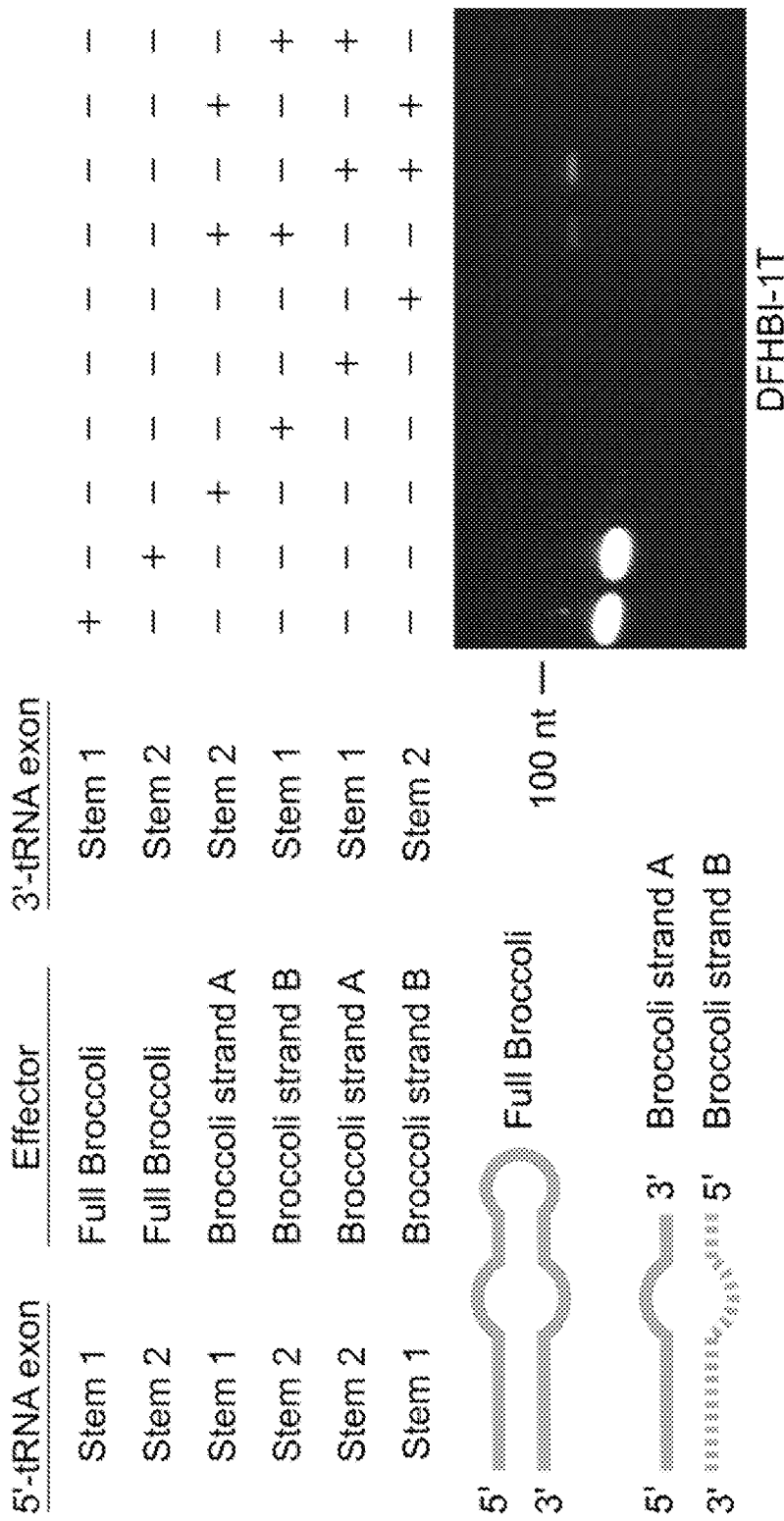

This concept was tested by splitting Broccoli into two strands (Strand A and Strand B), where each strand encodes one of the Tornado constructs described above. As expected, the Tornado expression system generates a Broccoli-fluorescent band using Stem 2 as abundant as when using the Stem 1 (FIG. 10C). None of the constructs expressing a mixture of Stem 1 and Stem 2 sequences can generate Broccoli fluorescent bands on their own, at all. However, when cotransfecting Tornado constructs that separately contain Strand A and Strand B, only a Broccoli fluorescent band is observed when the Stem 1 ends and Stem 2 ends are approximated after intermolecular base-pairing (FIG. 10C). No Broccoli fluorescent band products were observed when intermolecular base-pairing would assemble Stem 1 and 2 improperly. These results suggest that separate versions of the Tornado expression system can be designed to produce trans-spliced circular RNAs and, more broadly, that the Tornado expression system can generate 5'-OH and 2',3'-cyclic phosphates that are intermolecularly ligated.

Discussion of Examples 1-9

Synthetic RNA biology entails the use of engineered RNA to manipulate and image cellular function. Because RNA aptamers and devices are highly unstable in mammalian cells, synthetic biology rarely uses these genetically encodable tools. Examples 1-8 describe the Tornado expression system, which enables expressed RNAs to be converted into highly stable circular RNAs in cells. In Tornado, transcripts contain Twister ribozymes on either end of the transcript, resulting in autocatalytic processing, so that the RNA ends become substrates for the RNA ligase RtcB. The RNA then undergoes end-to-end ligation forming a circle. This expression system results in vastly higher levels of circular RNA than any other expression system, resulting in circular RNA at micromolar concentrations. As a result, Tornado-expressed circular RNA aptamers more efficiently inhibit the function of target proteins. Additionally, metabolite sensors composed of RNA can be circularized, allowing this class of biosensors to be used in mammalian cells to image metabolite dynamics. It is expected that the Tornado expression system will allow the power of aptamer technology to be exploited in living mammalian cells.

Transcripts expressed using Tornado are expected to circularize RNA in diverse cell types from diverse organisms. Circularization is dependent on the RNA ligase RtcB, which is expressed in many organisms, including all bacteria, archaea, and multicellular eukaryotes. These transcripts are expected to undergo autocatalytic processing in all cell types because the ribozyme undergoes cleavage spontaneously, without cellular cofactors. Therefore, circularization could be achieved in potentially any cell type.

Notably, circularization is facilitated by the hybridization of the RNA ends. Tornado-expressed transcripts were designed to produce complementary ends that hybridize each other and present the same ends as the tRNA$^{Tyr}$ intermediate that is the natural substrate of RtcB (FIG. 2). This stem becomes ligated by endogenous RtcB, circularizing the RNA. Therefore, RNA devices that have complementary ends, such as the aptamers and RNA devices used here would be readily incorporated into the Tornado expression system. However, RNA devices that do not have complementary ends may not be readily circularized using this system unless additional complementary sequences are added.

Aptamers are rarely expressed in mammalian cells, despite the ability of aptamers to modulate protein function. Raising an aptamer against a new target is a relatively straightforward process involving enrichment of sequences. New SELEX-based technologies have substantially shortened the SELEX-generation protocol, enabling aptamers to be generated in as little as 2 days (Szeto et al., "RAPID-SELEX for RNA Aptamers," *PLoS One* 8:e82667 (2013), which is hereby incorporated by reference in its entirety). However, RNA aptamers are mainly used as affinity reagents in vitro. The inability to express RNA aptamers and RNA devices at micromolar concentrations is the major reason why RNA aptamers have not been expressed in cells to exploit and manipulate protein function. The Tornado expression system should simplify the expression of RNA aptamers for diverse in cell applications.

The strategy for stabilizing the aptamers described here is markedly different than the strategies utilized by the cell to stabilize other RNAs. In most cases, small nuclear RNAs are highly stable in cells because they are part of ribo-nucleoprotein complexes that shield them from ribonucleases. For example, snRNAs are bound in spliceosomal protein complexes, while 5S and 5.8S are in ribosomal RNA complexes. MicroRNAs are resistant to exonucleases cleavage because their small size prevents them from binding exoribonucleases. Lastly, tRNA is highly structured and highly modified to make it resistant to ribonucleases. The circularization strategy described here enables the aptamers to be expressed in a stable form at high levels. Although it is not clear how circular RNAs are degraded, they may be susceptible to cellular endoribonucleases.

Circular RNAs are now known to be a normal component of the cell (Jeck et al., "Circular RNAs are Abundant, Conserved, and Associated With ALU Repeats," *RNA* 19:141-57 (2013), which is hereby incorporated by reference in its entirety). Notably, endogenous circular RNAs are generated by back-splicing, a process that involves the mRNA splicing machinery. Tornado-expressed transcripts are processed without the use of splicing machinery. Rather, processing involves the RtcB enzyme, a RNA ligase expressed in nearly all forms of life (Genschik et al., "The Human RNA 3'-Terminal Phosphate Cyclase is a Member of a New Family of Proteins Conserved in Eukarya, Bacteria and Archaea," *EMBO Journal*. 16:2955-2967 (1997), which is hereby incorporated by reference in its entirety). These transcripts are genetically encoded to generate the unusual ends required for RtcB substrates. Thus, the Tornado expression system represents a fundamentally novel strategy for generating circular RNA in cells. Notably, the efficiency of circular RNA generation is considerably higher than any previously described circular RNA expression system, thus enabling circular RNA to be expressed at levels on par with cellular proteins. As a result the Tornado-expression system allows RNA aptamers to be expressed at levels that can saturate protein-binding sites and modulate their function. It is expected that the Tornado expression system should allow researchers to take advantage of SELEX to create new tools to manipulate cellular function.

Although most previously described circular RNAs were localized in the nucleus, a high level of expression in the cytoplasm typically at levels greater than that seen in the nucleus were observed. It is not clear why the circular RNAs expressed using the Tornado system are found in the cytosol. Since RtcB has been observed in both the nucleus and the cytosol, the transcript may be exported before or after its circularization. While most endogenous circles are comprised of long sequences produced by backsplicing of exons (Rybak-Wolf et al., "Circular RNAs in the Mammalian Brain Are Highly Abundant, Conserved, and Dynamically Expressed," *Mol. Cell* 58(5):870-85 (2015) and Ashwal-Fluss et al., "CircRNA Biogenesis Competes With Pre-mRNA Splicing," *Mol. Cell* 56:55-66 (2014), which are hereby incorporated by reference in their entirety), the small circles generated here might be able to readily traverse the nuclear pore. Regardless, our data suggest that RNA aptamers and RNA devices expressed using the Tornado system should have access to cytosolic proteins and cytosolic metabolites.

Although the focus of Examples 1-8 above is on the expression of RNA aptamers and RNA devices as a major application for circular RNA, it is possible that other applications may be possible for circular RNAs. For example, circular RNAs are physiologically proposed to potentially serve as sponges for microRNAs (Hansen et al., "Natural RNA Circles Function as Efficient MicroRNA Sponges," *Nature* 495:384-388 (2013), which is hereby incorporated by reference in its entirety). However, endogenous circular RNA is expressed at much lower levels than the circular RNAs elicited by the Tornado expression system. Therefore, the circles may be especially useful for highly efficient sponging of specific microRNAs. Additionally, circular RNAs have been shown to be templates for translation in living cells (Chen et al., "Initiation of Protein Synthesis by the Eukaryotic Translational Apparatus on Circular RNAs," *Science* 268:415-417 (1995) and Wang et al., "Efficient Backsplicing Produces Translatable Circular mRNAs," *RNA* 21(2):172-179 (2015), which is hereby incorporated by reference in its entirety). Conceivably the high-level expression of circular RNAs described here, provided that they contain an internal ribosome entry site, could provide new approaches for highly efficient translation due to the high levels of transcript expression that can be achieved using the system.

Although the circular RNA expressed here did not elicit an innate immune response (FIG. 10), it is possible that different circular RNAs with different sequences might produce these effects. For example, if the circular RNA contains an intended or unintended consensus sequence for an important RNA-binding protein or microRNA, the circular RNA could elicit cytotoxicity or an innate immune response. It will be important to evaluate the cytotoxicity and innate immune response in animals. Different cells and tissues in living animals may have different efficiencies of circularization, and the mechanisms of circular RNA degradation, which are currently unknown might vary between the cells. Additionally, levels of circular RNA in tissue culture cells may be diluted upon cell division, which occurs less frequently in animal tissue. Thus the final circular RNA concentration in different tissues may diminish any sequence-related toxicity.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An RNA molecule comprising:
   a first ribozyme;
   a first ligation sequence positioned 3' to the first ribozyme;
   an effector molecule positioned 3' to the first ligation sequence;
   a second ligation sequence positioned 3' to the effector molecule; and
   a second ribozyme positioned 3' to the second ligation sequence,
   wherein a portion of the first ligation sequence is complementary to a portion of the first ribozyme and a portion of the second ligation sequence is complementary to a portion of the second ribozyme; wherein a portion of the first ligation sequence is complementary to a portion of the second ligation sequence; and wherein the portion of the first ligation sequence complementary to the portion of the first ribozyme is complementary to the portion of the second ligation sequence complementary to the portion of the second ribozyme.

2. The RNA molecule of claim 1, wherein the RNA molecule comprises a non-natural or modified nucleotide.

3. The RNA molecule of claim 1, wherein each of the first ribozyme and the second ribozyme comprises a sequence that may be cleaved to produce a 5'-OH end and a 2',3'-cyclic phosphate end.

4. The RNA molecule of claim 3, wherein each of the first and the second ribozyme is independently selected from the group consisting of Hammerhead, Hairpin, Hepatitis Delta Virus ("HDV"), Varkud Satellite ("VS"), Vg1, glucosamine-6-phosphate synthase ("glmS"), Twister, Twister Sister, Hatchet, Pistol ribozymes, engineered synthetic ribozymes, or derivatives thereof.

5. The RNA molecule of claim 4, wherein each of the first and the second ribozyme is, independently, a split ribozyme or ligand-activated ribozyme derivative.

6. The RNA molecule of claim 3, wherein the first ribozyme is a P3 Twister ribozyme and the second ribozyme is a P1 Twister ribozyme.

7. The RNA molecule of claim 1, wherein each of the first ligation sequence and the second ligation sequence are substrates for an RNA ligase.

8. The RNA molecule of claim 7, wherein each of the first ligation sequence and the second ligation sequence comprise a portion of a tRNA exon sequence or derivative thereof.

9. The RNA molecule of claim 7, wherein the RNA ligase is RtcB.

10. The RNA molecule of claim 1, wherein the effector molecule is selected from the group consisting of a RNA sequence that binds a protein; an RNA sequence that is complementary to a microRNA or siRNA; an RNA sequence that has partial complementarity to a microRNA or siRNA or piRNA; an RNA sequence that hybridizes completely or partially to a cellularly expressed microRNA, siRNA, piRNA, mRNA, lncRNA, ncRNA, or other cellular RNA; a hairpin structure that is a substrate for DICER or endogenous nucleases; a sequence that binds to viral proteins; an antisense RNA, an antagomir, a microRNA, a siRNA, an anti-miRNA, a ribozyme, a decoy oligonucleotide, an RNA activator, an immunostimulatory oligonucleotide, an aptamer, an RNA device; and an RNA molecule encoding a peptide sequence.

11. The RNA molecule of claim 10, wherein the effector molecule comprises an IRES coupled to an RNA molecule encoding a peptide sequence.

12. The RNA molecule of claim 10, wherein the effector molecule is a sensor comprising a fluorogenic aptamer coupled to a metabolite binding partner.

13. The RNA molecule of claim 12, wherein the fluorogenic aptamer is selected from Spinach, Spinach 2, Broccoli, Red-Broccoli, Orange Broccoli, Corn, Mango, Malachite Green, cobalamine-binding aptamer, and derivatives thereof.

14. The RNA molecule of claim 13, wherein the fluorogenic aptamer binds to a fluorophore whose fluorescence, absorbance, spectral properties, or quenching properties are increased, decreased, or altered by interaction with the fluorogenic aptamer.

15. A circular RNA molecule produced from the RNA molecule of claim 1, wherein the circular molecule comprises the effector molecule.

16. A vector encoding the RNA molecule of claim 1.

17. The vector of claim 16, wherein the vector comprises a prokaryotic promoter selected from the group consisting of T7, T3, SP6 RNA polymerases, and derivatives thereof.

18. The vector of claim 16, wherein the vector comprises a eukaryotic RNA polymerase I promoter or RNA Polymerase III promoter selected from the group consisting of U6, H1, 5S, 7SK promoter, and derivatives thereof.

19. An isolated cell comprising the vector of claim 16.

20. A method of producing a circular RNA molecule, said method comprising:
providing one or more vectors comprising:
a nucleic acid sequence encoding a 5' polymerase promoter sequence;
a nucleic acid sequence encoding a first ribozyme;
a nucleic acid sequence encoding a first ligation sequence;
a nucleic acid sequence encoding an effector molecule;
a nucleic acid sequence encoding a second ligation sequence;
a nucleic acid sequence encoding a second ribozyme; and
a nucleic acid sequence encoding a 3' polymerase terminator sequence, wherein (i) said nucleic acid sequence encoding the first ligation sequence is upstream of the nucleic acid sequence encoding the effector molecule, (ii) said nucleic acid sequence encoding the second ligation sequence is downstream of the effector molecule, (iii) a portion of the first ligation sequence is complementary to a portion of the first ribozyme and a portion of the second ligation sequence is complementary to a portion of the second ribozyme, (iv) a portion of the first ligation sequence is complementary to a portion of the second ligation sequence, and (v) wherein the portion of the first ligation sequence complementary to the portion of the first ribozyme is complementary to the portion of the second ligation sequence complementary to the portion of the second ribozyme;
transcribing the one or more vectors to produce one or more linear RNA molecules; and
contacting the linear RNA molecules with an RNA ligase to circularize the linear RNA molecule thereby producing a circular RNA molecule.

21. A method of treatment, said method comprising:
administering the RNA molecule of claim 1 to a subject in need thereof, wherein upon said administering to the subject, the effector molecule is expressed in a cell of the subject, thereby treating the subject.

22. The RNA molecule of claim 1, wherein the first ribozyme or the second ribozyme are self-cleaving ribozymes.

* * * * *